US007192924B2

(12) United States Patent
Isfort et al.

(10) Patent No.: US 7,192,924 B2
(45) Date of Patent: Mar. 20, 2007

(54) CORTICOTROPIN RELEASING FACTOR 2 RECEPTOR AGONISTS

(75) Inventors: Robert Joseph Isfort, Fairfield, OH (US); Wieslaw Adam Mazur, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 766 days.

(21) Appl. No.: 10/317,251

(22) Filed: Dec. 11, 2002

(65) Prior Publication Data

US 2003/0148957 A1    Aug. 7, 2003

Related U.S. Application Data

(60) Provisional application No. 60/411,988, filed on Sep. 19, 2002, provisional application No. 60/388,895, filed on Jun. 16, 2002, provisional application No. 60/376,337, filed on Apr. 29, 2002, provisional application No. 60/349,117, filed on Jan. 16, 2002.

(51) Int. Cl.
| A61K 38/16 | (2006.01) |
| A61K 38/22 | (2006.01) |
| C07K 14/435 | (2006.01) |
| C07K 14/575 | (2006.01) |

(52) U.S. Cl. ............................ 514/12; 514/21; 530/324
(58) Field of Classification Search ...................... None
See application file for complete search history.

(56) References Cited

U.S. PATENT DOCUMENTS

| 5,235,036 A | 8/1993 | Kornreich et al. |
| 5,663,292 A | 9/1997 | Rivier |
| 5,786,203 A | 7/1998 | Lovenberg et al. |
| 5,824,771 A | 10/1998 | Rivier |
| 5,844,074 A | 12/1998 | Rivier |
| 5,869,450 A | 2/1999 | Wei et al. |

FOREIGN PATENT DOCUMENTS

| EP | 0 860 501 A2 | 8/1998 |
| WO | WO 96/37223 A1 | 11/1996 |
| WO | WO 97/00063 A2 | 1/1997 |
| WO | WO 97/32898 A1 | 9/1997 |
| WO | WO 02/12307 A1 | 2/2002 |
| WO | WO 02/34934 A2 | 5/2002 |

OTHER PUBLICATIONS

T.M. Reyes, et al., "Urocortin II: A member of the corticotropin-releasing factor (CRF) neuropeptide family that is selectively bound by type 2 CRF receptors", PNAS, vol. 98, No. 5, pp. 2843-2848 (2001).
E.B De Souza, et al., "Corticotropin-Releasing Factor Receptors: Physiology, Pharmacology, Biochemistry and Role In Central Nervous System and Immune Disorders", Psychoneuroendocrinology, Elsevier Science Ltd., USA , vol. 20, No. 8. pp. 789-819 (1995).

D.T. Chalmers, et al., "Corticotropin-releasing factor receptors: from molecular biology to drug design", TiPS, Elsevier Science Ltd., USA, vol. 17, pp. 166-172, (1996).
H.A. Thomas, et al., "CRF and Related Peptides as Anti-Inflammatory Agonists", Annals New York Academy of Sciences, pp. 219-228 (1993).
E.T. Wei, et al., "Peripheral anti-inflammatory actions of corticotropin-releasing factor", Ciba Foundation Symposium 172, Wiley, Chichester , pp. 258-276, (1993).
J.R. McCarthy, et al., "Recent Advances with the $CRF_1$ Receptor: Design of Small Molecule Inhibitors, Receptor Subtypes and Clinical Indications", Current Pharmaceutical Design, , Bentham Science Publishers B.V. vol. 5 pp. 289-315 (1999).
J.R. McCarthy, et al., "Chapter 2. Recent Progress in Corticotropin-Releasing Factor Receptor Agents", Annual Reports in Medicinal Chemistry, Academic Press, vol. 34, pp. 11-20 (1999).
G.P. Chrousos, et al., "Corticotropin Releasing Factor: Basic Studies and Clinical Applications", Prog. Neuro-Psychopharmacol. & Biol. Psychiat., Pergamon Press Ltd, Great Britain, vol. 9, pp. 349-359 (1985).
G.B. Cutler, Jr., M.D., "Cortic tropin-Releasing H rmon (CRH): Clinical Studies and Use", The Endocrinologist, Suppl. 1, Williams & Wilkins, vol. 7, No. 1, pp. 10S-16S (1997).
M.J. Owens, et al., "Physiol gy and Pharmac logy of Corticotropin-r leasing Factor", Pharmacological R views, Th American Society for Pharmac l gy and Experimental Th rap utics, USA. V l. 43, No. 4, pp. 425-473 (1991).
L. Arborelius, et al., "The role of corticotr pin-releasing fact r in depr ssion and anxi ty dis rders", Journal of Endocrinology, Society f r Endocrinol gy, Gr at Britain, V l. 160, pp. 1-12 (1999).
D.N. Orth, "C rticotropin-R leasing Hormone in Humans", Endocrine Reviews, The Endocrine Soci ty, USA., V l. 13, No. 2, pp. 164-191 (1992).
E. Emeric-Sauval, "C rticotropin-Rel asing Factor (CRF)—A R view", Psychoneuroendocrinology, Pergamon Journals Ltd., Great Britain , V l. 11, N . 3, pp. 277-294 (1985).
J. Spiess, et al., "Molecular Properties of the CRF Receptor", TEM, Elsevier Science Ltd., vol. 9, No. 4, pp. 140-145 (1998).
K.D. Dieterich, et al., "Corticotropin-releasing factor receptors: An overview", Exp. Clin. Endocrinol. Diabetes, Johann Ambrosius Barth, vol. 105, pp. 65-82 (1997).
P.J. Gilligan, et al., "Corticotropin Releasing Factor (CRF) Receptor Modulators: Progress and Opportunities for New Therapeutic Agents", Journal of Medicinal Chemistry, American Chemical Society, vol. 43, No. 9, pp. 1641-1660 (2000).
C.A. Maltin, et al., "Clenbuterol, a β-adrenoceptor agonist, increases relative muscle strength in orthopaedic patients", Clinical Science, vol. 84, pp. 651-654 (1993).

(Continued)

Primary Examiner—Jeffrey Edwin Russel
(74) Attorney, Agent, or Firm—Andrew A. Paul; David V. Upite; Mary Pat McMahon

(57) ABSTRACT

Isolated corticotropin releasing factor derivatives, and nucleic acids encoding the same, are effective for treating corticotropin releasing factor 2 receptor modulated disorders such as muscular dystrophy.

37 Claims, No Drawings

OTHER PUBLICATIONS

J.F. Signorile, et al., "Increased Muscle Strength in Paralyzed Patients after Spinal Cord Injury: Effect of Beta-2 Adrenergic Agonist", *Arch Phys Med Rehabil*, vol. 76, pp. 55-58 (1995).

L. Martineau, et al., "Salbutamol, a $\beta_2$-adrenoceptor agonist, increases skeletal muscle strength in young men", *Clinical Science*, vol. 83. pp. 615-621 (1992).

M.H. Perrin, et al., "Diverse roles of corticotropin releasing factor receptors and their ligands", *Amer. Zoologist*, vol. 40, No. 6, pp. 1168-1169 (2000).

O. Valdenaire, et al., "A new functional isoform of the human CFR2 receptor for corticotropin releasing factor", *Biochimica et Biophysica Acta*, vol. 1352, pp. 129-132 (1997).

M.R Palchaudhuri, et al., "Isolation and pharmacological characterization of two functional splice variants of corticotropin-releasing factor type 2 receptor from Tulpaia belangen", *J. of Neuroendocrinology*, vol. 11, pp. 419-428 (1999).

D.E. Grigoriadis, et al., "$^{125}$I-Tyr$^0$-Sauvagine: A novel high affinity radioligand for the pharmacological and biochemical study of human corticotropin-releasing factor$_{2\alpha}$ receptors", *Molecular Pharmacology*, vol. 50, pp. 679-686 (1996).

N. Suman-Chauhan, et al., "Expression and characterisation of human and rat CRF$_{2\alpha}$ receptors", *Eur. J. Pharmacol.*, vol. 379, pp. 219-227 (1999).

T. Kishimoto, et al., "A sauvagine/ corticotropin-releasing factor receptor expressed in heart and skeletal muscle", *Proc. Natl. Acad. Sci. USA*, vol. 92, pp. 1108-1112 (1995).

T. Bale, et al., "Mice Deficient for Both Corticotropin—Releasing Factor Receptor 1 (CRFR1) and CRFR2 Have an Impaired Stress Response and Display Sexually Dichotomous Anxiety—Like Behavior", *The Journal of Neuroscience*, vol. 22, No. 1, pp. 193-199 (2002).

M. Perrin, et at., "Corticotropin Releasing Factor Receptors and Their Ligand Family", *Annals New York Academy of Sciences*, pp. 312-328, (Not dated).

K. Lewis, et al., "Identification of urocortin III, an additional member of the corticotropin-releasing factor (CRF) family with high affinity for the CRF2 receptor", *PNAS*, vol. 98, No. 13, pp. 7570-7575, (2001).

S. Hsu, et al., "Human stresscopin and stresscopin—related peptide are selective ligands for the type 2 corticotropin—releasing hormone receptor", *Nature Medicine*, vol. 7, No. 5, p. 611 (2001).

H. Appell, et al., "Muscular Atrophy Following Immobilisation A Review", *Sports Medicine*, vol. 10, No. 1, pp. 42-58 (1990).

G. Smith, et al., "Corticotropin Releasing Factor Receptor 1—Deficient Mice Display Decreased Anxiety, Impaired Stress Response, and Aberrant Neuroendocrine Development", *Neuron*, vol. 20 pp. 1093-1102 (1998).

C. Rossant, et al., "Corticotropin—Releasing Factor Type 1 and Type 2$\alpha$ Receptors Regulate Phosphorylation of Calcium/Cyclic Adenosine 3',5'-Monophosphate Response Element-Binding Protein and Activation of p42/p44 Mitogen-Activated Protein Kinase", *Endocrinology*, vol. 140, No. 4, pp. 1525-1536 (1999).

K. Heldwein, et al., "Corticotropin-Releasing Hormone Receptor Expression and Functional Coupling in Neonatal Cardiac Myocytes and AT-1 Cells*", *Endocrinology*, vol. 137, No. 9, pp. 3631-3639 (1996).

Y. Kuryshev, et al., "Corticotropin—Releasing Hormone Stimulation of Ca$^{2+}$ Entry in Corticotropes Is Partially Dependent on Protein Kinase A*", *Endocrinology*, vol. 136, No. 9, pp. 3925-3935 (1995).

T. Lovenberg, et al., "CRF$_{2\alpha}$ and CRF$_{2\beta}$ receptor mRNAs are differentially distributed between the rat central nervous system and peripheral tissues." *Endocrinology*, vol. 136, No. 9, pp. 4139-4142 (1995).

M. Tisdale, t al., "Biology of Cach xia", *Journal of the National Cancer Institute*, vol. 89, No. 23, pp. 1763-1773 (1997).

S. Coste, et al., "Abnormal adaptations t str ss and impaired cardi vascular function in mice lacking corticotropin—releasing hormone recept r-2", *Nature Genetics*, vol. 24, pp. 403-409 (2000).

T. Bale, et al., "Mice d ficient for cortic tropin—releasing horm n receptor-2 display anxiety—lik behavi r and are hypersensitive to str ss", Nature Genetics, vol. 24, pp. 410-414 (2000).

T. Kishimoto, et al., "Deletion of *Crhr2* reveals an anxi lytic rol for corticotropin-r leasing h rm n receptor-2", *Nature Genetics*, vol. 24, pp. 415-419 (2000).

P. Timpl, t al., "Impair d stress response and reduced anxi ty in mic lacking a functi nal corticotropin-releasing hormone receptor 1", *Nature G netics*, V l. 19, pp. 162-166 (1998).

F. Dautezenberg, t al., "The CRF peptide family and their receptors: yet m re partners discov r d" *Trends in Pharmacological Sciences*, vol. 23, No. 2, pp. 71-77 (2002).

Eckart, K. et al., "A single amino acid serves as an affinity switch between the receptor and the binding protein of corticotropin-releasing factor: implications for the design of agonists and antagonists", *Proceedings of the National Academy fo Sciences of the United States*, 2001, vol. 98, No. 20, pp. 11142-11147.

Beyermann, M. et al., "A single-point slight alteration set as a tool for structure-activity relationship studies of ovine corticotropin releasing factor", *J. Medicinal Chemistry*, 1996, vol. 39, No. 17, pp. 3324-3330.

Korneich, W.D. et al., "Alanine Series Of Ovine Corticotropin Releasing Factor (oCFR): A structure—Activity Relationship Study", *J. of Medicinal Chemistry, Amer. Chem. Society*, 1992, vol. 35, No. 10, pp. 1870-1876.

Ruhmann, A. et al., "Structural requirements for peptidic antagonists of the corticotropin-releasing factor receptor (CRFR): Development of CRFR2$\beta$-selective antisauvagine-30", *Proceedings of the National Academy of Sciences of the United States*, 1998, vol. 95, No. 26, pp. 15264-15269.

Assil, I. Q. et al., "An Oxidation resistant radioligand for corticotropin-releasing factor receptors", *Peptides*, 2001, vol. 22, No. 7, pp. 1055-1061.

CORTICOTROPIN RELEASING FACTOR 2 RECEPTOR AGONISTS

CROSS REFERENCE TO RELATED APPLICATIONS

This application claims priority from U.S. Provisional Applications Ser. Nos. 60/349,117, filed Jan. 16, 2002, 60/376,337, filed Apr. 29, 2002, 60/388,895 filed Jun. 14, 2002, and 60/411,988 filed Sep. 19, 2002, all of which are herein incorporated by reference in their entirety.

REFERENCE TO A SEQUENCE LISTING

This Application contains a Sequence Listing appendix, provided as a paper copy, as required under 37 CFR §1.821 (c), and is herein incorporated by reference in its entirety, as required by 37 CFR §1.52(e)(5). A copy of the sequence listing is also provided as required under 37 CFR §1.821(e), as a Computer Readable Form (CRF) on a diskette.

FIELD OF INVENTION

This invention relates to the use of novel peptides, and nucleic acids encoding the same, to treat $CRF_2R$ modulated disorders.

BACKGROUND

CRFR and Ligands

There are at least two corticotropin releasing factor (CRF) receptors identified to date ($CRF_1R$ and $CRF_2R$) which belong to G-protein coupled receptor (GPCR) class. Agonist activation of $CRF_1R$ or $CRF_2R$ leads to $G_{\alpha s}$ activation of adenylate cyclase. Adenylate cyclase catalyzes the formation of cAMP, which in turn has multiple effects including the activation of protein kinase A, intracellular calcium release and activation of mitogen-activated protein kinase (MAP kinase). In other studies, the enhancement of intracellular inositol triphosphate synthesis, after agonist activation of CRF receptors, suggests that CRFRs also couple to $G_{\alpha q}$.

$CRF_1R$ and $CRF_2R$ have been cloned from human, rat, mouse, chicken, cow, catfish, frog and sheep. $CRF_1R$ and $CRF_2R$ each have a unique distribution patterns. In humans three isoforms, alpha, beta and gamma, of the $CRF_2R$ receptor have been cloned. Homologs for alpha and beta $CRF_2R$ have been identified in rat.

Several ligands/agonists of the CRFRs are known and include corticotropin releasing factor (or hormone, CRF, CRH), urocortin I, urocortin II (or stresscopin related peptide), urocortin III (or stresscopin), urotensin I, sauvagine and other related peptides. Corticotropin releasing factor binds to and activates $CRF_1R$ and $CRF_2R$. CRF is a major modulator of the body's responses to stress. This 41-amino acid peptide presides over a panoply of neuronal, endocrine, and immune processes as the primary regulator of the hypothalamus-pituitary-adrenal hormonal axis (HPA axis). In addition, there is substantial sequence homology between all known ligands of CRFR. Further, two $CRF_2R$ selective ligands have been identified, urocortin II (or stresscopin related peptide) and urocortin III (stresscopin). These peptides have been identified from multiple mammalian and fish species.

The CRF receptors can be distinguished, from non-CRFRs, pharmacologically through the use of receptor selective agonists and antagonists. These selective agonists and antagonist, along with the CRFR knockout mice, have been useful in determining which CRF receptor mediates a particular biological response.

The role of $CRF_1R$ has been fairly well established. Mice in which the $CRF_1R$ gene has been ablated ($CRF_1R$ knockout) demonstrate an impaired stress response and reduced anxiety-like behavior. $CRF_1R$ is a major mediator of the HPA axis. Specifically, CRF, which is released from the hypothalamus and transported to the anterior pituitary via the hypothalamic-hypophysial portal system, interacts with the $CRF_1R$ present on cells located in the anterior pituitary. Agonist activation of the $CRF_1R$ results in release of ACTH from the cells of the anterior pituitary into the systemic circulation. The released ACTH binds the ACTH receptor present on cells located in the adrenal cortex, resulting in the release of adrenal hormones including corticosteroids. Corticosteroids mediate many effects including, but not limited to, immune system suppression via a mechanism, which involves thymic and splenic atrophy. Thus activation of the $CRF_1R$ indirectly results in the down-regulation of the immune system via activation of the HPA axis.

The role of $CRF_2R$ is less well established. Mice in which the $CRF_2R$ gene has been ablated ($CRF_2R$ knockout) demonstrate an impaired or reduced food intake following stimulation with urocortin, lack of vasodilation, but a normal stress response. Experiments with $CRF_2R$ demonstrated that $CRF_2R$ is responsible for the hypotensive/vasodilatory effects of CRFR agonists and for the reduction in food intake observed following treatment of mice with CRFR agonists.

Skeletal Muscle Atrophy and Hypertrophy

In addition, $CRF_2R$ is involved in the modulation of skeletal muscle atrophy and the induction of hypertrophy. Skeletal muscle is a plastic tissue, which readily adapts to changes in either physiological demand for work or metabolic need. Hypertrophy refers to an increase in skeletal muscle mass while skeletal muscle atrophy refers to a decrease in skeletal muscle mass. Acute skeletal muscle atrophy is traceable to a variety of causes including, but not limited to: disuse due to surgery, bed rest, or broken bones; denervation/nerve damage due to spinal cord injury, autoimmune disease, or infectious disease; glucocorticoid use for unrelated conditions; sepsis due to infection or other causes; nutrient limitation due to illness or starvation; and space travel. Skeletal muscle atrophy occurs through normal biological processes, however, in certain medical situations this normal biological process results in a debilitating level of muscle atrophy. For example, acute skeletal muscle atrophy presents a significant limitation in the rehabilitation of patients from immobilizations, including, but not limited to, those accompanying an orthopedic procedure. In such cases, the rehabilitation period required to reverse the skeletal muscle atrophy is often far longer than the period of time required to repair the original injury. Such acute disuse atrophy is a particular problem in the elderly, who may already suffer from substantial age-related deficits in muscle function and mass, because such atrophy can lead to permanent disability and premature mortality.

Skeletal muscle atrophy can also result from chronic conditions such as cancer cachexia, chronic inflammation, AIDS cachexia, chronic obstructive pulmonary disease (COPD), congestive heart failure, genetic disorders, e.g., muscular dystrophies, neurodegenerative diseases and sarcopenia (age associated muscle loss). In these chronic conditions, skeletal muscle atrophy can lead to premature loss of mobility, thereby adding to the disease-related morbidity.

Little is known regarding the molecular processes which control atrophy or hypertrophy of skeletal muscle. While the initiating trigger of the skeletal muscle atrophy is different for the various atrophy initiating events, several common biochemical changes occur in the affected skeletal muscle fiber, including a decrease in protein synthesis and an increase in protein degradation and changes in both contractile and metabolic enzyme protein isozymes characteristic of a slow (highly oxidative metabolism/slow contractile protein isoforms) to fast (highly glycolytic metabolism/fast contractile protein isoforms) fiber switch. Additional changes in skeletal muscle, which occur, include the loss of vasculature and remodeling of the extracellular matrix. Both fast and slow switch muscle demonstrate atrophy under the appropriate conditions, with the relative muscle loss depending on the specific atrophy stimuli or condition. Importantly, all these changes are coordinately regulated and are switched on or off depending on changes in physiological and metabolic need.

The processes by which atrophy and hypertrophy occur are conserved across mammalian species. Multiple studies have demonstrated that the same basic molecular, cellular, and physiological processes occur during atrophy in both rodents and humans. Thus, rodent models of skeletal muscle atrophy have been successfully utilized to understand and predict human atrophy responses. For example, atrophy induced by a variety of means in both rodents and humans results in similar changes in muscle anatomy, cross-sectional area, function, fiber type switching, contractile protein expression, and histology. In addition, several agents have been demonstrated to regulate skeletal muscle atrophy in both rodents and in humans. These agents include anabolic steroids, growth hormone, insulin like growth factor I, beta-adrenergic agonists, and $CRF_2R$ agonists. Together, these data demonstrate that skeletal muscle atrophy results from common mechanisms in both rodents and humans.

While some agents have been shown to regulate skeletal muscle atrophy and are approved for use in humans for this indication, these agents have undesirable side effects such as hypertrophy of cardiac muscle, neoplasia, hirsutism, androgenization of females, increased morbidity and mortality, liver damage, hypoglycemia, musculoskeletal pain, increased tissue turgor, tachycardia, and edema. Currently, there are no highly effective and selective treatments for either acute or chronic skeletal muscle atrophy. Thus, there is a continuing need to identify other therapeutic agents, which treat skeletal muscle atrophy.

Muscular Dystrophies

Muscular dystrophies encompass a group of inherited, progressive muscle disorders, distinguished clinically by the selective distribution of skeletal muscle weakness. The two most common forms of muscle dystrophy are Duchenne and Becker dystrophies, each resulting from the inheritance of a mutation in the dystrophin gene, which is located at the Xp21 locus. Other dystrophies include, but are not limited to, limb-girdle muscular dystrophy which results from mutation of multiple genetic loci including the p94 calpain, adhalin, γ-sarcoglycan, and β-sarcoglycan loci; fascioscapulohumeral (Landouzy-Dejerine) muscular dystrophy, myotonic dystrophy, and Emery-Dreifuss muscular dystrophy. The symptoms of Duchenne muscular dystrophy, which occurs almost exclusively in males, include a waddling gait, toe walking, lordosis, frequent falls, and difficulty in standing up and climbing stairs. Symptoms start at about 3–7 years of age with most patients confined to a wheelchair by 10–12 years and many die at about 20 years of age due to respiratory complications. Current treatment for Duchenne muscular dystrophy includes administration of prednisone (a corticosteroid drug), which while not curative, slows the decline of muscle strength and delays disability. Corticosteroids, such as prednisone, are believed to act by blocking the immune cell activation and infiltration which are precipitated by muscle fiber damage resulting from the disease. Unfortunately, corticosteroid treatment also results in skeletal muscle atrophy which negates some of the potential benefit of blocking the immune response in these patients. Thus, there is a continuing need to identify therapeutic agents which slow the muscle fiber damage and delay the onset of disability in patients with muscular dystrophies, but cause a lesser degree of skeletal muscle atrophy than current therapies.

SUMMARY OF THE INVENTION

The present invention provides isolated peptides that are $CRF_2R$ agonists. Specifically, the invention provides an isolated peptide, or nucleic acid encoding the same, that are CRF, urocortin I, urocortin II, urocortin III, sauvagine, urotensin I or related peptide derivatives. The invention also provides for pharmaceutical composition comprising a safe and effective amount of an isolated peptide of the present invention and a pharmaceutically acceptable excipient. The invention further provides a kit comprising an isolated peptide in unit dose form and usage instructions.

The administration of a peptide, or nucleic acid encoding the same, pharmaceutical composition, or kit of the present invention, to a subject in need thereof, is effective for the treatment of $CRF_2R$ modulated disorders such as muscle atrophy or wasting. The invention also provides for an antibody that is specific to the peptides of the present invention. Lastly, the invention provides for the use of a peptide of the present invention, or nucleic acid encoding the same, in the manufacture of a medicament for the treatment of a $CRF_2R$ modulated disorder in a subject in need thereof.

The present invention encompasses isolated non-native peptides according to the Formula (I):

$$\text{alpha-beta-gamma-delta-epsilon-zeta-eta-theta} \qquad (I)$$

wherein:
(a) alpha comprises a sequence of a formula $X_1X_2X_3X_4X_5X_6$; wherein:
   $X_1$, $X_2$ and $X_3$ are each selected from the group consisting of nil, A, E, D G, N, P, Q, S, T, and Z;
   $X_4$ is selected from the group consisting of F, I, L, P, T, and V;
   $X_5$ is selected from the group consisting of A, I, P, S, T, and V;
   $X_6$ is selected from the group consisting of I, L, M, and N;
(b) beta comprises a sequence of a formula $SX_8DX_{10}$, wherein: $X_8$ and $X_{10}$ are each independently selected from the group consisting of I, L, and V;
(c) gamma comprises a sequence of a formula $X_{11}X_{12}X_{13}$; wherein: $X_{11}$ is selected from a group consisting of P, T, V, and S, and $X_{12}$ and $X_{13}$ are each independently selected from the group consisting of A, Naphthylalanine (Represented as B), C, D, E, F, G, H, I, K, L, M, N, P, Q, R, S, T, V, W, and Y;

(d) delta comprises a sequence of a formula $X_{14}X_{15}X_{16}$, wherein:
   $X_{14}$ is selected from the group consisting of I, L, and M;
   $X_{15}$ is selected from the group consisting of L and M; and
   $X_{16}$ is selected from the group consisting of S, N, Q, and R;
(e) epsilon comprises a sequence of a formula $X_{17}X_{18}X_{19}X_{20}X_{21}$, wherein:
   X17 is selected from the group consisting of V, I, L, T, K, E, N, and Q;
   X18 is selected from the group consisting of L, M, V, A, and T;
   $X_{19}$ is selected from the group consisting of I, F, L, and M;
   $X_{20}$ is selected from the group consisting of D, E, N, and H; and
   $X_{21}$ is selected from the group consisting of L, V, I, Q, M, and R;
(f) zeta comprises a sequence of a formula $X_{22}X_{23}X_{24}X_{25}$, wherein:
   $X_{22}$ is selected from the group consisting of nil, A, D, E, S, and T;
   $X_{23}$ is selected from the group consisting of nil, K, and R;
   $X_{24}$ is selected from the group consisting of nil, A H, M, N, Q, T, and Y;
   $X_{25}$ is selected from the group consisting of nil, E, D, I, K, N, Q, and R;
(g) eta comprises a sequence of the formula $X_{26}X_{27}X_{28}X_{29}X_{30}X_{31}$, wherein:
   $X_{26}$ is selected from the group consisting of A, D, G, H, K, N, Q, and S;
   $X_{27}$ is selected from the group consisting of A, E, I, L, M, and Q;
   $X_{28}$ is selected from the group consisting of A, H, K, Q, R, and V;
   $X_{29}$ is selected from the group consisting of A, E, K, N, M, and Q;
   $X_{30}$ is selected from the group consisting of H, K, N, Q, and R;
   $X_{31}$ is selected from the group consisting of A and K;
(h) theta comprises a sequence of the formula $X_{32}X_{33}NX_{35}X_{36}X_{37}X_{38}X_{39}X_{40}X_{41}$, wherein:
   $X_{32}$ is selected from the group consisting of A, E, H, and T;
   $X_{33}$ is selected from the group consisting of A, D, E, I, L, N, Q, R, S, and T;
   $X_{35}$ is selected from the group consisting of A and R;
   $X_{36}$ is selected from the group consisting of E, H, I, K, L, N, Q, and R;
   $X_{37}$ is selected from the group consisting of F, I, L, M, and Y;
   $X_{38}$ is selected from the group consisting of L, F, and M;
   $X_{39}$ is selected from the group consisting of A, D, E, N, and Q;
   $X_{40}$ is selected from the group consisting of A, D, E, H, I, K, N, Q, R, S, and T;
   $X_{41}$ is selected from the group consisting of A, F, I, and V; and variants thereof.

All documents cited are, in relevant part, incorporated herein by reference; the citation of any document is not to be construed as an admission that it is prior art with respect to the present invention.

SEQUENCE LISTING DESCRIPTION

Table 1 describes various proteins and protein fragment sequences that bind to CRF receptors. These selected sequences are included with the corresponding Genbank or Derwent accession number(s) and the animal species from which it is reported, as well as accession numbers for related nucleotide sequences that encode identical, or nearly identical, amino acid sequences. These known and novel sequences of the invention are further presented in the sequence listing.

TABLE 1

| Sequence Description | amino acid SEQ ID NO: | Species | Genbank (GB), Swiss-Prot (SP) or Derwent (D) Accession No. for nucleotide sequence | Related Genbank (GB) or Derwent (D) Accession Nos. |
|---|---|---|---|---|
| urocortin I fragment | 2 | *Homo sapiens* | Fragment of AF038633 (GB) amino acid residues 83–122 | AC109828 (GB) AX015619 (GB) AV708591 (GB) AV708591 (GB) AAZ35707 (D) AAT73432 (D) |
| urocortin II fragment | 4 | *Homo sapiens* | Fragment of AF320560 (GB) amino acid residues 72–109 | |
| urocortin III fragment | 6 | *Homo sapiens* | Fragment of AF361943 (GB) amino acid residue 118–157 | AY026949 (GB) |
| corticotropin releasing hormone fragment | 8 | *Homo sapiens* | Fragment of V00571 (GB) amino acid residues 154–194 | AC090195 (GB) AC090196 (GB) BC002599 (GB) AC021240 (GB) E00245 (GB) |
| corticotropin releasing factor fragment | 10 | Ovis sp. | E00212 (GB) | J00803 (GB) M22853 (GB) |
| sauvagine | 11 | *Phyllomedusa sauvagei* | P01144 (SP) | |

DESCRIPTION OF THE INVENTION

Glossary of Terms

The following is a list of definitions for terms used herein.

"Agonist" means any compound, including, but not limited to, antibodies, that activates a receptor. For example, CRFR agonists include, but are not limited to, CRF, urocortin, urocortin II, urocortin III, urotensin I, sauvagine and related analogs.

"Antibody", in its various grammatical forms, means immunoglobulin molecules and immunologically active portions of immunoglobulin molecules, i.e., molecules that contain an antigen binding site which specifically binds an antigen. As used herein, "isolated antibody," means an antibody which has been partially or completely separated from the proteins and naturally occurring organic molecules with which it is naturally associated.

"Binding affinity" means the propensity for a ligand to interact with a receptor and is inversely related to the dissociation constant for a specific CRF ligand-CRFR interaction. The dissociation constant can be measured directly via standard saturation, competition, or kinetics binding techniques or indirectly via pharmacological techniques involving functional assays and endpoints.

"Chimeric antibody" means an antibody that contains structural elements from two or more different antibody molecules, i.e., from different animal species. Chimeric antibodies include, but are not limited to, antibodies known as "humanized antibodies" which include, but are not limited to, chimeric antibodies generated by the technique known as complementarity determining region grafting.

"CRF" means corticotropin releasing factor which is the same as corticotropin releasing hormone (CRH). Exemplary CRF peptides include r/h CRF and ovine CRF (see U.S. Pat. No. 4,415,558), and the like.

"CRF analog" means substances which act as ligands of CRFRs. Suitable CRF analogs can be obtained from a variety of vertebrate species and include, but are not limited to, substances such as sauvagine (see, e.g., U.S. Pat. No. 4,605,642), urotensin (see, e.g., U.S. Pat. Nos. 4,908,352; and 4,533,654), mouse urocortin II, human urocortin-related peptide (Reyes, T. M. et al., *Proc. Nat'l Acad Sci* 98:2843–2848 (2001)), urocortin (see, e.g., WO 97/00063), human urocortin II (stresscopin related peptide), human urocortin III (stresscopin), pufferfish URP 1, pufferfish URP II, urotensin I, and the CRF analogs described in U.S. Pat. Nos. 4,415,558; 4,489,163; 4,594,329; 4,605,642; 5,109,111; 5,235,036; 5,278,146; 5,439,885; 5,493,006; 5,663,292; 5,824,771; 5,844,074; and 5,869,450. Specific CRF analogs include hUcnI (human urocortin I, AF038633 (GB)); hUroII (human urocortin II or stresscopin related peptide)(AF320560); hUroIII (human urocortin III or stresscopin, AF361943); hCRF (human corticotropin releasing factor)(V00571(GB)); oCRF (sheep corticotropin releasing factor E00212 (GB)); Svg (sauvagine, P01144 (SP)).

"CRFR agonist" means a compound or molecule which has the ability to activate $CRF_1R$, $CRF_2R$, or both.

"CRFR" means $CRF_1R$ or $CRF_2R$. The term "CRFR" also includes truncated and/or mutated proteins wherein regions of the receptor molecule not required for ligand binding or signaling have been deleted or modified.

"$CRF_1R$" means any isoforms of $CRF_1R$ from any animal species. The $CRF_1R$ has previously been referred to as CRF-RA, PC-CRF, CRF, (Perrin, M. H., et al. *Endocrinology* 133:3058–3061 (1993), Chen, R., et al. *Proc. Natl. Acad. Sci. USA* 90:8967–8971 (1993), Chang, C-P. et al., *Neuron* 11:1187–1195 (1993), Kishimoto, T., et al., *Proc. Natl. Acad. Sci. USA,* 92:1108–1112 (1995) and, Vita, N. et al., *FEBS Lett.* 335: 1–5 (1993)) or the CRH receptor.

The definition of $CRF_1R$ includes, but is not limited to, those receptors for which the cDNA or genomic sequence encoding the receptor has been deposited in a sequence database. These sequences include Accession Nos.: X72304, E11431, L23332, I92584, T37068, T28968, Q81952, L23333, NM_004382, AF180301, T28970, L25438, L24096, I92586, Q81954, AH006791, NM_007762, X72305, AF054582, Y14036, AF229359, AF229361, AB055434 and L41563. The nucleotide and protein sequences of these receptors are available from GenBank or Derwent.

"$CRF_2R$" means any isoform of $CRF_2R$ from any animal species. $CRF_2R$ has also been referred to as HM-CRF, CRF-RB, (Kishimoto, T., et al., *Proc. Natl. Acad. Sci. USA,* 92:1108–1112 (1995) and Perrin, M. et al. *Proc. Natl. Acad. Sci. USA* 92:2969–2973 (1995)).

The definition of $CRF_2R$ receptor includes, but is not limited to, those receptors for which the DNA sequence encoding the receptor has been deposited in a sequence database. These sequences include Accession Nos.: U34587, E12752, NM_001883, T12247, T66508, AF011406, AF019381, U16253, T12244, T28972, U17858, NM_009953, Y14037 and AF229360. The nucleotide and protein sequences of these receptors are available from GenBank or Derwent.

"Inhibit" means to partially or completely block a particular process or activity. For example, a compound inhibits skeletal muscle atrophy if it either completely or partially prevents muscle atrophy.

"Isolated peptide" means a peptide molecule is said to be "isolated" when physical, mechanical or chemical methods are employed to remove the peptide from cellular constituents that are normally associated with the protein. A skilled artisan can readily employ standard purification methods to obtain an isolated peptide.

"Isolated nucleic acid" means a nucleic acid molecule is substantially separated from contaminant nucleic acid molecules encoding other polypeptides. Purification and sequence identification techniques are well known in the art.

As used herein, two DNA sequences are said to be "operably associated" if the nature of the linkage between the two DNA sequences does not (1) result in the introduction of a frame-shift mutation, (2) interfere with the ability of a promoter region to direct the transcription of the coding sequences, or (3) interfere with the ability of the corresponding RNA transcript to be translated into a protein. For example, a coding sequence and regulatory sequences are operably associated when they are covalently linked in such a way as to place the transcription of the coding sequence under the influence or control of the regulatory sequences. Thus, a promoter region is operably associated with a coding sequence when the promoter region is capable of effecting transcription of that DNA sequence such that the resulting transcript is capable of being translated into the desired peptide.

"Selective agonist" means that the agonist generally has greater, preferably has significantly greater, activity toward a certain receptor(s) compared with other receptors, not that it is completely inactive with regard to other receptors.

"Sequence Identity" or "Homology" at the amino acid or nucleotide sequence level is determined by BLAST (Basic Local Alignment Search Tool) analysis using the algorithm employed by the programs blastp, blastn, blastx, tblastn and tblastx (Altschul et al. (1997) *Nucleic Acids Res.* 25, 3389–3402 and Karlin et al. (1990) *Proc. Natl. Acad. Sci. USA* 87, 2264–2268) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (1994) *Nature Genetics* 6, 119–129. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) *Proc. Natl. Acad. Sci. USA* 89, 10915–10919), recommended for query sequences over 85 nucleotides or amino acids in length.

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every wink$^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Skeletal muscle hypertrophy" means an increase in skeletal muscle mass or skeletal muscle function or both.

"Skeletal muscle atrophy" means the same as "muscle wasting" and means a decrease in skeletal muscle mass or skeletal muscle function or both.

In describing protein structure and function, reference is made to amino acids comprising the protein. The amino acids may also be referred to by their conventional abbreviations, as shown: A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; H=His=Histidine. The letter Z=Glx=Pyrrolidone carboxylic acid, is used to indicate N-terminal glutamic acid or glutamine that has formed an internal cyclic lactam. This has been described in the sequence listing under "MODIFED_RES" feature where appropriate. The letter B is used in the specification to designate Naphthylalanine, a modification of Alanine in certain peptides and has been indicated in the sequence listing under the "miscellaneous feature" in the sequence listing in the peptide sequences where it occurs. Abbreviation "Ac" has been used to indicate modified acetylated NH$_2$-terminus in the specification and has been described under the "MODIFIED_RES" feature where appropriate. The peptides of the invention are also modified to have amide group at the carboxy-terminus. This is indicated in the sequence listing under "MODIFIED_RES" feature. In order to designate a deletion or an absence of an amino acid in context of the natural homolog, a "–" or "nil" is used throughout the application.

Unless otherwise defined, all technical and scientific terms used herein have the same meaning as commonly understood by one of ordinary skill in the arts of protein chemistry, pharmacology, or molecular biology. The methods, materials and examples described herein are not intended to be limiting. Other methods and materials similar or equivalent to those described herein can be used in the practice or testing of the present invention.

Peptides

The present invention encompasses isolated non-native peptides according to the Formula (I):

$$\text{alpha-beta-gamma-delta-epsilon-zeta-eta-theta} \quad (I)$$

In Formula (I), alpha comprises a sequence of a formula $X_1X_2X_3X_4X_5X_6$; wherein: $X_1$, $X_2$ and $X_3$ are each selected from the group consisting of nil, A, E, D G, N, P, Q, R, S, T and Z; $X_4$ is selected from the group consisting of F, I, L, P, T, and V; $X_5$ is selected from the group consisting of A, I, P, S, T and V; and $X_6$ is selected from the group consisting of I, L, M, and N. In one aspect of the invention, alpha comprises a sequence of the formula $X_1X_2X_3X_4X_5X_6$; wherein $X_1$ is nil, $X_2$ is selected from the group consisting of D, E and Z; $X_3$ is selected from the group consisting of D, G and N; $X_4$ is selected from the group consisting of L and P; $X_5$ is selected from the group consisting of P and S; and $X_6$ is selected from the group consisting of I, L, M and N. In one embodiment, alpha further comprises the sequence selected from the group consisting of -EDLPL (SEQ ID NO: 388), -DNPSL (SEQ ID NO: 389), -DDPPL (SEQ ID NO: 390), -ZGPPI (SEQ ID NO: 391), ---PSL, and ---IVL, wherein "-" denotes nil. In another embodiment, alpha comprises the sequence -ZGPPI (SEQ ID NO: 391). In another embodiment, alpha comprises the sequence -DNPSL (SEQ ID NO: 389). In another embodiment, alpha comprises the sequence ---IVL. In another embodiment, alpha comprises the sequence ---PSL.

In another aspect of the invention, alpha comprises the formula $X_1X_2X_3X_4X_5X_6$; wherein $X_1$ is nil; $X_2$ is nil; $X_3$ is nil; $X_4$ is selected from the group consisting of F, I, L, P and V; $X_5$ is selected from the group consisting of A, I, S, T and V; $X_6$ is L. In one embodiment, alpha comprises a sequence selected from the group consisting of ---IVL, ---FTL, ---LTL, ---FAL, ---VIL, and ---PSL. In another embodiment, alpha comprises the sequence ---IVL.

In yet another aspect of the invention, alpha comprises a sequence selected from the group consisting of SQEPPI (SEQ ID NO: 392), SEEPPI (SEQ ID NO: 393), -DNPSL (SEQ ID NO: 389), ---IVL, -TKFTL (SEQ ID NO: 394), -ZGPPI (SEQ ID NO: 391), SQEIVL (SEQ ID NO: 395), SEEIVL (SEQ ID NO: 396), DNPIVL (SEQ ID NO: 397), TKIVL (SEQ ID NO: 398), ZGIVL (SEQ ID NO: 399), SDNPSL (SEQ ID NO: 401), STKFTL (SEQ ID NO: 402), SZGPPI (SEQ ID NO: 403), and NDDPPI (SEQ ID NO: 404).

In yet another aspect of the invention, alpha may be preceded by a polyhistidine (HHHHHH, SEQ ID NO: 400) or other peptide tag that may be useful in the purification or detection of the peptides of the invention.

In Formula (I), beta comprises a sequence of a formula $SX_8DX_{10}$, wherein $X_8$ and $X_{10}$ are each selected from the group consisting of I, L and V. In one embodiment, beta comprises the sequence selected from the group consisting of SIDL (SEQ ID NO: 405), SLDV (SEQ ID NO: 406), SLDL (SEQ ID NO: 407), SIDI (SEQ ID NO: 408), and SIDV (SEQ ID NO: 409). In another embodiment beta comprises the sequence further selected from the group consisting of SIDL (SEQ ID NO: 405) and SLDV (SEQ ID NO: 406). In yet another embodiment, beta comprises the sequence SIDL (SEQ ID NO: 405). In yet another embodiment, beta comprises the sequence SLDV (SEQ ID NO: 406). In yet another embodiment, beta comprises the sequence SIDV (SEQ ID NO: 409).

In Formula (I), gamma comprises a sequence of a formula $X_{11}X_{12}X_{13}$; wherein $X_{11}$ is P T, V, or S, and $X_{12}$ and $X_{13}$ are each selected from the group consisting of A, B (Naphthylalanine), C, D, E, F, G, H, I, K, L, M, N, P, Q, R, S, T, V, W, and Y. In one embodiment of the invention $X_{11}$ is P. In another embodiment, gamma comprises the sequence selected from the group consisting of PAB, PAF, PAH, PAQ, PAY, PFB, PFE, PFF, PFG, PFH, PFI, PFL, PFQ, PFV, PFW, PFY, PGY, PHB, PHF, PHH, PHQ, PHW, PHY, PIA, PIB, PID, PIE, PIF, PIG, PIH, PII, PIL, PIQ, PIR, PIT, PIV, PIW, PIY, PKY, PLB, PLE, PLF, PLG, PLH, PLI, PLL, PLQ, PLV, PLW, PLY, PNY, PQB, PQF, PQH, PQI, PQL, PQQ, PQV, PQW, PQY, PRY, PSY, PTB, PTE, PTF, PTH, PTI, PTL, PTV, PTW, PTY, PVB, PVY, PWF, PWH, PWQ, PWW, PWY, PYB, PYF, PYH, PYI, PYL, PYQ, PYT, PYV, PYW, PYY, SLE, SLG, SIG, and VIG. In yet another embodiment of the invention, gamma comprises the sequence selected from the group consisting of PFE, PFG, PFH, PFQ, PFY, PLE, PLG, PLH, PLQ, PLY, PTE, PTH, PTY, PIE, PIH, PIQ, PIY, PIG, PTN and PTS. In yet another embodiment, gamma comprises the sequence selected from the group consisting of PFE, PFG, PFH, PFQ, PFY, PLE, PLG, PLH, PLQ, PLY, PTE, PTH, PTY, PIE, PIH, PIQ, PIY, PYY, PFE, PTW, PQY, PHY, PII, PI, PTI, PTF, PTL, PIV, PIT, PTV and PIE. In yet another embodiment, gamma comprises the sequence selected from the group consisting of PIG, PTN, PTS, and PIG. In yet another embodiment, gamma comprises of sequence selected from PFQ, PYW, PLQ, PIG, PLY, PUY, PTY, PIG, PLL, PLF, and PFF. In yet another embodiment, gamma comprises the sequence PIG. In yet another embodiment, gamma comprises PFQ.

In Formula (I), delta comprises a sequence of a formula $X_{14}X_{15}X_{16}$, wherein $X_{14}$ is selected from the group consisting of I, L, and M; $X_{15}$ is selected from the group consisting of L and M; and $X_{16}$ is selected from the group consisting of S, N, Q, and R. In one embodiment, delta comprises a sequence selected from the group consisting of ILS, IMN, LLQ, LLR, and MLR. In one embodiment, delta comprises the sequence LLQ or LLR.

In Formula (I), epsilon comprises a sequence of a formula $X_{17}X_{18}X_{19}X_{20}X_{21}$, wherein, $X_{17}$ is selected from the group consisting of V, I, L, T, K, E, N, and Q; $X_{18}$ is selected from the group consisting of L, M, V, A, and T; $X_{19}$ is selected from the group consisting of I, F, L, and M; $X_{20}$ is selected from the group consisting of D, E, N, and H; and $X_{21}$ is selected from the group consisting of L, V, I, Q, M, and R. In one embodiment, epsilon comprises a sequence selected from the group consisting of VLIDL (SEQ ID NO: 410), VLFDV (SEQ ID NO: 411), VLIEI (SEQ ID NO: 412), ILFNI (SEQ ID NO: 413), LLIEI (SEQ ID NO: 414), LLFNI (SEQ ID NO: 415), ILLEQ (SEQ ID NO: 416), ILIEI (SEQ ID NO: 417), ILLEI (SEQ ID NO: 418), TLLEL (SEQ ID NO: 419), KMIEI (SEQ ID NO: 420), KVIEI (SEQ ID NO: 421), EVLEM (SEQ ID NO: 422), EMIEI (SEQ ID NO: 423), EVIEI (SEQ ID NO: 424), EAIEI (SEQ ID NO: 425), ETIEI (SEQ ID NO: 426), EIIEI (SEQ ID NO: 427), ELIEI (SEQ ID NO: 428), NMIEM (SEQ ID NO: 429), NMIHR (SEQ ID NO: 430), NMIHM (SEQ ID NO: 431), QMMEM (SEQ ID NO: 432), and LLFNI (SEQ ID NO: 433). In one embodiment of the invention, epsilon comprises the sequence selected from the group consisting of VLIDL (SEQ ID NO: 410), VLFDV (SEQ ID NO: 411), ILFNI (SEQ ID NO: 413), LLFNI (SEQ ID NO: 415), ILLEQ (SEQ ID NO: 416), TLLEL (SEQ ID NO: 419) and KMIEI (SEQ ID NO: 420). In another embodiment, epsilon comprises the sequence selected from the group consisting of VLIDL (SEQ ID NO: 410), VLFDV (SEQ ID NO: 411), ILFNI (SEQ ID NO: 413) and ILLEQ (SEQ ID NO: 416). In yet another embodiment, epsilon comprises the sequence selected from the group consisting of KMIEI (SEQ ID NO: 420) or ILLEQ (SEQ ID NO: 416). In yet another embodiment, epsilon comprises the sequence KVIEI (SEQ ID NO: 421), KMIEI (SEQ ID) NO: 420), ILLEI (SEQ ID NO: 417), ILLEQ (SEQ ID NO: 416), or TLLEL (SEQ ID NO: 419). In yet another embodiment, epsilon comprises the sequence KMIEI (SEQ ID NO: 420). In yet another embodiment, epsilon comprises the sequence ILLEQ (SEQ ID NO: 416).

In Formula (I), zeta comprises a sequence of a formula $X_{22}X_{23}X_{24}X_{25}$, wherein $X_{22}$ is selected from the group consisting of nil, A, D, E, S and T; $X_{23}$ is selected from the group consisting of nil, K and R; $X_{24}$ is selected from the group consisting of nil, A H, M, N, Q, T and Y; and $X_{25}$ is selected from the group consisting of nil, E, D, I, K, N, Q and R. In one embodiment of the invention, zeta comprises a sequence of the formula $X_{22}X_{23}X_{24}X_{25}$; wherein $X_{22}$ is selected from the group consisting of nil, D and E; $X_{23}$ is selected from the group consisting of nil, K and R; $X_{24}$ is selected from the group consisting of nil, A H, M, N, Q, T and Y; $X_{25}$ is selected from the group consisting of nil, E, D, I, K, N, Q and R. In another embodiment, zeta comprises a sequence selected from the group consisting of SRAE (SEQ ID NO: 434), EKAR (SEQ ID NO: 435), ERAR (SEQ ID NO: 436), EKQE (SEQ ID NO: 437), TKDR (SEQ ID NO: 438), TKAD (SEQ ID NO: 439), AKAR (SEQ ID NO: 440), AKQR (SEQ ID NO: 441), ERQR (SEQ ID NO: 442), AKAE (SEQ ID NO: 443), ERAE (SEQ ID NO: 444), ARQR (SEQ ID NO: 445), EKQR (SEQ ID NO: 446), TKAN (SEQ ID NO: 447), TKAR (SEQ ID NO: 448), EAAR (SEQ ID NO: 449), ERQE (SEQ ID NO: 450), ARAD (SEQ ID NO: 451), EKTQ (SEQ ID NO: 452), ARAR (SEQ ID NO: 453), ARAE (SEQ ID NO: 454), ARQE (SEQ ID NO: 455), AKQE (SEQ ID NO: 456), TRAD (SEQ ID NO: 457), AKAD (SEQ ID NO: 458), TRAR (SEQ ID NO: 459), EKQQ (SEQ ID NO: 520), --RR, --AA, -AAR, ---R, -RAR, ---A, --AR, -ARA, -R-R, A-AR, A- A-, A---, ARA- and ---. In yet another embodiment, zeta comprises a sequence selected from the group consisting of EKAR (SEO ID NO: 435), ERAR (SEQ ID NO: 436), EKQE (SEQ ID NO: 437) and TKDR (SEQ ID NO: 438). In yet another embodiment, zeta comprises EKQE (SEQ ID NO: 437), EKTQ (SEQ ID NO: 452), ARAR (SEQ ID NO: 453), or EKAR (SEQ ID NO: 435).

In Formula (I), eta comprises a sequence of a formula $X_{26}X_{27}X_{28}X_{29}$ $X_{30}X_{31}$, wherein: $X_{26}$ is selected from the group consisting of A, D, G, H, K, N, Q, and S; $X_{27}$ is selected from the group consisting of A, E, I, L, M and Q; $X_{28}$ is selected from the group consisting of A, H, K, Q, R and V; $X_{29}$ is selected from the group consisting of A, E, K, M, N and Q; $X_{30}$ is selected from the group consisting of H, K, N, Q and R; and $X_{31}$ is selected from the group consisting of A and K. In one embodiment of the invention, eta comprises a sequence selected from the group consisting of AAREQA (SEQ ID NO: 460); KEKKRK (SEQ ID NO: 461); SQRERA (SEQ ID NO: 462), KEKQQA (SEQ ID NO: 463), and QLAQQA (SEQ ID NO: 464) AARNQA (SEQ ID NO: 521), KERNQA (SEQ ID NO: 522), KEKNQA (SEQ ID NO: 523), KQRERA (SEQ ID NO: 524), KERERA (SEQ ID NO: 525), KEKERA (SEQ ID NO: 526), KEKQRA (SEQ ID NO: 527), AEAAAK (SEQ ID NO: 528), AAHAAA (SEQ ID NO: 529), and HAHAHA (SEQ ID NO: 530). In yet another embodiment, eta comprises a sequence selected from the group consisting of AAREQA (SEQ ID NO: 460), and KEKKRK (SEQ ID NO: 461). In yet still another embodiment, eta comprises the sequence AAREQA (SEQ ID NO: 460). In yet still another embodiment, eta comprises a sequence selected from the group consisting of SQRERA (SEQ ID NO: 462) and KEKQQA (SEQ ID NO: 463). In yet another embodiment, eta comprises the sequence KEKQQA (SEQ ID NO: 463).

In Formula (I), theta comprises a sequence of the formula $X_{32}X_{33}NX_{35}X_{36}X_{37}X_{38}X_{39}X_{40}X_{41}$, wherein $X_{32}$ is selected from the group consisting of A, E, H and T; $X_{33}$ is selected from the group consisting of A, D, E, I, L, N, Q, R, S and T; $X_{35}$, is selected from the group consisting of A and R; $X_{36}$ is selected from the group consisting of E, H, I, K, L, N, Q and R; $X_{37}$ is selected from the group consisting of F, I, L, M and Y; $X_{38}$ is selected from the group consisting of L, F and M; $X_{39}$ is selected from the group consisting of A, D, E, N and Q; $X_{40}$ is selected from the group consisting of A, D, E, H, I, K, N, Q, R, S and T; $X_{41}$ is selected from the group consisting of A, F, I and V. In one embodiment of the invention, theta comprises a sequence of the formula $X_{32}X_{33}NX_{35}X_{36}X_{37}X_{38}X_{39}X_{40}X_{41}$, wherein $X_{32}$ is selected from the group consisting of A, E and T; $X_{33}$ is selected from the group consisting of A, D, E, N, Q, S and T; $X_{35}$ is selected from the group consisting of A and R; $X_{36}$ is selected from the group consisting of H, I, L, N, Q and R; $X_{37}$ is selected from the group consisting of F, I, L, M, and Y; $X_{38}$ is selected from the group consisting of L, F and M; $X_{39}$ is selected from the group consisting of A, D, E, N and Q; $X_{40}$ is selected from the group consisting of nil, A, D, H, Q, R, S and T; $X_{41}$ is selected from the group consisting of I and V. In another embodiment, theta comprises a sequence selected from the group consisting of AANRLLLDTV (SEQ ID NO: 465), AAQEQILAHV (SEQ ID NO: 466), ANNAELLAEI (SEQ ID NO: 467), ANNAHLLAHI (SEQ ID NO: 468), ANNAKLLAKI (SEQ ID NO: 469), ANNALLLATI (SEQ ID NO: 470), ANNALLLDTI (SEQ ID NO: 471), ANNANLLANI (SEQ ID NO: 472), ANNAQLLAHI (SEQ ID NO: 473), ANNAQLLAQI (SEQ ID NO: 474), ANNARILARV (SEQ ID NO: 475), ANNARLLARI (SEQ ID NO: 476), ANNARLLDTI (SEQ ID NO: 477), ANNRLLLATI (SEQ ID NO: 478), ANNRLLLDTI (SEQ ID NO: 479), EQNAHIFAHV (SEQ ID NO: 480), EQNAQIFAHV (SEQ ID NO: 481), EQNARIFARV (SEQ ID NO: 482), EQNRIIFDSV (SEQ ID NO: 483), ETNARILARV (SEQ ID NO: 484), HAQAHILAHV (SEQ ID NO: 485), HSNRKIIDIA (SEQ ID NO: 486), HSNRKLLDIA (SEQ ID NO: 487), HSNRKLMEII (SEQ ID NO: 488), HTNARILARV (SEQ ID NO: 489), TNNRLLLATV (SEQ ID NO: 490), TNNRLLLDTI (SEQ ID NO: 491), TSNRKLMEII (SEQ ID NO: 492), TTNARILARN (SEQ ID NO: 493), TTNARILARV (SEQ ID NO: 494), TTNARLLATV (SEQ ID NO: 495), TTNARLLDRV (SEQ ID NO: 496), TTNARLLDTV (SEQ ID NO: 497), TTNRLLLARV (SEQ ID NO: 498), TTNRLLLATV (SEQ ID NO: 499), TTNRLLLDTV (SEQ ID NO: 500), TTQARILARV (SEQ ID NO: 501), and TTVARILARV (SEQ ID NO: 502). In yet another embodiment, theta comprises a sequence selected from the group consisting of TTNARILARV (SEQ ID NO: 494), ANNALLLDTI (SEQ ID NO: 471), ANNALLLATI (SEQ ID NO: 470), TTNARLLDTV (SEQ ID NO: 497) and TTNARLLDRV (SEQ ID NO: 496). In yet another embodiment, theta comprises the sequence ANNARLLDTI (SEQ ID NO: 477), ANNARLLARI (SEQ ID NO: 476), ANNALLLDTI (SEQ ID NO: 471), ANNALLLATI (SEQ ID NO: 470), TTNARLLDRV (SEQ ID NO: 496), TTNARILARV (SEQ ID NO: 494), ANNRLLLDTI (SEQ ID NO: 479), EQNARIFARV (SEQ ID NO: 482), EQNAHIFAHV (SEQ ID NO: 480), and EQNAQIFAHV (SEQ ID NO: 481). One skilled in the art will readily appreciate that theta encompasses the C-terminus end of the peptide.

In one embodiment, the invention comprises a non-native peptide comprising the sequence:

ZGPPISIDLPX$_{11}$X$_{12}$LLRKX$_{17}$IEIEKQEKEKQQAX$_{31}$X$_{32}$NAX$_{35}$X$_{36}$LX$_{38}$X$_{39}$X$_{40}$ (SEQ ID NO: 531), wherein: $X_{11}$ is selected from F, Y, L, I, and T; $X_{12}$ is selected from Q, W, and Y; $X_{17}$ is selected from V and M; $X_{31}$ is selected from T and A; $X_{32}$ is selected from N and T; $X_{35}$ is selected from R and L; $X_{36}$ is selected from L and I; $X_{38}$ is selected from D and A; $X_{39}$ is selected from T and R; $X_{40}$ is selected from I and V; and variants thereof having at least about 95% sequence identity to said peptide.

The peptides of the invention have also been described as a peptide of 41 amino acids with certain preferred sequences. Following peptide strings have been specifically exemplified: ZGPPISIDLP (SEQ ID NO: 503) for residues $X_2$–$X_{11}$, LLRK (SEQ ID NO: 504) for residues $X_{14}$–$X_{17}$, IEIEKQEKEKQQA (SEQ ID NO: 505) for residues $X_{19}$–$X_{31}$, PSLSID (SEQ ID NO: 506) for residues $X_4$–$X_9$, and LLRTLLELEKTQSQRERAEQNA (SEQ ID NO: 507) for residues $X_{14}$–$_{35}$.

Variants of the disclosed peptides, and nucleotide sequences encoding the same, are also encompassed by the present invention. As used herein, "variants," means those peptides, polypeptides or proteins, or nucleotide sequences encoding the same, that are substantially similar to those peptides described by Formula (I) and which may be used as CRF$_2$R agonists. A peptide of Formula (I) may be altered in various ways to yield a variant of those encompassed by the present invention including amino acid substitutions, deletions, truncations, insertions, and modifications. Methods for such manipulations are generally known in the art. For example, variants can be prepared by mutations in the nucleotide sequences encoding the same. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. In one embodiment of the variant, the substitution(s) of the peptide of Formula (I) is conservative in that it minimally disrupts the biochemical properties of the variant. Thus, where mutations are introduced to substitute amino acid residues, positively charged residues (H, K, and R) preferably are substituted with positively charged residues; negatively charged residues (D and E) preferably are substituted with negatively-charged residues; and neutral non-polar residues (A, F, I, L, M, P, V, and W) preferably are substituted with neutral non-polar residues. In another embodiment of the variant, the overall charge, structure or hydrophobic/hydrophilic properties of the peptide can be altered without substantially adversely affecting CRF$_2$R agonism. In still another embodiment, the variant is an active fragment of a peptide of Formula (I). In yet another embodiment of a variant, a peptide of Formula (I) is modified by acetylation, carboxylation, phosphorylation, glycosylation, ubiquitination, and labeling, whether accomplished by in vivo or in vitro enzymatic treatment of the protein or by the synthesis of the peptide using modified amino acids. Common non-limiting examples of modifications to amino acids include phosphorylation of tyrosine, serine, and threonine residues; methylation of lysine residue; acetylation of lysine residues; hydroxylation of proline and lysine residues; carboxylation of glutamic acid residues; glycosylation of serine, threonine, or asparagine residues; and ubiquitination of lysine residues. The variant can also include other domains, such as epitope tags and His tags (e.g., the peptide can be a fusion protein).

In yet another embodiment, peptide mimics of a peptide of Formula (I) are encompassed within the meaning of variant. As used herein, "mimic," means an amino acid or an amino acid analog that has the same or similar function characteristics of an amino acid. Thus, for example, an arginine analog can be a mimic of arginine if the analog contains a side chain having a positive charge at physiologic pH, as is characteristic of the guanidinium side chain reactive group of arginine. Examples of organic molecules that can be suitable mimics are listed at Table 1 of U.S. Pat. No. 5,807,819. Generally, a variant, or nucleic acid sequence encoding the same, of the present invention will have at least 70%, generally, 80%, preferably up to 90%, more preferably 95%, even more preferably 97%, still even more preferably 98%, and most preferably 99% sequence identity to its respective native amino acid sequence. Fusion proteins, or N-terminal, C-terminal or internal extensions, deletions, or insertions into the peptide sequence shall not be construed as affecting homology.

Use of the Peptides of the Invention as $CRF_2R$ Agonists

The peptides of the invention are useful for the treatment of a variety of diseases, disorders, and conditions that are modulated by $CRF_2R$ or by $CRF_2R$ activity. As used herein, the terms "disease," disorder" and "condition" are used interchangeably. As used herein, a disorder described by the terms "modulated by $CRF_2R$," or "modulated by $CRF_2R$ activity" refers to a disorder, condition or disease where $CRF_2R$ activity is an effective means of alleviating the disorder or one or more of the biological manifestations of the disease or disorder; or interferes with one or points in the biological cascade either leading to the disorder or responsible for the underlying disorder; or alleviates one or more symptoms of the disorder. Thus, disorders subject to "modulation" include those for which: (1) The lack of $CRF_2R$ activity is a "cause" of this disorder or one or more of the biological manifestations, whether the activity was altered genetically, by infection, by irritation, by internal stimulus or by some other cause; (2) The disease or disorder or the observable manifestation or manifestations of the disease or disorder are alleviated by $CRF_2R$ activity (the lack of $CRF_2R$ activity need not be causally related to the disease or disorder or the observable manifestations thereof); (3) $CRF_2R$ activity interferes with part of the biochemical or cellular cascade that results in or relates to the disease or disorder. In this respect, the $CRF_2R$ activity alters the cascade, and thus controls the disease, condition, or disorder.

In one embodiment of the invention, the peptides of the present invention have none or only weak $CRF_1R$ agonist activity. Thus, the peptides of the present invention are particularly useful for the treatment of $CRF_2R$ modulated disorders. One such $CRF_2R$ modulated disorder is skeletal muscle atrophy. Skeletal muscle atrophy may be induced by disuse due to surgery, bed rest, broken bones; denervation/nerve damage due to spinal cord injury; autoimmune disease; infectious disease; glucocorticoid use for unrelated conditions; sepsis due to infection or other causes; nutrient limitation due to illness or starvation; cancer cachexia; chronic inflammation; acquired immunodeficiency syndrome (AIDS) cachexia; chronic obstructive pulmonary disease (COPD); congestive heart failure; sarcopenia and genetic disorders; e.g., muscular dystrophies, neurodegenerative diseases.

In another embodiment, the treatment of a $CRF_2R$ modulated disorder results in an increase of skeletal mass and function. Diseases and conditions affecting skeletal muscle mass and function include, but not limited to, skeletal muscle atrophy or wasting including acute atrophy/wasting resulting from disuse due to illness, surgery, bed rest or accident; nerve damage due to spinal cord injury, autoimmune disease, or infectious disease; glucocorticoid use for unrelated conditions; sepsis due to infection or other causes; nutrient limitation due to illness or starvation; and space travel: and chronic atrophy/wasting including cancer cachexia, chronic inflammation, AIDS cachexia, COPD, congestive heart failure, genetic disorders, e.g., muscular dystrophies, neurodegenerative diseases and sarcopenia (age associated muscle loss).

In yet another embodiment, the treatment of a $CRF_2R$ modulated disorder includes disorders affecting bone. Diseases and conditions affecting bone include, but not limited to, bone loss resulting from disuse due to illness, surgery, bed rest or accident; nerve damage due to spinal cord injury, autoimmune disease, or infectious disease; glucocorticoid use for unrelated conditions; sepsis due to infection or other causes; nutrient limitation due to illness or starvation; and space travel. Age and hormone related bone loss (osteoporosis) are also included.

In yet another embodiment, the treatment of a $CRF_2R$ modulated disorder includes disorders affecting the heart and circulatory system including but not limited to hypertension, congestive heart failure, damage to the heart resulting from heart attack, ischemia reperfusion injury, stroke, migraine, memory loss, Alzheimer's disease, dementia, and the like.

In yet another embodiment, the treatment of a $CRF_2R$ modulated disorder includes disorder affecting the joints including but not limited to arthritis in particular osteoarthritis and rheumatoid arthritis.

In yet another embodiment, the treatment of a $CRF_2R$ modulated disorder includes metabolic diseases including obesity and diabetes.

In yet another embodiment, the treatment of a CRF2R modulated disorder includes: pain reduction; swelling reduction; allergic reactions, allergy; reducing body temperature; suppressing appetite; congestive heart failure; stress and anxiety; altering undesirably low levels of adrenocorticotropic hormone ("ACTH") secretion; controlling appetite, arousal, and cognitive functions; and preventing long term effects of stress, such as anxiety disorders, anorexia nervosa and melancholic depression.

The term "treatment" is herein to mean that, at a minimum, administration of a peptide of the present invention that mitigates a $CRF_2R$ modulated disorder in a mammalian subject, preferably in humans. Thus, the term "treatment" includes: preventing a $CRF_2R$ modulated disorder from occurring in a mammal, particularly when the mammal is predisposed to acquiring the $CRF_2R$ modulated disorder, but has not yet been diagnosed with the disease; inhibiting the $CRF_2R$ modulated disorder; and/or alleviating or reversing the $CRF_2R$ modulated disorder. Insofar as the methods of the present invention are directed to preventing the $CRF_2R$ modulated disorder, it is understood that the term "prevent" does not require that the $CRF_2R$ modulated disorder be completely thwarted (see Webster's Ninth Collegiate Dictionary). Rather, as used herein, the term "preventing" refers to the ability of the skilled artisan to identify a population that is susceptible to $CRF_2R$ modulated disorders, such that administration of the peptides and kits of the present invention may occur prior to the onset of the symptoms of the $CRF_2R$ modulated disorder. The population that is at risk for a particular $CRF_2R$ modulated disorder is readily identifiable. For example, the population that is at risk for developing muscular dystrophy can be determined by identifying mutations in genes characteristic of the disorder. For example, and previously discussed, Duchenne and Becker dystrophies results from the inheritance of a mutation in the dystrophy gene, which is located at the Xp21 locus. Those individuals of a population that possess these mutations are at risk of developing muscular dystrophy. Thus, the patient population is identifiable and could receive the administration of a composition or unit dose form of a kit of the present invention before progression of the disease. Thus, progression of muscular atrophy or wasting in such individuals would be "prevented."

Nucleic Acid Molecules

The present invention further provides nucleic acid molecules that encode the peptides of Formula (I) and variants thereof, preferably in isolated form. As used herein, "nucleic acid" is defined as RNA or DNA that encodes a peptide of the present invention as defined above, or is complementary to a nucleic acid sequence encoding such peptides. Specifically contemplated are genomic DNA, cDNA, mRNA and antisense molecules, as well as nucleic acids based on alternative backbones or including alternative bases whether derived from natural sources or synthesized.

The present invention further provides a fragment of an encoding nucleic acid molecule. As used herein, a fragment of an encoding nucleic acid molecule refers to a small portion of the entire protein coding sequence. The size of the fragment will be determined by the intended use. For example, if the fragment is chosen so as to encode an active portion of a peptide of the present invention, the fragment will need to be large enough to encode the functional regions of the peptide.

Fragments of the encoding nucleic acid molecules of the present invention (i.e., synthetic oligonucleotides) that are used as probes or specific primers for the polymerase chain reaction (PCR), or to synthesize gene sequences encoding peptides of the invention, can easily be synthesized by chemical techniques, for example, the phosphotriester method of Matteucci et al., *J. Am. Chem. Soc.*, 103:3185–3191 (1981) or using automated synthesis methods. In addition, larger DNA segments can readily be prepared by well-known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can readily employ any such label to obtain labeled variants of the nucleic acid molecules of the invention. Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

Preparation of Peptides or Cell Lines Expressing Peptides

The peptides of the present invention can be prepared for a variety of uses, including, but not limited to, use as pharmaceutical reagents for the treatment of $CRF_2R$ modulated disorders. It will be clear to one of skill in the art that, for certain embodiments of the invention, purified peptides will be most useful, while for other embodiments cell lines expressing the peptides will be most useful.

Because the peptides of Formula (I) are short polypeptides, the skilled artisan will recognize that peptides of the present invention may be synthesized by direct synthesis, rather than by recombinant means, using techniques well known in the art. See Bodanszky, *Principles of Peptide Synthesis*, Springer-Verlag, Heidelberg (1984); and such as via solid-phase synthesis, see, e.g., Merrifield, *J. Am. Chem. Soc.*, 85:2149–54 (1963); Barany et al., *Int. J. Peptide Protein Res.*, 30:705–739 (1987); and U.S. Pat. No. 5,424,398.

For example, the peptides can be synthesized with either an Applied Biosystem, Inc. (ABI) Model 433 automated synthesizer or a multi-reactor synthesizer (model Symphony™) from Protein Technology, Inc (PTI). As to peptides synthesized with the ABI synthesizer, all reagents are purchased from ABI (except piperidine which is purchased from Aldrich). Fmoc amino acids are purchased from ABI (except Fmoc-L-Pyr which is purchased from Chem-Impek). Rink Amide resins are purchased from Nova Chemicals. Standard 0.1 mmole FastMoc chemistry with single coupling is used. The general Fmoc chemistry protocol for SPPS (solid phase peptide synthesis) includes: 1) cleavage of the Fmoc protection groups with piperidine; 2) activation of the carboxyl group of amino acids; and 3) coupling the activated amino acids to the amino-terminal of the resin bound peptide chain to form peptide bonds. Amino acids are activated with 2-(1H-benzotriazol-1-yl)-1,1,3,3-tetramethyluronium hexafluorophosphate (HBTU). A dry protected amino acid in a cartridge (1.0 mmol) is dissolved in a solution of HBTU, N,N-diisopropylethylamine (DIEA), and 1-hydroxybenzotriazole (HOBt) in N,N-dimethylformamide (DMF) with additional N-methylpyrrolidone (NMP) added. The activated Fmoc amino acid is formed almost instantaneously and the solution is transferred directly to the reaction vessel. The step of Fmoc deprotection is monitored and controlled by conductivity measurement. The peptide chain is built on a Rink Amide resin since the C-terminal amide is needed. The final product is washed extensively with NMP and dichloromethane (DCM).

As to peptides synthesized with the PTI multiple synthesizer, all the Fmoc amino acids are purchased from Nova-Biochem (except Fmoc-Pyr which is purchased from Chem-Impex). Standard 0.05 mmole Fmoc synthesis protocols are used for syntheses. Fmoc amino acids (0.4 mmol) are dissolved in a solution of HBTU (200 mM), N-methylmorpholine (NMM, 0.4 M) and N,N-dimethylformamide (DMF) with additional N-methylpyrrolidone (NMP) added. The activated Fmoc amino acid is formed almost instantaneously and the solution is transferred directly to the reaction vessel. The step of Fmoc deprotection is conducted twice. The peptide chain is built on a Rink Amide resin since the C-terminal amide is needed. The final synthesis product is washed extensively with NMP and dichloromethane (DCM).

The newly synthesized peptides are deprotected. The resins containing synthesized peptides are unloaded from the synthesizer and briefly air-dried. Using 1.5–2.0 ml of the cleavage cocktail (comprising 95% trifluoroacetic acid (TFA), 2.5% ethanodithiol, 2.5% thioanisol, 2.5% phenol (W/V) in water) for 4 hours at room temperature, the peptides are cleaved off the resin and at the same time, the side chain protection groups [O-t-butyl (OtBu) for Asp, Glu, Tyr, Thr and Ser; Pentamethylchroman-6-sulfonyl (Pmc) for Arg, t-butoxycarbonyl (Boc) for Trp and Lys; trityl (Trt) for His, Asn and Gln] are removed under the deprotection condition. The cleavage solution is separated from the resin by filtration. The filtrate is then diluted with 15 ml of water. Six rounds of ether extraction are performed to clean the peptide product. The peptide is lyophilized and stored at −20° C. before purification.

The deprotected peptides are purified and characterized. The peptide powder is dissolved in 50% acetic acid solution and injected onto a Vydac 1.0 cm I.D. 25 cm length C-8 column with 5 µm particle size, and 300 Å pore size for purification. A Beckman System Gold high performance liquid chromatography (HPLC) system with dual wavelength (220 nm and 280 nm) ultraviolet detector is used. A linear gradient of acetonitrile is programmed and introduced to the column to separate the peptide product from other substances. The elute is collected by a Pharmacia fraction collector, and the individual separation fractions were subjected to both analytical HPLC and (matrix assisted laser desorption ionization time of flight mass spectroscopy) MALDI-TOF MS for characterization to ensure the identity and purity.

The use of recombinant DNA technology in the preparation of the peptides, or of cell lines expressing these peptides, is also contemplated. Such recombinant methods are well known in the art. Methods for generating rDNA molecules are well known in the art, for example, see Sambrook et al., *Molecular Cloning—A Laboratory Manual*, Cold Spring Harbor Laboratory Press (1989). To express recombinant peptides of the present invention, an expression vector that comprises a nucleic acid which encodes the polypeptide of interest under the control of one or more regulatory elements, is prepared. The sequence of nucleic acids encoding the peptides of the present invention can be deduced from the peptide sequences discussed or claimed herein.

By methods well known in the art, the isolated nucleic acid molecule encoding the peptide of interest may be ligated into a suitable expression vector. The host-expression vector systems that may be used for purposes of the invention include, but are not limited to: microorganisms such as bacteria (e.g., *E. coli, B. subtilis*) transformed with recombinant bacteriophage DNA, plasmid DNA, or cosmid DNA expression vectors containing nucleotide sequences encoding the peptides of the present invention; yeast (e.g., *Saccharomyces, Pichia*) transformed with recombinant yeast expression vectors containing nucleotide sequences encoding the peptides of the present invention; insect cell systems infected with recombinant virus expression vectors (e.g., baculovirus) containing nucleotide sequences encoding the peptides of the present invention; plant cell systems infected with recombinant virus expression vectors (e.g., cauliflower mosaic virus, tobacco mosaic virus) or transformed with recombinant plasmid expression vectors (e.g., Ti plasmid) containing nucleotide sequences encoding the peptides of the present invention; or mammalian cell systems (e.g., COS, CHO, HEK293, NIH3T3) harboring recombinant expression constructs containing promoters derived from the genome of mammalian cells (e.g., metallothionein promoter) or from mammalian viruses (e.g., retrovirus LTR) and also containing nucleotide sequences encoding the peptides of the present invention.

In bacterial systems, a number of expression vectors may be advantageously selected depending upon the use intended for the peptide being expressed. For example, when a large quantity of such protein is needed, vectors which direct the expression of high levels of protein products are desirable. One skilled in the art is able to generate such vector constructs and purify the proteins by a variety of methodologies including selective purification technologies such as fusion protein selective columns and antibody columns, and non-selective purification technologies.

In an insect protein expression system, the baculovirus *A. californica* nuclear polyhedrosis virus (AcNPV), is used as a vector to express foreign genes in *S. frugiperda* cells. In this case, nucleotide sequences encoding the peptides of the present invention are cloned into non-essential regions of the virus and placed under the control of an AcNPV promoter. The recombinant viruses are then used to infect cells in which the inserted gene is expressed and the protein is purified by one of many techniques known to one skilled in the art.

In mammalian host cells, a number of viral-based expression systems may be utilized. Utilization of these expression systems often requires the creation of specific initiation signals in the vectors for efficient translation of the inserted nucleotide sequences. This is particularly important if a portion of the nucleotide sequence used does not contain the endogenous initiation signal. The placement of this initiation signal, in frame with the coding region of the inserted nucleotide sequence, as well as the addition of transcription and translation enhancing elements and the purification of the recombinant protein, are achieved by one of many methodologies known to one skilled in the art. Also important in mammalian host cells is the selection of an appropriate cell type which is capable of the necessary post translational modifications of the recombinant protein. Such modifications, for example, cleavage, phosphorylation, glycosylation, acetylation, etc., require the selection of the appropriate host cell which contains the modifying enzymes. Such host cells include, but are not limited to, CHO, HEK293, NIH3T3, COS, etc. and are known by those skilled in the art.

For long term, high expression of recombinant proteins, stable expression is preferred. For example, cell lines that stably express peptides of the present invention may be engineered. One of skill in the art, following known methods such as electroporation, calcium phosphate transfection, or liposome-mediated transfection, can generate a cell line that stably expresses the peptides of the present invention. This is usually accomplished by transfecting cells using expression vectors which contain appropriate expression control elements (e.g., promoter sequences, enhancer sequences, transcriptional termination sequences, polyadenylation sites, translational start sites, etc.), a selectable marker, and the gene of interest. The selectable marker may either be contained within the same vector, as the gene of interest, or on a separate vector, which is co-transfected with the peptide encoding sequence-containing vector. The selectable marker in the expression vector may confer resistance to the selection and allows cells to stably integrate the vector into their chromosomes and to grow to form foci which in turn can be cloned and expanded into cell lines. Alternatively, the expression vector may allow selection of the cell expressing the selectable marker utilizing a physical attribute of the marker, i.e., expression of Green Fluorescent Protein (GFP) allows for selection of cells expressing the marker using fluorescence activated cell sorting (FACS) analysis.

One of skill in the art is able to select an appropriate cell type for transfection in order to allow for selection of cells into which the sequence of interest has been successfully integrated. For example, where the selectable marker is herpes simplex virus thymidine kinase, hypoxanthine-guanine phosphoribosyltransferase or adenine phosphoribosyltransferase, the appropriate cell type would be tk-, hgprt- or aprt-cells, respectively. Or, normal cells can be used where the selectable marker is dhfr, gpt, neo or hygro which confer resistance to methotrexate, mycophenolic acid, G-418 or hygromycin, respectively.

Preparation of Antibodies

Antibodies that selectively recognize one or more epitopes of the peptides of the present invention are also encompassed by the invention. Such antibodies include, e.g., polyclonal antibodies, monoclonal antibodies, chimeric antibodies, human antibodies, single chain antibodies, Fab fragments, F(ab')$_2$ fragments, molecules produced using a Fab expression library, human antibodies (polyclonal or monoclonal) produced in transgenic mice and epitope binding fragments of any of the above.

The antibodies can be utilized in conjunction with gene therapy techniques to evaluate, for example, the expression of the peptides of the present invention either in cells or directly in patient tissues in which these genes have been introduced.

For the production of antibodies, a variety of host animals may be immunized by injection with peptides of the present invention, anti-peptide antibody, anti-peptide analog antibody, or immunogenic fragments thereof by methods well known in the art. For preparation of an anti-idiotype antibody the immunogen is an anti-peptide antibody or anti-peptide analog antibody. Production of anti-idiotype antibodies is described, for example, in U.S. Pat. No. 4,699,880. Suitable host animals include, but are not limited to, rabbits, mice, goats, sheep and horses. Immunization techniques are well known in the art. Polyclonal antibodies can be purified from the serum of the immunized animals, or monoclonal antibodies can be generated by methods that are well known in the art. These techniques include, but are not limited to, the well-known hybridoma techniques of Kohler and Milstein, human B-cell hybridoma techniques, and the EBV hybridoma technology. Monoclonal antibodies may be of any immunoglobulin class, including IgG, IgE, IgM, IgA, and IgD containing either kappa or lambda light chains. Techniques of producing and using chimeric antibodies are known in the art, and are described in, for example, U.S. Pat. Nos. 5,807,715; 4,816,397; 4,816,567; 5,530,101; 5,585,089; 5,693,761; 5,693,762; 6,180,370; and 5,824,307.

Assays Determining CRF$_2$R Selectivity

The pharmacological activity and selectivity of the peptides of present invention can be determined using published test procedures. See, e.g, U.S. patent application Ser. No. 09/799,978. Because CRF$_2$R and CRF$_1$R are homologous proteins, it is expected that a certain proportion of agonists for CRF$_2$R will also function as agonists of CRF$_1$R. As discussed above, activation of CRF$_1$R induces activation of the HPA axis since increased corticosteroid production leads to skeletal muscle atrophy. In most cases in which an increase in muscle mass or function is desired, it is not desirable to activate the HPA axis. When selecting a peptide useful for the treatment of a CRF$_2$R modulated disorder, which is not related to muscular dystrophy, it is preferable that the peptide be selective for CRF$_2$R. Preferably the peptide exhibits 10-fold selectivity for CRF$_2$R versus CRF$_1$R (i.e., 10-fold more active against CRF$_2$R than against CRF$_1$R), more preferably 100-fold selectivity and most preferably 1000-fold or greater selectivity. As published studies have demonstrated a benefit of corticosteroid therapy in the treatment of muscular dystrophies, it may be beneficial that a CRF$_2$R agonist retain some level of CRF$_1$R agonism when used to treat muscular dystrophies. Thus, for the treatment of muscular dystrophies, a peptide of lower selectivity that activates the CRF$_2$R as well as the CRF$_1$R, over a similar concentration range, is preferred. Preferably the peptide is 100-fold selective for CRF$_2$R versus CRF$_1$R, more preferably 10-fold selective and most preferably not selective for CRF$_2$R versus CRF$_1$R (i.e., the activity of the candidate compound is substantially similar for CRF$_2$R and CRF$_1$R). Also, in this case, it may be more preferable that the peptide is full agonist for CRF$_2$R while being a partial agonist for CRF$_1$R. Such a peptide would therefore have a built-in limit to the maximum degree of cortisol elevation and potential for muscle atrophy, while the anti-atrophy effect modulated through the CRF$_2$R could be enhanced by increasing the dose. One of skill in the art would be able to readily determine whether a peptide is a full or partial agonist of the CRF$_1$R or CRF$_2$R using methods known in the art.

Because it is desirable to discriminate binding between CRF$_2$R, as compared with CRF$_1$R, the assays described above may be conducted using a cell, or membrane from a cell, which expresses only CRF$_2$R or the assays can be conducted with a recombinant source of CRF$_2$R. Cells expressing both forms of CRFR may be modified using homologous recombination to inactivate or otherwise disable the CRF$_1$R gene. Alternatively, if the source of CRFR contains more than one CRFR type, the background signal produced by the receptor which is not of interest must be subtracted from the signal obtained in the assay. The background response can be determined by a number of methods, including elimination of the signal from the CRFR which is not of interest by use of antisense, antibodies or selective antagonists. Known antagonists of CRFRs include, but, are not limited to, antalarmin (CRF$_1$R selective), antisauvagine-30 (CRF$_2$R selective) and astressin (nonselective for CRF$_1$R/CRF$_2$R).

To determine whether a peptide activates CRF$_2$R and/or CRF$_1$R, the assays are typically cell-based; however, cell-free assays are known which are able to differentiate agonist and antagonist binding as described above. Cell-based assays include the steps of contacting cells which express CRF$_1$R or CRF$_2$R with a peptide of the present invention or control and measuring activation of the CRFR by measuring the expression or activity of components of the CRFR signal transduction pathways.

As described in the background section above, CRFRs appear to couple through several different pathways including $G_{\alpha s}$, $G_{\alpha q}$ or $G_{\alpha i}$, depending upon the cell type. It is thought that agonist activation of CRFR allows the receptor to signal via any of these pathways, provided that the necessary pathway components are present in the particular cell type. Thus, to assay a particular peptide of the present invention for CRFR activation, an assay can use any of the signal transduction pathways as the readout even if the relevant cell type for treatment, in vivo, couples CRFR to skeletal muscle atrophy via a different pathway. One of ordinary skill in the art would recognize that an assay would be effective for identifying useful peptide agonists independent of the pathway by which receptor activation was measured. Assays for measuring activation of these signaling pathways are known in the art.

For example, after contact with a peptide of the present invention, lysates of the cells can be prepared and assayed for induction of cAMP. cAMP is induced in response to $G_{\alpha s}$ activation. Because $G_{\alpha s}$ is activated by receptors other than CRFR and because a test peptide may be exerting its effect through CRFRs or by another mechanism, two control comparisons are relevant for determining whether the peptide increases levels of cAMP via activation of a CRFR. One control compares the cAMP level of cells contacted with the peptide and the cAMP level of cells contacted with a control compound (i.e., the vehicle in which the peptide is dissolved). If the peptide increases cAMP levels relative to the control compound this indicates that the peptide is increasing cAMP by some mechanism. The other control compares the cAMP levels of a CRFR expressing cell line and a cell line that is essentially the same except that it does not express the CRFR, where both of the cell lines have been treated with the peptide. If the peptide elevates cAMP levels in the CRFR expressing cell line relative to the cell line that does not express CRFRs, this is an indication that the peptide elevates cAMP via activation of the CRFRs.

In one example, cAMP induction is measured with the use of DNA constructs containing the cAMP responsive element linked to any of a variety of reporter genes can be introduced into cells expressing CRFRs. Such reporter genes include, but are not limited to, chloramphenicol acetyltransferase (CAT), luciferase, glucuronide synthetase, growth hormone, fluorescent proteins (e.g., Green Fluorescent Protein), or alkaline phosphatase. Following exposure of the cells to the peptide, the level of reporter gene expression can be quantitated to determine the peptide's ability to increase cAMP levels and thus determine the peptide's ability to activate the CRFR.

The cells useful in this assay are the same as for the CRFR binding assay described above, except that cells utilized in the activation assays preferably express a functional receptor which gives a statistically significant response to CRF or one or more CRF analog. In addition to using cells expressing full length CRFRs, cells can be engineered which express CRFRs containing the ligand binding domain of the receptor coupled to, or physically modified to contain, reporter elements or to interact with signaling proteins. For example, a wild type CRFR or CRFR fragment can be fused to a G-protein resulting in activation of the fused G-protein upon agonist binding to the CRFR portion of the fusion protein. Siefert, R. et al., *Trends Pharmacol. Sci.*, 20: 383–389 (1999). The cells should also preferably possess a number of characteristics, depending on the readout, to maximize the inductive response by CRF or the CRF analog, for example, for detecting a strong induction of a CRE reporter gene; (a) a low natural level of cAMP; (b) G proteins capable of interacting with CRFRs; (c) a high level of adenylyl cyclase; (d) a high level of protein kinase A; (e) a low level of phosphodiesterases; and (f) a high level of cAMP response element binding protein would be advantageous. To increase the response to CRF or a CRF analog, host cells could be engineered to express a greater amount of favorable factors or a lesser amount of unfavorable factors. In addition, alternative pathways for induction of the CRE reporter could be eliminated to reduce basal levels.

Assays to Determine Pharmacological Activity

The pharmacological activity of the peptides of present invention can be determined using published test procedures. For example, models of skeletal muscle atrophy or hypertrophy include both in vitro cell culture models and in vivo animal models of skeletal muscle atrophy.

In vitro models of skeletal muscle atrophy are known in the art. Such models are described, for example, in Vandenburgh, H. H., In Vitro, 24:609–619 (1988), Vandenburgh, H. H. et al., *J. Biomechanics*, 24 Suppl 1:91–99 (1991), Vandenburgh, H. H et al., In Vitro *Cell. Dev. Biol.*, 24(3): 166–174 (1988), Chromiak, J. A., et al., In Vitro Cell. Dev. Biol. Anim., 34(9):694–703 (1998), Shansky, J., et al., In Vitro *Cell. Dev. Biol. Anim.*, 33(9):659–661 (1997), Perrone, C. E. et al., *J. Biol. Chem.*, 270(5):2099–2106 (1995), Chromiac, J. A. and Vandenburgh, H. H., *J. Cell. Physiol.*, 159(3):407–414 (1994), and Vandenburgh, H. H. and Karlisch, P., In Vitro *Cell. Dev. Biol.*, 25(7):607–616 (1989).

A variety of animal models for skeletal muscle atrophy are known in the art, such as those described in the following references: Herbison, G. J., et al. *Arch. Phys. Med. Rehabil.*, 60:401–404 (1979), Appell, H-J. *Sports Medicine* 10:42–58 (1990), Hasselgren, P-O. and Fischer, J. E. *World J. Surg.*, 22:203–208 (1998), Agbenyega, E. T. and Wareham, A. C. *Comp. Biochem. Physiol.*, 102A:141–145 (1992), Thomason, D. B. and Booth, F. W. *J. Appl. Physiol.*, 68:1–12 (1990), Fitts, R. H., et al. *J. Appl. Physiol.*, 60:1946–1953 (1986), Bramanti, P., et al. *Int. J. Anat. Embryol.* 103:45–64 (1998), Cartee, G. D. *J. Gerontol. A Biol. Sci. Med. Sci.*, 50:137–141 (1995), Cork, L. C., et al. *Prog. Clin. Biol. Res.*, 229:241–269 (1987), Booth, F. W. and Gollnick, P. D. *Med. Sci. Sports Exerc.*, 15:415–420 (1983), Bloomfield, S. A. *Med. Sci. Sports Exerc.*, 29:197–206 (1997). Preferred animals for these models are mice and rats. These models include, for example, models of disuse-induced atrophy such as casting or otherwise immobilizing limbs, hind limb suspension, complete animal immobilization, and reduced gravity situations. Models of nerve damage induced atrophy include, for example, nerve crush, removal of sections of nerves which innervate specific muscles, toxin application to nerves and infection of nerves with viral, bacterial or eukaryotic infectious agents. Models of glucocorticoid-induced atrophy include application of atrophy-inducing doses of exogenous glucocorticoid to animals, and stimulation of endogenous corticosteroid production, for example, by application of hormones that activate the hypothalamus-pituitary-adrenal (HPA) axis. Models of sepsis-induced atrophy include, for example, inoculation with sepsis-inducing organisms such as bacteria, treatment of the animal with immune-activating compounds such as bacterial cell wall extract or endotoxin, and puncture of intestinal walls. Models of cachexia-induced atrophy include, for example, inoculation of an animal with tumorigenic cells with cachexia forming potential, infection of an animal with infectious agents (such as viruses which cause AIDS) which result in cachexia and treatment of an animal with hormones or cytokines such as CNTF, TNF, IL-6, IL-1, etc. which induce cachexia. Models of heart failure-induced atrophy include the manipulation of an animal so that heart failure occurs with concomitant skeletal muscle atrophy. Neurodegenerative disease-induced atrophy models include autoimmune animal models such as those resulting from immunization of an animal with neuronal components. Muscular dystrophy-induced models of atrophy include natural or man-made genetically induced models of muscular dystrophy such as the mutation of the dystrophin gene which occurs in the Mdx mouse.

Animal models of skeletal muscle hypertrophy include, for example, models of increased limb muscle use due to inactivation of the opposing limb, reweighing following a disuse atrophy inducing event, reutilization of a muscle which atrophied because of transient nerve damage, increased use of selective muscles due to inactivation of a synergistic muscle (e.g., compensatory hypertrophy), increased muscle utilization due to increased load placed on the muscle and hypertrophy resulting from removal of the glucocorticoid after glucocorticoid-induced atrophy. Preferred animal atrophy models include the sciatic nerve denervation atrophy model, glucocorticoid-induced atrophy model, and the leg casting disuse atrophy model that are described in further detail below.

The sciatic nerve denervation atrophy model involves anesthetizing the animal followed by the surgical removal of a short segment of either the right or left sciatic nerve, e.g., in mice the sciatic nerve is isolated approximately at the midpoint along the femur and a 3–5 mm segment is removed. This denervates the lower hind limb musculature resulting in atrophy of these muscles. Typically, innervation to the biceps femoris is left intact to provide satisfactory motion of the knee for virtually normal ambulation. Typically, in untreated animals, muscle mass of the denervated muscles is reduced 30–50% ten days following denervation. Following denervation, test peptides are administered e.g., by injection or by continuous infusion, e.g., via implantation of an osmotic minipump (e.g., Alzet, Palo Alto, Calif.), to determine their effect on denervation induced skeletal muscle atrophy. At various times following denervation, the animals are euthanized and lower leg muscles are dissected rapidly from both the denervated and nondenervated legs, the muscles, cleaned of tendons and connective tissue, are weighed. The extent of atrophy in the affected muscles is analyzed, for example, by measuring muscle mass, muscle cross-sectional area, myofiber cross-sectional area or contractile protein content.

The glucocorticoid-induced atrophy model involves the administration of a glucocorticoid to the test animal, e.g., 1.2 mg/kg/day of dexamethasone in the drinking water. Typically, in untreated animals, skeletal muscle mass is reduced 30–50% following ten days of dexamethasone administration. Concomitantly with, or following glucocorticoid administration, test peptides are administered e.g., by injection or by continuous infusion to determine their effect on glucocorticoid-induced skeletal muscle atrophy. At various times following glucocorticoid administration, the extent of atrophy in the affected muscles is analyzed as described above for the denervation model.

The leg casting disuse atrophy model involves casting one hind leg of an animal from the knee down through the foot. Typically, muscle mass is reduced 20–40% after ten days of casting. Following casting, test peptides are administered by injection or by continuous infusion via implantation of an osmotic minipump (e.g., Alzet, Palo Alto, Calif.) to determine their effect on leg casting induced skeletal muscle atrophy. At various times following leg casting, the extent of atrophy in the affected muscles is analyzed as described above for the denervation model.

Bone activity of the subject peptides can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Compositions

Another aspect of this invention is compositions which comprise: (a) a safe and effective amount of a peptide of the present invention; and (b) a pharmaceutically-acceptable carrier. Standard pharmaceutical formulation techniques are used, such as those disclosed in *Remington's Pharmaceutical Sciences*, Mack Publishing Company, Easton, Pa., latest edition.

A "safe and effective amount" means an amount of the peptide of the invention sufficient to significantly induce a positive modification in the condition to be treated, but low enough to avoid serious side effects (such as toxicity, irritation, or allergic response) in an animal, preferably a mammal, more preferably a human subject, in need thereof, commensurate with a reasonable benefit/risk ratio when used in the manner of this invention. The specific "safe and effective amount" will, obviously, vary with such factors as the particular condition being treated, the physical condition of the subject, the duration of treatment, the nature of concurrent therapy (if any), the specific dosage form to be used, the carrier employed, the solubility of the peptide therein, and the dosage regimen desired for the composition. One skilled in the art may use the following teachings to determine a "safe and effective amount" in accordance with the present invention. Spilker B., *Guide to Clinical Studies and Developing Protocols*, Raven Press Books, Ltd., New York, 1984, pp. 7–13, 54–60; Spilker B., Guide to Clinical Trials, Raven Press, Ltd., New York, 1991, pp. 93–101; Craig C., and R. Stitzel, eds., *Modern Pharmacology*, 2d ed., Little, Brown and Co., Boston, 1986, pp. 127–33; T. Speight, ed., *Avery's Drug Treatment: Principles and Practice of Clinical Pharmacology and Therapeutics*, 3d ed., Williams and Wilkins, Baltimore, 1987, pp. 50–56; R. Tallarida, R. Raffa and P. McGonigle, *Principles in General Pharmacology*, Springer-Verlag, New York, 1988, pp. 18–20.

In addition to the subject peptide, the compositions of the subject invention contain a pharmaceutically acceptable carrier. The term "pharmaceutically-acceptable carrier," as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject peptide, and with each other, in a manner such that there is no interaction that would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are: sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the peptide is to be administered.

If the subject peptide is to be injected, the preferred pharmaceutically-acceptable carrier is sterile, physiological saline, with a blood-compatible colloidal suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) peptide that is suitable for administration to an animal, preferably a mammal, more preferably a human subject, in a single dose, according to good medical practice. These compositions preferably contain from about 0.1 mg (milligrams) to about 1000 mg, more preferably from about 0.5 mg to about 500 mg, more preferably from about 1 mg to about 30 mg, of a peptide of Formula (I).

The compositions of this invention may be in any of a variety of forms, suitable, for example, for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the $CRF_2R$ agonist activity of the peptides of Formula (I). The amount of carrier employed in conjunction with the Formula (I) peptide is sufficient to provide a practical quantity of material for administration per unit dose of the Formula (I) peptide. Techniques and compositions for making dosage forms useful in the methods of this invention are described in the following references,: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the peptide. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, and containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art. In general, the formulation will include the peptide, and inert ingredients which allow for protection against the stomach environment, and release of the biologically active material in the intestine.

The peptide of Formula (I) may be chemically modified so that oral delivery of the derivative is efficacious. Generally, the chemical modification contemplated is the attachment of at least one moiety to the protein molecule itself, where said moiety permits (a) inhibition of proteolysis; and (b) uptake into the blood stream from the stomach or intestine. Also desired is the increase in overall stability of the protein and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Newmark et al., *J. Appl. Biochem.*, 4:185–189 (1982). Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or variant) or by release of the biologically active material beyond the stomach environment, such as in the intestine.

To ensure full gastric resistance, a coating impermeable to at least pH 5.0 is preferred. Examples of the more common inert ingredients that are used as enteric coatings are cellulose acetate trimellitate (CAT), hydroxypropylmethylcellulose phthalate (HPMCP), HPMCP 50, HlPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Compositions of the subject invention may optionally include other active agents. Non-limiting examples of active agents are listed in WO 99/15210.

Other compositions useful for attaining systemic delivery of the subject compounds include sublingual, buccal, suppository, nasal and pulmonary dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch." An example of a suitable patch applicator is described in U.S. patent application Ser. No. 10/054,113. Such compositions include, for example, lotions, creams, solutions, gels and solids. These topical compositions preferably comprise a safe and effective amount, usually at least about 0.1%, and preferably from about 1% to about 5%, of the peptide. Suitable carriers for topical administration preferably remain in place on the skin as a continuous film, and resist being removed by perspiration or immersion in water. Generally, the carrier is organic in nature and capable of having dispersed or dissolved therein the peptide. The carrier may include pharmaceutically-acceptable emollients, emulsifiers, thickening agents, solvents and the like.

Methods of Administration

This invention also provides methods of treating $CRF_2R$ modulated disorders in a human or other animal subject, by administering a safe and effective amount of a peptide to said subject. The methods of the invention are useful in preventing or treating disorders described above.

Compositions of this invention can be administered topically or systemically. Systemic application includes any method of introducing a peptide of Formula (I) into the tissues of the body, e.g., intra-articular (especially in treatment of rheumatoid arthritis), intrathecal, epidural, intramuscular, transdermal, intravenous, intraperitoneal, subcutaneous, nasal, pulmonary, sublingual, rectal, and oral administration.

The specific dosage of the peptide to be administered, as well as the duration of treatment, and whether the treatment is topical or systemic are interdependent. The dosage and treatment regimen will also depend upon such factors as the specific peptide used, the treatment indication, the ability of the peptide to reach minimum inhibitory concentrations at the site of the tissue in need of treatment, the personal attributes of the subject (such as weight), compliance with the treatment regimen, and the presence and severity of any side effects of the treatment.

Topical administration can be used to deliver the peptide systemically, or to treat a subject locally. The amounts of the peptide to be topically administered depends upon such factors as skin sensitivity, type and location of the tissue to be treated, the composition and carrier (if any) to be administered, the particular peptide to be administered, as well as the particular disorder to be treated and the extent to which systemic (as distinguished from local) effects are desired.

The peptides of the present invention can be targeted to specific locations where treatment is need by using targeting ligands. For example, to focus a peptide to treat muscular dystrophy, the peptide is conjugated to an antibody or fragment thereof which is immunoreactive with a skeletal muscle marker as is generally understood in the art. The targeting ligand can also be a ligand suitable for a receptor which is present on skeletal muscle. Any targeting ligand which specifically reacts with a marker for the intended target tissue can be used. Methods for coupling the invention compound to the targeting ligand are well known and are similar to those described below for coupling to carrier.

A peptide of Formula (I) may be administered via a controlled release. For example, the peptide may be administered using intravenous infusion, an implantable osmotic pump, a transdermal patch, liposomes, subcutaneous depot injection containing a biodegradable material, or other modes of administration. In one embodiment, a pump may be used Langer et al., eds., *Medical Applications of Controlled Release*, CRC Pres., Boca Raton, Fla. (1974); Sefton, *CRC Crit. Ref. Biomed. Eng.,* 14:201 (1987); Buchwald et al., *Surgery,* 88:507 (1980); Saudek et al., *N. Engl. J. Med.,* 321:574 (1989). In another embodiment, polymeric materials can be used. Langer, 1974, supra; Sefton, 1987, supra; Smolen et al., eds., *Controlled Drug Bioavailability, Drug Product Design and Performance*, Wiley, N.Y. (1984); Ranger et al., *J. Macromol. Sci. Rev. Macromol. Chem.,* 23:61 (1983); see also Levy et al., *Science,* 228:190 (1985); During et al., *Ann. Neurol.,* 25:351 (1989); Howard et al., *J. Neurosurg.,* 71:105 (1989). In yet another embodiment, a controlled release system can be placed in proximity of the therapeutic target thus requiring only a fraction of the systemic dose. See. e.g., Goodson, in *Medical Applications of Controlled Release*, vol. 2, pp. 115–138 (1984). In yet another embodiment, a polymer-based drug-delivery system wherein drugs are delivered from polymer or lipid systems. These systems deliver a drug by three general mechanisms: (1) diffusion of the drug species from or through the system; (2) a chemical or enzymatic reaction leading to degradation of the system, or cleavage of the drug from the system; and (3) solvent activation, either through osmosis or swelling of the system. Suitable systems are described in review articles: Langer, Robert, "Drug delivery and targeting," Nature: 392 (Supp):5–10 (1996); Kumar, Majeti N. V., "Nano and Microparticles as Controlled Drug Delivery Devices," *J Pharm Pharmaceut Sci,* 3(2):234–258 (2000); Brannon-Peppas, "Polymers in Controlled Drug Delivery," Medical Plastics and Biomaterials, (November 1997). See also, Langer, 1990, supra; Treat et al., in *Liposomes in the Therapy of Infectious Disease and Cancer*, Lopez-Berestein and Fidler (eds.), Liss, New York, pp. 353–365 (1989); Langer, *Science,* 249:1527–1533 (1990). Suitable systems may include: Atrigel™ drug delivery system from Atrix Labs; DepoFoaM™ from SkyPharma; polyethylene glycol-based hydrogels from Infimed Therapeutics, Inc.; ReGel™, SQZGel™ oral, HySolv™ and ReSolv™ solubilizing drug-delivery systems from MacroMed; ProGelz™ from ProGelz' Products; and ProLease™ injectable from Alkermes.

In all of the foregoing, of course, the peptides of the invention can be administered alone or as mixtures, and the compositions may further include additional drugs or excipients as appropriate for the indication.

Gene Therapy

Expression vectors may be used to introduce the nucleic acids of the invention into a cell as part of gene therapy. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g., plasmid, retrovirus, lentivirus, adenovirus and the like, where the vectors are able to transiently or stably be maintained in the cells, usually for a period of at least about one day, more usually for a period of at least about several days to several weeks.

The proteins and nucleic acids of the invention may be introduced into tissues or host cells by any number of routes, including viral infection, microinjection, or fusion of vesicles. Jet injection may also be used for intramuscular administration, as described by Furth et al., *Anal. Biochem.*, 205:365–368 (1992). The DNA may be coated onto gold microparticles, and delivered intradermally by a particle bombardment device, or "gene gun" as described in the literature. See, e.g., Tang et al., *Nature* 356:152–154 (1992), where gold microprojectiles are coated with DNA, then bombarded into skin cells.

Kits

The present invention includes a kit for preventing or treating a $CRF_2R$ modulated disorder comprising: (a) a peptide of Formula (I) in a unit dose form; and (b) usage instructions. Such a kit preferably includes a number of unit dosages. Such kits can include a card having dosages oriented in the order of their intended use. An example of such a kit is a "blister pack." Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered. Example of a kit is described in WO 01/45636. Treatments schedules are within the purview of those skilled in the medicinal arts. Non-limiting examples include once daily, weekly, biweekly, monthly, or bimonthly.

EXAMPLES

Example 1

Savagine and other non-selective CRFR agonists are generally not effective in treating $CRF_2R$ modulated disorders because these agonists also activate $CRF_1R$ thereby resulting in undesirable side effects.

Table 2 reflects comparative CRF binding for native sequence fragments of human urocortin I (hUcnI), human urocortin II (hUroII), human urocortin III (hUroIII), human corticotropin releasing factor (hCRF), ovine corticotropin (oCRF), and savagine (Svg) designated as SEQ ID NO: 2, 4, 6, 8, 10 and 11, respectively.

TABLE 2

| SEQ ID NO | PEPTIDE | $CRF_2R$ $EC_{50}$ (nM) (Emax %) | $CRF_1R$ $EC_{50}$ (nM) (Emax %) |
|---|---|---|---|
| 2 | hUcnI | 3.52 (100) | 9.00 (100) |
| 4 | hUroII | 3.64 (98) | >100 (9) |
| 6 | hUroIII | >100 (60) | >1000 (10.25) |
| 8 | hCRF | 49.25 (100) | 19.95 (87) |
| 10 | oCRF | >100 (33) | 27.35 (98) |
| 11 | Svg | 6.03 (95) | 17.60 (100) |

Example 2

Table 3 reflects comparative CRF binding of various embodiments of the invention.

TABLE 3

| SEQ ID NO | $CRF_2R$ $EC_{50}$ (nM) (Emax %) | $CRF_1R$ $EC_{50}$ (nM) (Emax %) |
|---|---|---|
| 1 | 31.50 (100) | 783 (64) |
| 3 | 12.13 (88) | 1000 (12) |
| 5 | 100 (12) | 100 (9) |
| 7 | 100 (19) | 100 (4) |
| 9 | 100 (34) | 100 (10) |
| 12 | 9.72 (91) | 928 (73) |
| 13 | 3.88 (79) | 97.65 (69) |
| 14 | 6.33 (90) | 109.00 (92) |
| 15 | 6.56 (97) | 85.30 (86) |
| 16 | 7.88 (86) | 136.00 (98) |
| 17 | 10.20 (96) | 260.50 (98) |
| 18 | 5.29 (97) | 106.00 (100) |
| 19 | 7.42 (75) | 232.50 (83) |
| 20 | 7.81 (99) | 906.00 (60) |
| 21 | 8.46 (96) | 908.00 (88) |
| 22 | 8.33 (100) | 1000.00 (64) |
| 23 | 10.20 (100) | 1000.00 (82) |
| 24 | 43.15 (100) | >1000 (18) |
| 25 | 80.95 (81.90) | 677.00 (92.35) |
| 26 | 91.75 (86) | >1000 (16) |
| 27 | 10.70 (96) | 325 (100) |
| 28 | 100 (15) | >1000 (2) |
| 29 | 16.00 (100) | >1000 (79) |
| 30 | 18.70 (85.50) | 100.45 (100) |
| 31 | 30.75 (100) | >1000 (18) |
| 32 | 20.25 (98) | 606 (94) |
| 34 | >100 (45) | >1000 (11) |
| 35 | 15.55 (88) | >1000 (74) |
| 36 | 14.75 (73) | >1000 (33) |
| 37 | >100 (51) | >1000 (5) |
| 38 | 71.90 (91) | >1000 (11) |
| 39 | 58.17 (94) | 1000 (63) |
| 40 | 6.95 (93) | 102.5 (99) |
| 41 | 18.30 (100) | >1000 (43) |
| 42 | >100 (88) | >1000 (10) |
| 43 | >100 (67) | >1000 (10) |
| 44 | 19.15 (87) | 943.50 (64) |
| 45 | >100 (44) | >1000 (7) |
| 46 | >100 (100) | >1000 (17) |
| 47 | >100 (66) | 1000 (12) |
| 48 | 100 (14) | 1000 (21) |
| 49 | >1000 (37) | >1000 (15) |
| 50 | 19.04 (94) | >1000 (42) |
| 51 | 20.65 (100) | >1000 (48) |
| 52 | >100 (10) | >1000 (13) |
| 53 | >100 (95) | >1000 (19) |
| 54 | 100 (11) | 1000 (10) |
| 55 | 7.95 (95) | 11.60 (92) |
| 56 | 50.35 (87) | >100 (14) |
| 57 | >100 (46) | >100 (12) |
| 58 | 71.60 (100) | >100 (16) |
| 59 | >100 (27) | >100 (10) |
| 60 | >100 (44) | >100 (8) |
| 61 | >100 (89) | >100 (12) |
| 63 | 67.35 (100) | 73.15 (34) |
| 64 | 63.30 (94) | 68.90 (57) |
| 65 | 67.90 (64) | >100 (16) |
| 67 | 10.02 (50) | 44.17 (96) |
| 68 | 38.55 (74) | >100 (33) |
| 69 | 5.85 (81) | 34.50 (88) |
| 70 | 18.25 (82) | >100 (8) |
| 71 | 94.80 (56) | >100 (6) |
| 72 | >100 (55) | >100 (4) |
| 73 | >100 (11) | >100 (11) |
| 74 | 54.97 (100) | >100 (7) |
| 75 | >100 (52) | >100 (5) |
| 76 | 91.45 (76) | >100 (7) |
| 77 | 43.35 (100) | >100 (5) |
| 78 | 24.65 (78) | >100 (6) |
| 79 | 22.30 (100) | >100 (8) |
| 80 | 6.53 (88) | >100 (55) |
| 81 | 4.30 (73) | 60.90 (81) |
| 82 | 10.87 (90) | 96.20 (85) |
| 83 | 1.91 (81) | 52.17 (96) |
| 84 | 1.77 (100) | 82.23 (99) |
| 85 | 2.34 (100) | 11.00 (84) |

TABLE 3-continued

| SEQ ID NO | CRF$_2$R EC$_{50}$ (nM) (Emax %) | CRF$_1$R EC$_{50}$ (nM) (Emax %) |
|---|---|---|
| 86 | 100 (8.10) | 100 (4.60) |
| 87 | 100 (14.65) | 100 (5.30) |
| 88 | 100 (12.60) | 100 (11.15) |
| 89 | 100 (12.70) | |
| 90 | 100 (12.25) | 100 (4.00) |
| 91 | 100 (7.10) | 100 (4.00) |
| 92 | 100 (15.85) | 100 (4.60) |
| 93 | 100 (6.40) | 100 (5.00) |
| 94 | 100 (6.15) | 100 (7.30) |
| 95 | 100 (8.25) | 100 (5.55) |
| 96 | 100 (12.50) | 100 (16.30) |
| 97 | 100 (7.60) | 100 (4.25) |
| 98 | 100 (5.50) | 100 (4.00) |
| 99 | 100 (4.35) | 100 (4.35) |
| 100 | 100 (9.85) | 100 (6.25) |
| 101 | 100 (6.95) | 100 (7.35) |
| 102 | 100 (13.50) | 100 (7.80) |
| 103 | 100 (4.85) | 100 (5.75) |
| 104 | 100 (4.50) | 100 (11.10) |
| 105 | 100 (9.15) | 100 (5.20) |
| 106 | 100 (6.10) | 100 (4.80) |
| 107 | 12.13 (87.90) | 1000 (12.40) |
| 108 | 79.00 (97) | >100 (3) |
| 109 | 11.83 (91.67) | 100 (6.70) |
| 110 | 10.96 (100) | >100 (9) |
| 111 | 10.95 (99) | >100 (9) |
| 112 | 12.30 (100) | >100 (10) |
| 113 | 11.30 (98) | >100 (4) |
| 114 | 3.42 (100) | >100 (6) |
| 115 | 13.60 (98) | >100 (7) |
| 116 | 100 (26.45) | 100 (4.80) |
| 117 | 9.41 (98.85) | 100 (7.80) |
| 118 | 14.60 (100) | >100 (5) |
| 119 | 3.57 (95) | >100 (3) |
| 120 | 69.90 (100) | 100 (7) |
| 121 | 5.67 (91) | >100 (3) |
| 122 | 3.31 (97) | 1000 (10.7) |
| 123 | 3.49 (93.75) | >1000 (9.60) |
| 124 | 3.49 (94) | >100 (6) |
| 125 | 4.47 (99) | >100 (9) |
| 126 | 13.00 (91) | >100 (7) |
| 127 | 7.79 (94) | >100 (6) |
| 128 | 2.85 (98) | >100 (8) |
| 129 | 3.83 (92) | >100 (12) |
| 130 | 8.57 (92) | >100 (9) |
| 131 | 5.25 (91) | >100 (8) |
| 132 | 7.53 (88) | >100 (8) |
| 133 | 12.22 (88) | >100 (4) |
| 134 | >100 (19) | >100 (7) |
| 135 | >100 (76) | >100 (6) |
| 136 | 23.40 (68) | >100 (8) |
| 137 | 36.90 (100) | >100 (4) |
| 138 | 59.00 (46) | >100 (5) |
| 139 | 42.60 (60) | >100 (4) |
| 141 | >100 (29) | >100 (7) |
| 142 | 9.08 (77.00) | 43.45 (85.35) |
| 143 | 11.05 (85.50) | 232.00 (100) |
| 144 | 9.16 (85.53) | 567 (100) |
| 145 | 7.80 (69.00) | 196.50 (91.30) |
| 146 | 8.20 (84.50) | 103 (100) |
| 147 | 6.75 (94.00) | 101.60 (96.00) |
| 148 | 9.45 (51.50) | 295.00 (100) |
| 149 | 26.20 (95.50) | 1000 (40.70) |
| 150 | 34.65 (70.50) | 1000 (5.70) |
| 151 | 36.75 (96.00) | 1000 (19.90) |
| 152 | >100 (19) | >100 (4) |
| 153 | 9.28 (97) | >100 (7) |
| 154 | 10.30 (100) | >100 (7) |
| 155 | 20.60 (94) | 40.65 (16) |
| 156 | 9.29 (79) | >100 (6) |
| 157 | 42.00 (60.65) | 100 (91.00) |
| 158 | 6.37 (89) | >100 (15) |
| 159 | 90.77 (62) | >100 (9) |
| 160 | 9.15 (87) | >100 (10) |
| 161 | >100 (88) | >100 (77) |
| 162 | >100 (7) | >100 (11) |
| 163 | 4.49 (96) | >100 (13) |
| 164 | 2.24 (92) | >100 (26) |
| 165 | >100 (75) | >100 (19) |
| 166 | 3.7 (99) | 437.5 (95) |
| 167 | 13.0 (100) | 1000 (15) |
| 168 | 4.9 (75) | 1000 (52) |
| 169 | 17.8 (93) | 978.0 (26) |
| 170 | 75.0 (83) | 1000 (9) |
| 171 | 17.6 (100) | 206.0 (99) |
| 172 | 13.5 (100) | 1000 (68) |
| 173 | 100 (65.20) | 1000 (6.05) |
| 174 | 4.42 (97.2) | 1000.0 (29.10) |
| 175 | 5.42 (92.15) | 1000.0 (34.8) |
| 176 | 12.60 (90.25) | 1000.0 (26.9) |
| 177 | 5.63 (97.65) | 613.0 (69.2) |
| 178 | 5.17 (96.45) | 1000.0 (55.70) |
| 179 | 10.22 (92.5) | 477.0 (78.90) |
| 180 | 3.14 (95.7) | 125.0 (99.3) |
| 181 | 5.22 (97.75) | 154.0 (100) |
| 182 | 7.21 (91.4) | 409.0 (89.7) |
| 183 | 7.93 (100) | 415 (57.5) |
| 184 | 3.72 (96.45) | 486.0 (77.35) |
| 185 | 8.98 (100) | 358.5 (95.8) |
| 186 | 25.05 (100) | 323 (100) |
| 187 | 10.3 (100) | 31.6 (72) |
| 188 | 14.6 (100) | 162.5 (96) |
| 189 | 7.0 (96) | 62.2 (57) |
| 190 | 39.60 (31) | >100 (9) |
| 191 | 8.3 (100) | 63.7 (65) |
| 192 | 66.8 (97) | 562.0 (99) |
| 193 | 10.1 (97) | 265.5 (95) |
| 194 | 5.0 (96) | 106.0 (94) |
| 195 | 18.8 | 103.0 (93) |
| 196 | 27.7 (97) | 447.0 (96) |
| 197 | 48.1 (94) | |
| 198 | 29.9 (100) | |
| 199 | 8.5 (92) | 706.5 (93) |
| 200 | 8.8 (100) | 188.5 (99) |
| 201 | 5.0 (100) | 99.6 (80) |
| 202 | 8.7 (99) | 403.5 (100) |
| 203 | 5.2 (94) | 76.2 (86) |
| 204 | 3.6 (93) | 32.1 (74) |
| 205 | 25.0 (93) | 126.5 (88) |
| 206 | 30.5 (97) | 696.5 (97) |
| 207 | 61.4 (96) | 465.5 (88) |
| 208 | 5.6 (88) | 64.9 (81) |
| 209 | 7.4 (93) | 26.4 (80) |
| 210 | 10.2 (97) | 43.5 (90) |
| 211 | 59.5 (100) | 826.0 (37) |
| 212 | 21.3 (100) | 445.0 (100) |
| 213 | 22.3 (99) | 1000.0 (76) |
| 214 | 74.30 (60) | 100 (4) |
| 215 | 4.0 (100) | 187.5 (100) |
| 216 | 9.9 (90) | 49.8 (98) |
| 217 | 4.7 (95) | 94.7 (100) |
| 218 | 4.8 (96) | 98.4 (100) |
| 219 | 7.8 (98) | 80.9 (100) |
| 220 | 4.1 (98) | 63.6 (81) |
| 221 | 8.5 (100) | 236.5 (100) |
| 222 | 9.4 (100) | 384.5 (95) |
| 223 | 3.0 (92) | 48.1 (81) |
| 224 | 26.9 (100) | 1000.0 (27) |
| 225 | 4.8 (89) | 219.5 (97) |
| 226 | 7.6 (100) | 315 (95) |
| 227 | 33.6 (95) | 918.0 (18) |
| 228 | 7.1 (100) | 275.5 (100) |
| 229 | 10.3 (100) | 298.0 (100) |
| 230 | 8.1 (100) | 219.0 (100) |
| 231 | 5.9 (100) | 94.0 (100) |
| 232 | 45.3 (100) | 1000.0 (7) |
| 233 | 46.1 (95) | 1000 (11) |
| 234 | 20.6 (100) | 434.3 (96) |
| 235 | 25.7 (100) | 806.5 (70) |
| 236 | 40.4 (97) | 1000.0 (15) |
| 237 | 22.2 (93) | 1000.0 (18) |
| 238 | 16.7 (100) | 753.0 (88) |

TABLE 3-continued

| SEQ ID NO | CRF$_2$R EC$_{50}$ (nM) (Emax %) | CRF$_1$R EC$_{50}$ (nM) (Emax %) |
|---|---|---|
| 239 | 13.2 (100) | 587.0 (80) |
| 240 | 22.0 (100) | 915.0 (80) |
| 241 | 12.6 (99) | 307.5 (99) |
| 242 | 29.0 (94) | 358.5 (99) |
| 243 | 16.8 (100) | 440.5 (96) |
| 244 | 8.8 (98) | 299.5 (100) |
| 245 | 7.5 (93) | 381.0 (100) |
| 246 | 38.8 (100) | 1000.0 (33) |
| 247 | 18.8 (100) | 1000.0 (34) |
| 248 | 19.6 (98) | 1000.0 (32) |
| 249 | 12.2 (92) | 1000.0 (50) |
| 250 | 19.7 (100) | 137.5 (99) |
| 251 | 11.8 (100) | 926.0 (80) |
| 252 | 22.3 (100) | 226.5 (100) |
| 253 | 41.8 (86) | 1000.0 (42) |
| 254 | 100.0 (36) | 708.0 (6) |
| 255 | 7.0 (100) | 33.3 (84) |
| 256 | 12.6 (100) | 253.5 (100) |
| 257 | 100 (72.60) | 744.50 (83.50) |
| 258 | 100 (49.30) | 1000 (23.65) |
| 259 | 100 (64.95) | 819.50 (83.60) |
| 260 | 100 (89.35) | 834.00 (89.70) |
| 261 | 100 (95.30) | 274 (100) |
| 262 | 100 (92.25) | 408 (100) |
| 263 | 36.17 (93.03) | 802.50 (71.95) |
| 264 | 100.00 (66.30) | 704.50 (100) |
| 265 | 100.00 (23.35) | 1000.00 (9.30) |
| 266 | 100.00 (19.35) | 1000.00 (4.45) |
| 267 | 100.00 (44.20) | 1000.00 (22.80) |
| 268 | 100.00 (59.05) | 1000.00 (14.15) |
| 269 | 100.00 (77.30) | 1000.00 (44.30) |
| 270 | 100.00 (19.30) | 1000.00 (7.85) |
| 271 | 48.10 (68.95) | 815.00 (80.65) |
| 272 | 23.30 (100.00) | 1000.00 (51.10) |
| 273 | 31.30 (100.00) | 1000.00 (59.30) |
| 274 | 13.80 (100.00) | 508.00 (80.90) |
| 275 | 46.60 (100.00) | 1000.00 (38.30) |
| 276 | 22.10 (100.00) | 1000.00 (75.70) |
| 277 | 28.20 (100.00) | 1000.00 (39.90) |
| 278 | 19.55 (100.00) | 1000.00 (48.70) |
| 279 | 13.10 (100.00) | 1000.00 (93.00) |
| 280 | 100.00 (82.30) | 1000.00 (11.80) |
| 281 | 100.00 (78.80) | 1000.00 (12.20) |
| 282 | 25.80 (60.75) | 1000.00 (21.75) |
| 283 | 10.55 (71.95) | 635.00 (100.00) |
| 284 | 100.00 (100.00) | 1000.00 (27.70) |
| 285 | 13.95 (97.10) | 1000.00 (11.10) |
| 286 | 13.50 (92.45) | 1000.00 (19.20) |
| 287 | 11.31 (100.00) | 1000.00 (51.75) |
| 288 | 14.70 (100.00) | 838.00 (31.65) |
| 289 | 12.16 (97.30) | 1000.00 (69.55) |
| 290 | 100.00 (100.00) | 1000.00 (6.40) |
| 291 | 100.00 (63.75) | 1000.00 (4.75) |
| 292 | 100.00 (86.10) | 1000.00 (7.00) |
| 293 | 40.30 (87.00) | 520.50 (95.30) |
| 294 | 100.00 (100.00) | 1000.00 (13.60) |
| 295 | 55.05 (67.60) | 1000.00 (5.30) |
| 296 | 6.66 (65) | 100 (4) |
| 297 | 100.00 (88.30) | 1000.00 (27.250) |
| 298 | 82.00 (98.85) | 1000.00 (20.05) |
| 299 | 46.40 (71.55) | 1000.00 (10.20) |
| 300 | 17.10 (100.00) | 1000.00 (7.95) |
| 301 | 50.45 (88.40) | 690.00 (84.10) |
| 302 | 36.20 (100.00) | 366.50 (100.00) |
| 303 | 27.25 (100.00) | 581.50 (100.00) |
| 304 | 19.30 (92.55) | 115.50 (100.00) |
| 305 | 35.45 (95.20) | 1000.00 (59.55) |
| 306 | 27.55 (100.00) | 608.00 (97.65) |
| 307 | 5.82 (96.55) | 78.40 (92.65) |
| 308 | 3.30 (72.80) | 63.45 (100.00) |
| 309 | 5.55 (99.90) | 107.50 (96.35) |
| 310 | 8.70 (87.55) | 1000.00 (45.30) |
| 311 | 11.65 (100.00) | 1000.00 (29.70) |
| 312 | 14.05 (95.00) | 869.50 (62.00) |
| 313 | 11.05 (95.00) | 704.00 (87.100) |
| 314 | 10.35 (99.75) | 978.50 (82.40) |
| 315 | 9.35 (81.70) | 454.50 (100.00) |
| 316 | 10.15 (94.50) | 221.50 (92.35) |
| 317 | 9.30 (88.35) | 187.50 (100.00) |
| 318 | 9.95 (95.40) | 134.50 (92.85) |
| 319 | 8.50 (95.00) | 106.00 (88.30) |
| 320 | 19.05 (100.00) | 718.00 (68.75) |
| 321 | 19.55 (86.80) | 1000.00 (33.80) |
| 322 | 23.05 (96.45) | 1000.00 (10.65) |
| 323 | 19.60 (100.00) | 1000.00 (36.90) |
| 324 | 17.20 (100.00) | 1000.00 (46.60) |
| 325 | 11.67 (100) | 100 (5) |
| 326 | 33.70 (100.00) | 1000.00 (30.10) |
| 327 | 28.40 (100.00) | 1000.00 (36.50) |
| 328 | 11.70 (95.70) | 1000.00 (30.70) |
| 329 | 5.15 (98.30) | 1000.00 (98.40) |
| 330 | 6.00 (93.65) | 1000.00 (86.80) |
| 331 | 9.85 (100.00) | 1000.00 (78.65) |
| 332 | 9.95 (100.00) | 1000.00 (61.30) |
| 333 | 9.85 (96.90) | 1000.00 (43.80) |
| 334 | 13.15 (93.55) | 1000.00 (82.60) |
| 335 | 28.05 (90.95) | 1000.00 (49.45) |
| 336 | 17.80 (100.00) | 1000.00 (59.90) |
| 337 | 23.95 (86.65) | 1000.00 (36.45) |
| 338 | 19.30 (77.55) | 1000.00 (41.10) |
| 339 | 100.00 (47.90) | 1000.00 (13.20) |
| 340 | 7.99 (100.00) | 739.50 (95.95) |
| 341 | 8.83 (95.50) | 850.50 (82.35) |
| 342 | 20.25 (92.25) | 1000.00 (19.65) |
| 343 | 13.60 (96.55) | 783.00 (62.50) |
| 344 | 4.30 (94.47) | 650 (77.65) |
| 345 | 39.70 (100.00) | 1000.00 (18.75) |
| 346 | 8.48 (97.75) | 1000.00 (59.00) |
| 347 | 22.35 (95.65) | 1000.00 (48.75) |
| 348 | 5.77 (90.40) | 630 (86.05) |
| 349 | 13.75 (100) | 1000 (44.20) |
| 350 | 11.59 (98.10) | 1000 (48.00) |
| 351 | 12.93 (97.37) | 1000 (85.70) |
| 352 | 8.26 (83.65) | 780 (82.60) |
| 353 | 4.75 (89.90) | 229.50 (92.25) |
| 354 | 6.48 (100) | 1000 (13.40) |
| 355 | 6.03 (95) | 18 (100) |
| 356 | 83.05 (16) | 1000 (9) |
| 357 | 6.44 (100) | 331 (100) |
| 358 | 5.56 (100) | 99 (100) |
| 359 | 23.10 (100) | 230 (100) |
| 360 | 6.12 (93) | 157 (100) |
| 361 | 6.37 (99) | 149 (100) |
| 362 | 4.39 (100) | 386 (100) |
| 363 | 25.15 (100) | 1000 (20) |
| 364 | 13.20 (100) | 1000 (27) |
| 365 | 23.45 (94) | 1000 (21) |
| 366 | 100.00 (46) | 1000 (9) |
| 367 | 100.00 (18) | 1000 (6) |
| 368 | 50.35 (91) | 1000 (6) |
| 369 | 100.00 (18) | 1000 (4) |
| 370 | 51.05 (75) | 1000 (33) |
| 371 | 6.62 (97) | 1000 (22) |
| 372 | 14.20 (100) | 1000 (13) |
| 373 | 11.54 (100) | 1000 (9) |
| 374 | 15.75 (91) | 1000 (11) |
| 375 | 11.50 (100) | 1000 (22) |
| 376 | 52.55 (100) | 1000 (8) |
| 377 | 19.25 (83) | 1000 (25) |
| 378 | 14.88 (100) | 1000 (36) |
| 379 | 70.55 (94) | 1000 (8) |
| 380 | 19.00 (100) | 1000 (16) |
| 381 | 12.73 (99) | 1000 (27) |
| 382 | 39.45 (100) | 1000 (8) |
| 383 | 9.31 (96) | 1000 (55) |
| 384 | 7.10 (97.30) | 1000 (70.30) |
| 385 | 10.25 (100) | 1000 (46) |
| 386 | 8.70 (96) | 1000 (78.25) |
| 387 | 17.85 (100) | 1000 (50.10) |

Example 3

Increased In Vivo Efficacy

The peptides of the present invention exhibit extended biological availability, particularly under conditions of low dosing, as compared to known native sequences, e.g., UroII peptide fragment (SEQ ID NO: 4).

The half-life of a peptide in a subject can be determined, for example, by high performance liquid chromatography (HPLC) of serum samples collected from the subject at various times following administration of the peptide. One skilled in the art would know how to select appropriate elution buffers for HPLC based on the physicochemical properties of a particular peptide.

A non-limiting example of an in vivo study to determine efficacy is herein described. Mice are dosed by intravenous (IV) (1000 ug/kg) and subcutaneous (SC) (1000 ug/kg) routes with a peptide of Formula (I). Blood samples are obtained at various time points (IV=0, 2, 10, 30 min and 1, 2, 4 and 6 h; and SC=0, 0.25, 0.5, 1, 2, 4, and 6 h) post dosing in microcentrifuge tubes containing sodium heparin. The blood samples are further processed to obtain plasma which is stored at −70° C. until analyzed.

Plasma standards are prepared. Spiking solution of a peptide of Formula (I) covering a concentration range from 50 ng/mL to 100 μg/mL are prepared in methanol on the analysis day by serial dilution of a previously prepared 1 mg/mL peptide of Formula (I) methanolic stock solution. Similarly, the internal standard (ISTD), stable isotope labeled h-Unc-II, spiking solution is prepared by serial dilution of a stored 1 mg/mL ISTD stock solution to give a final concentration of 5 μg/mL on the day of analysis. Working plasma standards covering a mass range from 0.5 to 100 ng are prepared by adding 10 μL of the appropriate peptide of Formula (I) spiking solution into tubes already containing 10 uL of a 5 μg/mL ISTD solution, 100 μL of dd-water and 100 μL of blank rat plasma. The working standards are prepared for analysis as described below.

Quality control (QC) samples are prepared. A QC stock solution is prepared at the 50 ng/mL level by adding 25 μL of a 1 μg/mL a peptide of Formula (I) spiking solution into 475 uL of blank, heparinized rat plasma contained in a plastic vial. Working QC samples are prepared by adding 100 uL of the QC stock solution (50 ng/mL) into tubes already containing 10 μL of a 5 μg/mL ISTD solution and 100 μL of dd-water. The working QC sample was prepared for analysis as described below.

Study samples are prepared. On the day of analysis, the samples are thawed at room temperature and an aliquot of the sample was added to a tube already containing 10 μL of a 5 μg/mL ISTD solution, 100 μL of dd-water and an aliquot of blank, heparinized rat plasma. The volume of the sample and the blank rat plasma are such that the total volume of plasma is equal to 100 μL.

The working standards, working QC samples and study samples are prepared for analysis by adding 400 μL of acetonitrile to tubes containing each of these, capping, vortexing, centrifuging and isolating the supernatant. An aliquot (300 μL) of the supernatant is dried under $N_2$ and reconstituted in 50 μL of methanol/water (50/50).

The prepared working standards, working QC samples and study samples are analyzed by gradient reversed-phase high performance liquid chromatography (RP-HPLC) separation followed by sample introduction through electron spray ionization (ESI) with mass spectroscopy/mass spectroscopy (MS/MS) detection using selected reaction monitoring (SRM) in the positive ion mode. An SRM channel is monitored for h-Unc-II and the ISTD.

The dose solutions from the pharmacokinetic study are diluted with methanol and analyzed by RP-HPLC with ultraviolet detection. The concentrations of the peptide of Formula (I) in the dose solutions are calculated by interpolation from a linear regression curve constructed from known standards.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

---

SEQUENCE LISTING

```
<160> NUMBER OF SEQ IDS NOS: 530

<210> SEQ ID NO 1
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 1

Ile Val Leu Ser Leu Asp Val Pro Ile Gly Leu Leu Gln Glu Leu Leu
1               5                   10                  15

Glu Met Ala Arg Ala Glu Gln Leu Ala Gln Gln Ala His Ser Asn Arg
            20                  25                  30

Lys Leu Met Glu Ile Ile
        35
```

<210> SEQ ID NO 2
<211> LENGTH: 40
<212> TYPE: PRT
<213> ORGANISM: Homo sapiens

<400> SEQUENCE: 2

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 3
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (38)..(38)
<223> OTHER INFORMATION: AMIDATION

<400> SEQUENCE: 3

Ile Val Leu Ser Leu Asp Val Pro Ile Gly Leu Leu Gln Ile Leu Leu
1               5                   10                  15

Glu Gln Glu Lys Ala Arg Ala Ala Arg Glu Gln Ala Thr Thr Asn Ala
            20                  25                  30

Arg Ile Leu Ala Arg Val
        35

<210> SEQ ID NO 4
<211> LENGTH: 38
<212> TYPE: PRT
<213> ORGANISM: Homo sapiens

<400> SEQUENCE: 4

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 5
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 5

Ile Val Leu Ser Leu Asp Val Pro Gly Pro Leu Leu Gln Ile Leu Leu
1               5                   10                  15

-continued

Glu Gln Thr Lys Gln Glu Ala Ala Arg Glu Gln Ala Thr Thr Asn Ala
            20                  25                  30

Arg Ile Leu Ala Arg Val
        35

<210> SEQ ID NO 6
<211> LENGTH: 40
<212> TYPE: PRT
<213> ORGANISM: Homo sapiens

<400> SEQUENCE: 6

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 7
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 7

Ser Gln Glu Ile Val Leu Ser Leu Asp Val Pro Ile Gly Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 8
<211> LENGTH: 41
<212> TYPE: PRT
<213> ORGANISM: Homo sapiens

<400> SEQUENCE: 8

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 9
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 9

Ile Val Leu Ser Leu Asp Val Pro Ile Gly Leu Leu Gln Ile Leu Leu
1               5                   10                  15

```
Glu Gln Ala Arg Ala Arg Ala Ala Arg Glu Gln Ala Thr Thr Gln Ala
            20                  25                  30

Arg Ile Leu Ala Arg Val
        35
```

<210> SEQ ID NO 10
<211> LENGTH: 41
<212> TYPE: PRT
<213> ORGANISM: Ovis sp.

<400> SEQUENCE: 10

```
Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40
```

<210> SEQ ID NO 11
<211> LENGTH: 40
<212> TYPE: PRT
<213> ORGANISM: Phyllomedusa sauvagei
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 11

```
Glx Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40
```

<210> SEQ ID NO 12
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 12

```
Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Asn
            20                  25                  30

Asn Arg Leu Leu Leu Ala Thr Val
        35                  40
```

<210> SEQ ID NO 13
<211> LENGTH: 40

```
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 13

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Thr
            20                  25                  30

Asn Arg Leu Leu Leu Asp Thr Ile
        35                  40

<210> SEQ ID NO 14
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 14

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Asn
            20                  25                  30

Asn Arg Leu Leu Leu Asp Thr Ile
        35                  40

<210> SEQ ID NO 15
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 15

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Ala Ala
            20                  25                  30

Asn Arg Leu Leu Leu Asp Thr Val
        35                  40
```

```
<210> SEQ ID NO 16
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 16

Glx Gly Pro Pro Ile Ser Ile Asp Leu Pro Phe Gln Leu Leu Arg Lys
 1               5                  10                  15

Met Ile Glu Ile Glu Lys Gln Glu Lys Glu Lys Gln Gln Ala Thr Thr
            20                  25                  30

Asn Arg Leu Leu Leu Asp Thr Val
        35                  40

<210> SEQ ID NO 17
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 17

Glx Gly Pro Pro Ile Ser Ile Asp Leu Pro Phe Gln Leu Leu Arg Lys
 1               5                  10                  15

Met Ile Glu Ile Glu Lys Gln Glu Lys Glu Lys Gln Gln Ala Thr Thr
            20                  25                  30

Asn Arg Leu Leu Leu Ala Thr Val
        35                  40

<210> SEQ ID NO 18
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 18

Glx Gly Pro Pro Ile Ser Ile Asp Leu Pro Phe Gln Leu Leu Arg Lys
 1               5                  10                  15

Met Ile Glu Ile Glu Lys Gln Glu Lys Glu Lys Gln Gln Ala Thr Thr
            20                  25                  30

Asn Arg Leu Leu Leu Asp Arg Val
        35                  40
```

```
<210> SEQ ID NO 19
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 19

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Thr
            20                  25                  30

Asn Arg Leu Leu Leu Ala Arg Val
        35                  40

<210> SEQ ID NO 20
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 20

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Leu Leu Asp Thr Val
        35                  40

<210> SEQ ID NO 21
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 21

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Thr
            20                  25                  30
```

Asn Ala Arg Leu Leu Ala Thr Val
            35                  40

<210> SEQ ID NO 22
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 22

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Leu Leu Asp Arg Val
            35                  40

<210> SEQ ID NO 23
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 23

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Leu Leu Ala Arg Val
            35                  40

<210> SEQ ID NO 24
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 24

Glx Gly Pro Pro Ile Ser Ile Asp Leu Pro Ile Thr Leu Leu Arg Lys
1               5                   10                  15

Met Ile Glu Ile Glu Lys Gln Glu Lys Glu Lys Gln Gln Ala Ala Asn

Asn Arg Leu Leu Leu Asp Thr Ile
        35                  40

<210> SEQ ID NO 25
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 25

Glx Gly Pro Pro Ile Ser Ile Asp Leu Ser Ile Gly Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 26
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 26

Glx Gly Pro Pro Ile Ser Ile Asp Leu Pro Ile Pro Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 27
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 27

Glx Gly Pro Pro Ile Ser Ile Asp Leu Pro Gln Tyr Leu Leu Arg Lys
1               5                   10                  15

```
Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 28
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 28

Glx Gly Pro Pro Ile Ser Ile Asp Leu Pro Ile Asp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 29
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 29

Glx Gly Pro Pro Ile Ser Ile Asp Leu Pro Ile Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 30
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 30
```

```
Glx Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 31
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 31

Glx Gly Pro Pro Ile Ser Ile Asp Leu Pro Ile Val Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 32
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 32

Glx Gly Pro Pro Ile Ser Ile Asp Leu Pro Ala Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 33
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION
```

```
<400> SEQUENCE: 33

Glx Gly Pro Pro Ile Ser Ile Asp Leu Ser Leu Gly Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 34
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 34

Glx Gly Pro Pro Ile Ser Ile Asp Leu Pro Ile Lys Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 35
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 35

Glx Gly Pro Pro Ile Ser Ile Asp Leu Pro Ile Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 36
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
```

<223> OTHER INFORMATION: AMIDATION

<400> SEQUENCE: 36

Glx Gly Pro Pro Ile Ser Ile Asp Leu Pro Ile Ile Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 37
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 37

Glx Gly Pro Pro Ile Ser Ile Asp Leu Pro Ile Asn Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 38
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 38

Glx Gly Pro Pro Ile Ser Ile Asp Leu Pro Ile Arg Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 39
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:

```
<221> NAME/KEY: MOD_RES
<222> LOCATION: (40)..(40)
<223> OTHER INFORMATION: AMIDATION

<400> SEQUENCE: 39

Glx Gly Pro Pro Ile Ser Ile Asp Leu Pro Val Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 40
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 40

Glx Gly Pro Pro Ile Ser Ile Asp Leu Pro Tyr Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 41
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 41

Glx Gly Pro Pro Ile Ser Ile Asp Leu Pro Thr Trp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 42
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
```

```
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 42

Glx Gly Pro Pro Ile Ser Ile Asp Leu Pro Thr Thr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 43
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 43

Glx Gly Pro Pro Ile Ser Ile Asp Leu Pro Thr Ser Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 44
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 44

Glx Gly Pro Pro Ile Ser Ile Asp Leu Pro Thr Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 45
<211> LENGTH: 40
<212> TYPE: PRT
<213> ORGANISM: Artificial
<220> FEATURE:
<223> OTHER INFORMATION: Chemically synthesized artificial peptide
<220> FEATURE:
```

```
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 45

Glx Gly Pro Pro Ile Ser Ile Asp Leu Pro Thr Lys Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 46
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 46

Glx Gly Pro Pro Ile Ser Ile Asp Leu Pro Thr Val Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 47
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 47

Glx Gly Pro Pro Ile Ser Ile Asp Leu Pro Ile Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 48
<211> LENGTH: 40
<212> TYPE: PRT
<213> ORGANISM: Artificial
<220> FEATURE:
```

-continued

```
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 48

Glx Gly Pro Pro Ile Ser Ile Asp Leu Pro Glu Tyr Leu Leu Arg Lys
1               5                   10                  15

Met Ile Glu Ile Glu Lys Gln Glu Lys Gln Gln Ala Ala Asn
            20                  25                  30

Asn Arg Leu Leu Leu Asp Thr Ile
        35                  40

<210> SEQ ID NO 49
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 49

Glx Gly Pro Pro Ile Ser Ile Asp Leu Pro Thr Asp Leu Leu Arg Lys
1               5                   10                  15

Met Ile Glu Ile Glu Lys Gln Glu Lys Gln Gln Ala Ala Asn
            20                  25                  30

Asn Arg Leu Leu Leu Asp Thr Ile
        35                  40

<210> SEQ ID NO 50
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 50

Glx Gly Pro Pro Ile Ser Ile Asp Leu Pro Thr Ile Leu Leu Arg Lys
1               5                   10                  15

Met Ile Glu Ile Glu Lys Gln Glu Lys Gln Gln Ala Ala Asn
            20                  25                  30

Asn Arg Leu Leu Leu Asp Thr Ile
        35                  40

<210> SEQ ID NO 51
<211> LENGTH: 40
<212> TYPE: PRT
```

```
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 51

Glx Gly Pro Pro Ile Ser Ile Asp Leu Pro Thr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 52
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 52

Glx Gly Pro Pro Ile Ser Ile Asp Leu Pro Thr Pro Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 53
<211> LENGTH: 78
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 53

Cys His Glu Met Ile Cys Ala Leu Leu Tyr Ser Tyr Asn Thr His Glu
1               5                   10                  15

Ser Ile Glx Glu Asp Ala Arg Thr Ile Phe Ile Cys Ile Ala Leu Pro
            20                  25                  30

Glu Pro Thr Ile Asp Glu Glx Gly Pro Pro Ile Ser Ile Asp Leu Pro
        35                  40                  45

Ile Ser Leu Leu Arg Lys Met Ile Glu Ile Glu Lys Gln Glu Lys Glu
    50                  55                  60
```

```
Lys Gln Gln Ala Ala Asn Asn Arg Leu Leu Leu Asp Thr Ile
 65                  70                  75

<210> SEQ ID NO 54
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 54

Glx Gly Pro Pro Ile Ser Ile Asp Leu Pro Asp Tyr Leu Leu Arg Lys
 1               5                  10                  15

Met Ile Glu Ile Glu Lys Gln Glu Lys Glu Lys Gln Gln Ala Ala Asn
             20                  25                  30

Asn Arg Leu Leu Leu Asp Thr Ile
         35                  40

<210> SEQ ID NO 55
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 55

Glx Gly Pro Pro Ile Ser Ile Asp Leu Pro Trp Tyr Leu Leu Arg Lys
 1               5                  10                  15

Met Ile Glu Ile Glu Lys Gln Glu Lys Glu Lys Gln Gln Ala Ala Asn
             20                  25                  30

Asn Arg Leu Leu Leu Asp Thr Ile
         35                  40

<210> SEQ ID NO 56
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 56

Glx Gly Pro Pro Ile Ser Ile Asp Leu Pro Ser Tyr Leu Leu Arg Lys
 1               5                  10                  15

Met Ile Glu Ile Glu Lys Gln Glu Lys Glu Lys Gln Gln Ala Ala Asn
```

Asn Arg Leu Leu Leu Asp Thr Ile
        35                  40

<210> SEQ ID NO 57
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 57

Glx Gly Pro Pro Ile Ser Ile Asp Leu Pro Pro Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 58
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 58

Glx Gly Pro Pro Ile Ser Ile Asp Leu Pro Lys Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 59
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 59

Glx Gly Pro Pro Ile Ser Ile Asp Leu Pro Thr Asn Leu Leu Arg Lys
1               5                   10                  15

```
Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 60
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 60

Glx Gly Pro Pro Ile Ser Ile Asp Leu Pro Thr Arg Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 61
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 61

Glx Gly Pro Pro Ile Ser Ile Asp Leu Pro Thr Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 62
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 62
```

Glx Gly Pro Pro Ile Ser Ile Asp Leu Pro His Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 63
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 63

Glx Gly Pro Pro Ile Ser Ile Asp Leu Pro Gly Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 64
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 64

Glx Gly Pro Pro Ile Ser Ile Asp Leu Pro Asn Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 65
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION -continued

```
<400> SEQUENCE: 65

Glx Gly Pro Pro Ile Ser Ile Asp Leu Pro Arg Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 66
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 66

Glx Gly Pro Pro Ile Ser Ile Asp Leu Pro Leu Gly Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 67
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 67

Glx Gly Pro Pro Ile Ser Ile Asp Leu Pro Phe Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 68
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
```

<223> OTHER INFORMATION: AMIDATION

<400> SEQUENCE: 68

Glx Gly Pro Pro Ile Ser Ile Asp Leu Pro Phe Gly Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 69
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 69

Glx Gly Pro Pro Ile Ser Ile Asp Leu Pro Phe His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 70
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 70

Glx Gly Pro Pro Ile Ser Ile Asp Leu Pro Thr Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 71
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:

<221> NAME/KEY: MOD_RES
<222> LOCATION: (40)..(40)
<223> OTHER INFORMATION: AMIDATION

<400> SEQUENCE: 71

Glx Gly Pro Pro Ile Ser Ile Asp Leu Pro Thr Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 72
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 72

Glx Gly Pro Pro Ile Ser Ile Asp Leu Pro Thr Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 73
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 73

Glx Gly Pro Pro Ile Ser Ile Asp Leu Pro Thr Gly Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 74
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)

```
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 74

Glx Gly Pro Pro Ile Ser Ile Asp Leu Pro Thr His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 75
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 75

Glx Gly Pro Pro Ile Ser Ile Asp Leu Pro Ile Gly Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 76
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 76

Glx Gly Pro Pro Ile Ser Ile Asp Leu Pro Ile Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 77
<211> LENGTH: 40
<212> TYPE: PRT
<213> ORGANISM: Artificial
<220> FEATURE:
<223> OTHER INFORMATION: Chemically synthesized artificial peptide
<220> FEATURE:
```

<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 77

Glx Gly Pro Pro Ile Ser Ile Asp Leu Pro Ile His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 78
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 78

Glx Gly Pro Pro Ile Ser Ile Asp Leu Pro Ile Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 79
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 79

Glx Gly Pro Pro Ile Ser Ile Asp Leu Pro Ile Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 80
<211> LENGTH: 40
<212> TYPE: PRT
<213> ORGANISM: Artificial
<220> FEATURE:

```
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 80

Glx Gly Pro Pro Ile Ser Ile Asp Leu Pro Leu Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 81
<211> LENGTH: 39
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (39)..(39)
<223> OTHER INFORMATION: AMIDATION

<400> SEQUENCE: 81

Glx Gly Pro Pro Ile Ser Ile Asp Leu Pro Leu Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr
        35

<210> SEQ ID NO 82
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 82

Glx Gly Pro Pro Ile Ser Ile Asp Leu Pro Leu Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 83
<211> LENGTH: 40
<212> TYPE: PRT
```

-continued

```
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 83

Glx Gly Pro Pro Ile Ser Ile Asp Leu Pro Leu His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 84
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 84

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 85
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 85

Glx Gly Pro Pro Ile Ser Ile Asp Leu Pro Phe Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 86
```

```
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 86

Ser Gln Glu Pro Pro Ile Ser Leu Asp Leu Thr Ile Gly Leu Leu Arg
1               5                   10                  15
Glu Val Leu Glu Met Thr Lys Ala Asp Gln Leu Ala Gln Gln Ala His
            20                  25                  30
Ser Asn Arg Lys Leu Leu Asp Ile Ala
        35                  40

<210> SEQ ID NO 87
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 87

Ser Gln Glu Pro Pro Ile Ser Leu Asp Leu Thr Ile His Leu Leu Arg
1               5                   10                  15
Glu Val Leu Glu Met Thr Lys Ala Asp Gln Leu Ala Gln Gln Ala His
            20                  25                  30
Ser Asn Arg Lys Leu Leu Asp Ile Ala
        35                  40

<210> SEQ ID NO 88
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 88

Ser Gln Glu Pro Pro Ile Ser Leu Asp Leu Thr Phe Gly Leu Leu Arg
1               5                   10                  15
Glu Val Leu Glu Met Thr Lys Ala Asp Gln Leu Ala Gln Gln Ala His
            20                  25                  30
Ser Asn Arg Lys Leu Leu Asp Ile Ala
        35                  40

<210> SEQ ID NO 89
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION
```

```
<400> SEQUENCE: 89

Ser Gln Glu Pro Pro Ile Ser Leu Asp Leu Pro Leu Glu Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 90
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 90

Ser Gln Glu Pro Pro Ile Ser Leu Asp Leu Pro Leu Gly Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 91
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 91

Ser Gln Glu Pro Pro Ile Ser Leu Asp Leu Pro Phe Gln Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 92
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 92

Ser Gln Glu Pro Pro Ile Ser Leu Asp Leu Pro Thr Glu Leu Leu Arg
1               5                   10                  15

Glu Val Leu Glu Met Thr Lys Ala Asp Gln Leu Ala Gln Gln Ala His
            20                  25                  30

Ser Asn Arg Lys Ile Ile Asp Ile Ala
        35                  40
```

<210> SEQ ID NO 93
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 93

Ser Gln Glu Pro Pro Ile Ser Leu Asp Leu Pro Ile Gly Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 94
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 94

Ser Gln Glu Pro Pro Ile Ser Leu Asp Leu Pro Ile His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 95
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 95

Ser Gln Glu Pro Pro Ile Ser Leu Asp Leu Pro Leu Gln Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 96
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES

```
<222> LOCATION: (41)..(41)
<223> OTHER INFORMATION: AMIDATION

<400> SEQUENCE: 96

Ser Gln Glu Pro Pro Ile Ser Leu Asp Leu Pro Phe Tyr Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 97
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 97

Ser Gln Glu Pro Pro Ile Ser Leu Asp Leu Pro Phe Glu Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 98
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 98

Ser Gln Glu Pro Pro Ile Ser Leu Asp Leu Pro Thr Gly Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 99
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 99

Ser Gln Glu Pro Pro Ile Ser Leu Asp Leu Pro Thr His Leu Leu Arg
1               5                   10                  15

Glu Val Leu Glu Met Thr Lys Ala Asp Gln Leu Ala Gln Gln Ala His
            20                  25                  30
```

Ser Asn Arg Lys Leu Leu Asp Ile Ala
        35                  40

<210> SEQ ID NO 100
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 100

Ser Gln Glu Pro Pro Ile Ser Leu Asp Leu Pro Ile Gln Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 101
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 101

Ser Gln Glu Pro Pro Ile Ser Leu Asp Leu Pro Leu Tyr Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 102
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 102

Ser Gln Glu Pro Pro Ile Ser Leu Asp Leu Pro Leu His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 103
<211> LENGTH: 41
<212> TYPE: PRT
<213> ORGANISM: Artificial
<220> FEATURE:

```
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 103

Ser Gln Glu Pro Pro Ile Ser Leu Asp Leu Pro Phe Gly Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 104
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 104

Ser Gln Glu Pro Pro Ile Ser Leu Asp Leu Pro Phe His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 105
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 105

Ser Gln Glu Pro Pro Ile Ser Leu Asp Leu Pro Thr Gln Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 106
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 106

Ser Gln Glu Pro Pro Ile Ser Leu Asp Leu Pro Thr Tyr Leu Leu Arg
1               5                   10                  15
```

```
Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 107
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (38)..(38)
<223> OTHER INFORMATION: AMIDATION

<400> SEQUENCE: 107

Ile Val Leu Ser Leu Asp Val Pro Ile Gly Leu Leu Gln Ile Leu Leu
1               5                   10                  15

Glu Gln Glu Lys Ala Arg Ala Ala Arg Glu Gln Ala Thr Thr Asn Ala
            20                  25                  30

Arg Ile Leu Ala Arg Val
        35

<210> SEQ ID NO 108
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 108

Ile Val Leu Ser Leu Asp Val Pro Ile Gly Leu Leu Gln Ile Leu Leu
1               5                   10                  15

Glu Gln Thr Lys Ala Asp Ala Ala Arg Glu Gln Ala Thr Thr Asn Ala
            20                  25                  30

Arg Ile Leu Ala Arg Val
        35

<210> SEQ ID NO 109
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 109

Ile Val Leu Ser Leu Asp Val Pro Ile Gly Leu Leu Gln Ile Leu Leu
1               5                   10                  15

Glu Gln Ala Lys Ala Arg Ala Ala Arg Glu Gln Ala Thr Thr Asn Ala
            20                  25                  30

Arg Ile Leu Ala Arg Val
        35
```

<210> SEQ ID NO 110
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 110

Ile Val Leu Ser Leu Asp Val Pro Ile Gly Leu Leu Gln Ile Leu Leu
1               5                   10                  15

Glu Gln Ala Lys Gln Arg Ala Ala Arg Glu Gln Ala Thr Thr Asn Ala
            20                  25                  30

Arg Ile Leu Ala Arg Val
        35

<210> SEQ ID NO 111
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 111

Ile Val Leu Ser Leu Asp Val Pro Ile Gly Leu Leu Gln Ile Leu Leu
1               5                   10                  15

Glu Gln Glu Arg Gln Arg Ala Ala Arg Glu Gln Ala Thr Thr Asn Ala
            20                  25                  30

Arg Ile Leu Ala Arg Val
        35

<210> SEQ ID NO 112
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 112

Ile Val Leu Ser Leu Asp Val Pro Ile Gly Leu Leu Gln Ile Leu Leu
1               5                   10                  15

Glu Gln Ala Lys Ala Glu Ala Ala Arg Glu Gln Ala Thr Thr Asn Ala
            20                  25                  30

Arg Ile Leu Ala Arg Val
        35

<210> SEQ ID NO 113
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES

```
<222> LOCATION: (38)..(38)
<223> OTHER INFORMATION: AMIDATION

<400> SEQUENCE: 113

Ile Val Leu Ser Leu Asp Val Pro Ile Gly Leu Leu Gln Ile Leu Leu
1               5                   10                  15

Glu Gln Glu Arg Ala Glu Ala Ala Arg Glu Gln Ala Thr Thr Asn Ala
            20                  25                  30

Arg Ile Leu Ala Arg Val
        35

<210> SEQ ID NO 114
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 114

Ile Val Leu Ser Leu Asp Val Pro Ile Gly Leu Leu Gln Ile Leu Leu
1               5                   10                  15

Glu Gln Ala Arg Gln Arg Ala Ala Arg Glu Gln Ala Thr Thr Asn Ala
            20                  25                  30

Arg Ile Leu Ala Arg Val
        35

<210> SEQ ID NO 115
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 115

Ile Val Leu Ser Leu Asp Val Pro Ile Gly Leu Leu Gln Ile Leu Leu
1               5                   10                  15

Glu Gln Glu Lys Gln Arg Ala Ala Arg Glu Gln Ala Thr Thr Asn Ala
            20                  25                  30

Arg Ile Leu Ala Arg Val
        35

<210> SEQ ID NO 116
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 116

Ile Val Leu Ser Leu Asp Val Pro Ile Gly Leu Leu Gln Ile Leu Leu
1               5                   10                  15

Glu Gln Thr Lys Ala Asn Ala Ala Arg Glu Gln Ala Thr Thr Val Ala
            20                  25                  30
```

Arg Ile Leu Ala Arg Val
        35

<210> SEQ ID NO 117
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 117

Ile Val Leu Ser Leu Asp Val Pro Ile Gly Leu Leu Gln Ile Leu Leu
1               5                   10                  15

Glu Gln Thr Lys Ala Arg Ala Ala Arg Glu Gln Ala Thr Thr Asn Ala
                20                  25                  30

Arg Ile Leu Ala Arg Val
        35

<210> SEQ ID NO 118
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 118

Ile Val Leu Ser Leu Asp Val Pro Ile Gly Leu Leu Gln Ile Leu Leu
1               5                   10                  15

Glu Gln Glu Arg Gln Glu Ala Ala Arg Glu Gln Ala Thr Thr Asn Ala
                20                  25                  30

Arg Ile Leu Ala Arg Val
        35

<210> SEQ ID NO 119
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 119

Ile Val Leu Ser Leu Asp Val Pro Ile Gly Leu Leu Gln Ile Leu Leu
1               5                   10                  15

Glu Gln Glu Arg Ala Arg Ala Ala Arg Glu Gln Ala Thr Thr Asn Ala
                20                  25                  30

Arg Ile Leu Ala Arg Val
        35

<210> SEQ ID NO 120
<211> LENGTH: 38
<212> TYPE: PRT
<213> ORGANISM: Artificial
<220> FEATURE:

```
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 120

Ile Val Leu Ser Leu Glu Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 121
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 121

Ile Val Leu Ser Leu Asp Val Pro Ile Gly Leu Leu Gln Ile Leu Leu
1               5                   10                  15

Glu Gln Glu Lys Ala Arg Ala Ala Arg Glu Gln Ala Thr Thr Asn Ala
            20                  25                  30

Arg Ile Leu Ala Arg Val
        35

<210> SEQ ID NO 122
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 122

Ile Val Leu Ser Leu Asp Val Pro Ile Gly Leu Leu Gln Ile Leu Leu
1               5                   10                  15

Glu Gln Ala Arg Ala Glu Ala Ala Arg Glu Gln Ala Thr Thr Asn Ala
            20                  25                  30

Arg Ile Leu Ala Arg Val
        35

<210> SEQ ID NO 123
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 123

Ile Val Leu Ser Leu Asp Val Pro Ile Gly Leu Leu Gln Ile Leu Leu
1               5                   10                  15
```

-continued

```
Glu Gln Ala Arg Gln Glu Ala Ala Arg Glu Gln Ala Thr Thr Asn Ala
        20                  25                  30

Arg Ile Leu Ala Arg Val
        35

<210> SEQ ID NO 124
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 124

Ile Val Leu Ser Leu Asp Val Pro Ile Gly Leu Leu Gln Ile Leu Leu
1               5                   10                  15

Glu Gln Ala Lys Gln Glu Ala Ala Arg Glu Gln Ala Thr Thr Asn Ala
        20                  25                  30

Arg Ile Leu Ala Arg Val
        35

<210> SEQ ID NO 125
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 125

Ile Val Leu Ser Leu Asp Val Pro Ile Gly Leu Leu Gln Ile Leu Leu
1               5                   10                  15

Glu Gln Glu Lys Gln Glu Ala Ala Arg Glu Gln Ala Thr Thr Asn Ala
        20                  25                  30

Arg Ile Leu Ala Arg Val
        35

<210> SEQ ID NO 126
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 126

Ile Val Leu Ser Leu Asp Val Pro Ile Gly Leu Leu Gln Ile Leu Leu
1               5                   10                  15

Glu Gln Thr Arg Ala Asp Ala Ala Arg Glu Gln Ala Thr Thr Asn Ala
        20                  25                  30

Arg Ile Leu Ala Arg Val
        35

<210> SEQ ID NO 127
<211> LENGTH: 38
```

<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 127

Ile Val Leu Ser Leu Asp Val Pro Ile Gly Leu Leu Gln Ile Leu Leu
1               5                   10                  15

Glu Gln Ala Lys Ala Arg Ala Ala Arg Glu Gln Ala Thr Thr Asn Ala
            20                  25                  30

Arg Ile Leu Ala Arg Val
        35

<210> SEQ ID NO 128
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 128

Ile Val Leu Ser Leu Asp Val Pro Ile Gly Leu Leu Gln Ile Leu Leu
1               5                   10                  15

Glu Gln Thr Arg Ala Arg Ala Ala Arg Glu Gln Ala Thr Thr Asn Ala
            20                  25                  30

Arg Ile Leu Ala Arg Val
        35

<210> SEQ ID NO 129
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 129

Ile Val Leu Ser Leu Asp Val Pro Ile Gly Leu Leu Gln Ile Leu Leu
1               5                   10                  15

Glu Gln Thr Lys Ala Arg Ala Ala Arg Glu Gln Ala Thr Thr Asn Ala
            20                  25                  30

Arg Ile Leu Ala Arg Val
        35

<210> SEQ ID NO 130
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 130

Ile Val Leu Ser Leu Asp Val Pro Ile Gly Leu Leu Gln Ile Leu Leu
1               5                   10                  15

Glu Gln Ala Arg Ala Asp Ala Ala Arg Glu Gln Ala Thr Thr Asn Ala
            20                  25                  30

Arg Ile Leu Ala Arg Val
            35

<210> SEQ ID NO 131
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 131

Ile Val Leu Ser Leu Asp Val Pro Ile Gly Leu Leu Gln Ile Leu Leu
1               5                   10                  15

Glu Gln Ala Lys Ala Asp Ala Ala Arg Glu Gln Ala Thr Thr Asn Ala
            20                  25                  30

Arg Ile Leu Ala Arg Val
            35

<210> SEQ ID NO 132
<211> LENGTH: 35
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (35)..(35)
<223> OTHER INFORMATION: AMIDATION

<400> SEQUENCE: 132

Ile Val Leu Ser Leu Asp Val Pro Ile Gly Leu Leu Gln Ile Leu Leu
1               5                   10                  15

Glu Gln Glu Lys Glu Lys Lys Arg Lys Glu Thr Asn Ala Arg Ile Leu
            20                  25                  30

Ala Arg Val
        35

<210> SEQ ID NO 133
<211> LENGTH: 36
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (36)..(36)
<223> OTHER INFORMATION: AMIDATION

<400> SEQUENCE: 133

Ile Val Leu Ser Leu Asp Val Pro Ile Gly Leu Leu Gln Ile Leu Leu
1               5                   10                  15

Glu Gln Arg Arg Ala Ala Arg Glu Gln Ala Thr Thr Asn Ala Arg Ile
            20                  25                  30

Leu Ala Arg Val
        35

<210> SEQ ID NO 134
<211> LENGTH: 36
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (36)..(36)
<223> OTHER INFORMATION: AMIDATION

<400> SEQUENCE: 134

Ile Val Leu Ser Leu Asp Val Pro Ile Gly Leu Leu Gln Ile Leu Leu
1               5                   10                  15

Glu Gln Ala Ala Ala Ala Arg Glu Gln Ala Thr Thr Asn Ala Arg Ile
            20                  25                  30

Leu Ala Arg Val
        35

<210> SEQ ID NO 135
<211> LENGTH: 37
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (37)..(37)
<223> OTHER INFORMATION: AMIDATION

<400> SEQUENCE: 135

Ile Val Leu Ser Leu Asp Val Pro Ile Gly Leu Leu Gln Ile Leu Leu
1               5                   10                  15

Glu Gln Ala Ala Arg Ala Ala Arg Glu Gln Ala Thr Thr Asn Ala Arg
            20                  25                  30

Ile Leu Ala Arg Val
        35

<210> SEQ ID NO 136
<211> LENGTH: 35
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (35)..(35)
<223> OTHER INFORMATION: AMIDATION

<400> SEQUENCE: 136

Ile Val Leu Ser Leu Asp Val Pro Ile Gly Leu Leu Gln Ile Leu Leu
1               5                   10                  15

Glu Gln Arg Ala Ala Arg Glu Gln Ala Thr Thr Asn Ala Arg Ile Leu
            20                  25                  30

Ala Arg Val
        35

<210> SEQ ID NO 137
<211> LENGTH: 37
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (37)..(37)

```
<223> OTHER INFORMATION: AMIDATION

<400> SEQUENCE: 137

Ile Val Leu Ser Leu Asp Val Pro Ile Gly Leu Leu Gln Ile Leu Leu
1               5                   10                  15

Glu Gln Arg Ala Arg Ala Ala Arg Glu Gln Ala Thr Thr Asn Ala Arg
            20                  25                  30

Ile Leu Ala Arg Val
        35

<210> SEQ ID NO 138
<211> LENGTH: 34
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (34)..(34)
<223> OTHER INFORMATION: AMIDATION

<400> SEQUENCE: 138

Ile Val Leu Ser Leu Asp Val Pro Ile Gly Leu Leu Gln Ile Leu Leu
1               5                   10                  15

Glu Gln Ala Ala Arg Glu Gln Ala Thr Thr Asn Ala Arg Ile Leu Ala
            20                  25                  30

Arg Val

<210> SEQ ID NO 139
<211> LENGTH: 35
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (35)..(35)
<223> OTHER INFORMATION: AMIDATION

<400> SEQUENCE: 139

Ile Val Leu Ser Leu Asp Val Pro Ile Gly Leu Leu Gln Ile Leu Leu
1               5                   10                  15

Glu Gln Ala Ala Ala Arg Glu Gln Ala Thr Thr Asn Ala Arg Ile Leu
            20                  25                  30

Ala Arg Val
        35

<210> SEQ ID NO 140
<211> LENGTH: 36
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (36)..(36)
<223> OTHER INFORMATION: AMIDATION

<400> SEQUENCE: 140

Ile Val Leu Ser Leu Asp Val Pro Ile Gly Leu Leu Gln Ile Leu Leu
1               5                   10                  15

Glu Gln Ala Arg Ala Ala Arg Glu Gln Ala Thr Thr Asn Ala Arg Ile
            20                  25                  30

Leu Ala Arg Val
```

<210> SEQ ID NO 141
<211> LENGTH: 37
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (37)..(37)
<223> OTHER INFORMATION: AMIDATION

<400> SEQUENCE: 141

Ile Val Leu Ser Leu Asp Val Pro Ile Gly Leu Leu Gln Ile Leu Leu
1               5                   10                  15

Glu Gln Ala Arg Ala Ala Ala Arg Glu Gln Ala Thr Thr Asn Ala Arg
            20                  25                  30

Ile Leu Ala Arg Val
            35

<210> SEQ ID NO 142
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 142

Glx Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
            35                  40

<210> SEQ ID NO 143
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 143

Glx Gly Pro Pro Ile Ser Ile Asp Leu Pro Leu Glu Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
            35                  40

```
<210> SEQ ID NO 144
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 144

Glx Gly Pro Pro Ile Ser Ile Asp Leu Pro Leu Gln Leu Leu Arg Lys
 1               5                  10                  15

Met Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 145
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 145

Glx Gly Pro Pro Ile Ser Ile Asp Leu Pro Leu His Leu Leu Arg Lys
 1               5                  10                  15

Met Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 146
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 146

Glx Gly Pro Pro Ile Ser Ile Asp Leu Pro Phe His Leu Leu Arg Lys
 1               5                  10                  15

Met Ile Glu Ile Glu Lys Gln Glu Lys Glu Lys Gln Gln Ala Thr Thr
            20                  25                  30

Asn Ala Arg Ile Leu Ala Arg Val
```

<210> SEQ ID NO 147
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 147

Glx Gly Pro Pro Ile Ser Ile Asp Leu Pro Phe Tyr Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
            35                  40

<210> SEQ ID NO 148
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 148

Glx Gly Pro Pro Ile Ser Ile Asp Leu Pro Phe Gln Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
            35                  40

<210> SEQ ID NO 149
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 149

Glx Gly Pro Pro Ile Ser Ile Asp Leu Pro Ile Tyr Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 150
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 150

Glx Gly Pro Pro Ile Ser Ile Asp Leu Pro Ile Gln Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 151
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 151

Glx Gly Pro Pro Ile Ser Ile Asp Leu Pro Thr Tyr Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 152
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 152

Ser Gln Glu Ile Val Leu Ser Leu Asp Val Pro Ile Gly Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala

<210> SEQ ID NO 153
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 153

Glx Gly Ile Val Leu Ser Leu Asp Val Pro Ile Gly Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 154
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 154

Ile Val Leu Ser Leu Asp Val Pro Ile Gly Leu Leu Gln Ile Leu Ile
1               5                   10                  15

Glu Ile Glu Lys Gln Glu Lys Glu Lys Gln Gln Ala Ala Asn Asn Arg
            20                  25                  30

Leu Leu Leu Asp Thr Ile
            35

<210> SEQ ID NO 155
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 155

Ile Val Leu Ser Leu Asp Val Pro Ile Gly Leu Leu Gln Ile Leu Leu
1               5                   10                  15

Glu Met Thr Lys Ala Asp Gln Leu Ala Gln Gln Ala His Ser Asn Arg
            20                  25                  30

Lys Leu Leu Asp Ile Ala
            35

<210> SEQ ID NO 156
<211> LENGTH: 40
<212> TYPE: PRT

```
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 156

Glx Gly Pro Pro Ile Ser Ile Asp Leu Ser Leu Glu Leu Leu Arg Lys
1               5                   10                  15

Met Ile Glu Gln Ala Arg Ala Arg Ala Ala Arg Glu Gln Ala Thr Thr
            20                  25                  30

Asn Ala Arg Ile Leu Ala Arg Val
        35                  40

<210> SEQ ID NO 157
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 157

Ser Gln Glu Pro Pro Ile Ser Leu Asp Leu Thr Phe His Leu Leu Arg
1               5                   10                  15

Glu Val Leu Glu Gln Ala Arg Ala Arg Ala Ala Arg Glu Gln Ala Thr
            20                  25                  30

Thr Asn Ala Arg Ile Leu Ala Arg Val
        35                  40

<210> SEQ ID NO 158
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 158

Ile Val Leu Ser Leu Asp Val Pro Ile Gly Leu Leu Gln Ile Leu Leu
1               5                   10                  15

Glu Ile Glu Lys Gln Glu Lys Glu Lys Gln Gln Ala Ala Asn Asn Arg
            20                  25                  30

Leu Leu Leu Asp Thr Ile
        35

<210> SEQ ID NO 159
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
```

<223> OTHER INFORMATION: AMIDATION

<400> SEQUENCE: 159

Ile Val Leu Ser Leu Asp Val Pro Ile Gly Leu Leu Gln Ile Leu Leu
1               5                   10                  15

Glu Gln Thr Lys Ala Asp Gln Leu Ala Gln Gln Ala His Ser Asn Arg
            20                  25                  30

Lys Leu Leu Asp Ile Ala
            35

<210> SEQ ID NO 160
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 160

Ile Val Leu Ser Leu Asp Val Pro Ile Gly Leu Leu Gln Thr Leu Leu
1               5                   10                  15

Glu Leu Ala Arg Thr Gln Ser Gln Arg Glu Arg Ala Glu Gln Asn Arg
            20                  25                  30

Ile Ile Phe Asp Ser Val
            35

<210> SEQ ID NO 161
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 161

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Thr Asn Ala Arg Ile Leu Ala Arg Val
            35                  40

<210> SEQ ID NO 162
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 162

Ser Glu Glu Pro Pro Ile Ser Leu Asp Val Pro Ile Gly Leu Leu Gln
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 163
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 163

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Ser Asn Arg
            20                  25                  30

Lys Leu Met Glu Ile Ile
        35

<210> SEQ ID NO 164
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 164

Ile Val Leu Ser Leu Asp Val Pro Ile Gly Leu Leu Gln Ile Leu Leu
1               5                   10                  15

Glu Met Ala Arg Ala Glu Gln Leu Ala Gln Gln Ala His Ser Asn Arg
            20                  25                  30

Lys Leu Met Glu Ile Ile
        35

<210> SEQ ID NO 165
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 165

Ile Val Leu Ser Leu Asp Val Pro Ile Gly Leu Leu Gln Val Leu
1               5                   10                  15

Glu Met Ala Arg Ala Glu Gln Leu Ala Gln Gln Ala His Ser Asn Arg
            20                  25                  30

Lys Leu Met Glu Ile Ile
        35

<210> SEQ ID NO 166
<211> LENGTH: 38
<212> TYPE: PRT
<213> ORGANISM: Artificial
<220> FEATURE:
<223> OTHER INFORMATION: Chemically synthesized artificial peptide

```
<220> FEATURE:
<221> NAME/KEY: MOD_RES
<222> LOCATION: (38)..(38)
<223> OTHER INFORMATION: AMIDATION

<400> SEQUENCE: 166

Ile Val Leu Ser Leu Asp Val Pro Ile Gly Leu Leu Gln Ile Leu Ile
1               5                   10                  15

Glu Ile Glu Lys Gln Glu Lys Glu Lys Gln Gln Ala Ala Asn Asn Ala
            20                  25                  30

Arg Ile Leu Ala Arg Val
        35

<210> SEQ ID NO 167
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 167

Ile Val Leu Ser Leu Asp Val Pro Ile Gly Leu Leu Gln Ile Leu Leu
1               5                   10                  15

Glu Gln Glu Lys Gln Glu Lys Glu Lys Gln Gln Ala Thr Thr Asn Ala
            20                  25                  30

Arg Ile Leu Ala Arg Val
        35

<210> SEQ ID NO 168
<211> LENGTH: 39
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (39)..(39)
<223> OTHER INFORMATION: AMIDATION

<400> SEQUENCE: 168

Ile Val Leu Ser Leu Asp Val Pro Ile Gly Leu Leu Gln Ile Leu Ile
1               5                   10                  15

Glu Ile Glu Lys Gln Glu Lys Glu Lys Gln Gln Ala Ala Thr Thr Asn
            20                  25                  30

Ala Arg Ile Leu Ala Arg Val
        35

<210> SEQ ID NO 169
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 169
```

```
Glx Gly Pro Pro Ile Ser Ile Asp Val Pro Thr Tyr Leu Leu Arg Ile
1               5                   10                  15

Leu Ile Glu Ile Glu Lys Gln Glu Lys Gln Gln Ala Thr Thr
            20                  25                  30

Asn Ala Arg Ile Leu Ala Arg Val
        35                  40

<210> SEQ ID NO 170
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 170

Glx Gly Pro Pro Ile Ser Ile Asp Val Pro Thr Tyr Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 171
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 171

Glx Gly Pro Pro Ile Ser Ile Asp Val Pro Phe Gln Leu Leu Arg Ile
1               5                   10                  15

Leu Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 172
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION
```

-continued

<400> SEQUENCE: 172

Glx Gly Pro Pro Ile Ser Ile Asp Val Pro Phe Gln Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 173
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 173

Asp Asn Pro Ser Leu Ser Ile Asp Leu Pro Thr Tyr Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
        35                  40

<210> SEQ ID NO 174
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 174

Asp Asn Pro Ser Leu Ser Ile Asp Leu Pro Leu Leu Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
        35                  40

<210> SEQ ID NO 175
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 175

Asp Asn Pro Ser Leu Ser Ile Asp Leu Pro Leu Ile Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val

<210> SEQ ID NO 176
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 176

Asp Asn Pro Ser Leu Ser Ile Asp Leu Pro Leu Gln Leu Leu Arg Thr
1               5                   10                  15
Leu Leu Glu Leu Ala Arg Thr Gln Ser Gln Arg Glu Arg Ala Glu Gln
            20                  25                  30
Asn Ala Ile Ile Phe Ala Ser Val
            35                  40

<210> SEQ ID NO 177
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 177

Asp Asn Pro Ser Leu Ser Ile Asp Leu Pro Leu Tyr Leu Leu Arg Thr
1               5                   10                  15
Leu Leu Glu Leu Ala Arg Thr Gln Ser Gln Arg Glu Arg Ala Glu Gln
            20                  25                  30
Asn Ala Ile Ile Phe Ala Ser Val
            35                  40

<210> SEQ ID NO 178
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 178

Asp Asn Pro Ser Leu Ser Ile Asp Leu Pro Leu Phe Leu Leu Arg Thr
1               5                   10                  15
Leu Leu Glu Leu Ala Arg Thr Gln Ser Gln Arg Glu Arg Ala Glu Gln
            20                  25                  30
Asn Ala Ile Ile Phe Ala Ser Val
            35                  40

<210> SEQ ID NO 179
<211> LENGTH: 40
<212> TYPE: PRT
<213> ORGANISM: Artificial
<220> FEATURE:
<223> OTHER INFORMATION: Chemically synthesized artificial peptide
<220> FEATURE:

<221> NAME/KEY: MOD_RES
<222> LOCATION: (40)..(40)
<223> OTHER INFORMATION: AMIDATION

<400> SEQUENCE: 179

Asp Asn Pro Ser Leu Ser Ile Asp Leu Pro Leu His Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
        35                  40

<210> SEQ ID NO 180
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 180

Asp Asn Pro Ser Leu Ser Ile Asp Leu Pro Phe Leu Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
        35                  40

<210> SEQ ID NO 181
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 181

Asp Asn Pro Ser Leu Ser Ile Asp Leu Pro Phe Ile Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
        35                  40

<210> SEQ ID NO 182
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 182

Asp Asn Pro Ser Leu Ser Ile Asp Leu Pro Phe Gln Leu Leu Arg Thr
1               5                   10                  15

Leu Leu Glu Leu Ala Arg Thr Gln Ser Gln Arg Glu Arg Ala Glu Gln

```
                    20                  25                  30

Asn Ala Ile Ile Phe Ala Ser Val
            35                  40

<210> SEQ ID NO 183
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 183

Asp Asn Pro Ser Leu Ser Ile Asp Leu Pro Phe Tyr Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
            35                  40

<210> SEQ ID NO 184
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 184

Asp Asn Pro Ser Leu Ser Ile Asp Leu Pro Phe Phe Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
            35                  40

<210> SEQ ID NO 185
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 185

Asp Asn Pro Ser Leu Ser Ile Asp Leu Pro Phe His Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
            35                  40

<210> SEQ ID NO 186
<211> LENGTH: 40
<212> TYPE: PRT
<213> ORGANISM: Artificial
```

```
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 186

Glx Gly Pro Pro Ile Ser Ile Asp Leu Pro His Trp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 187
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 187

Glx Gly Pro Pro Ile Ser Ile Asp Leu Pro Trp Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 188
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 188

Glx Gly Pro Pro Ile Ser Ile Asp Leu Pro Leu Leu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 189
<211> LENGTH: 40
```

```
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 189

Glx Gly Pro Pro Ile Ser Ile Asp Leu Pro Phe Ile Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 190
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 190

Glx Gly Pro Pro Ile Ser Ile Asp Leu Pro Phe Val Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 191
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 191

Glx Gly Pro Pro Ile Ser Ile Asp Leu Pro Phe Leu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40
```

```
<210> SEQ ID NO 192
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 192

Glx Gly Pro Pro Ile Ser Ile Asp Leu Pro Ile Trp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 193
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 193

Glx Gly Pro Pro Ile Ser Ile Asp Leu Pro Leu Val Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 194
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 194

Glx Gly Pro Pro Ile Ser Ile Asp Leu Pro Leu Ile Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40
```

<210> SEQ ID NO 195
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 195

Glx Gly Pro Pro Ile Ser Ile Asp Leu Pro Leu Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 196
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 196

Glx Gly Pro Pro Ile Ser Ile Asp Leu Pro Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 197
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 197

Glx Gly Pro Pro Ile Ser Ile Asp Leu Pro Gln Val Leu Leu Arg Lys
1               5                   10                  15

Met Ile Glu Ile Glu Lys Gln Glu Lys Glu Lys Gln Gln Ala Ala Asn
            20                  25                  30

```
Asn Arg Leu Leu Leu Asp Thr Ile
        35                  40

<210> SEQ ID NO 198
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 198

Glx Gly Pro Pro Ile Ser Ile Asp Leu Pro Gln Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 199
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 199

Glx Gly Pro Pro Ile Ser Ile Asp Leu Pro Gln Ile Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 200
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 200

Glx Gly Pro Pro Ile Ser Ile Asp Leu Pro Tyr Thr Leu Leu Arg Lys
1               5                   10                  15

Met Ile Glu Ile Glu Lys Gln Glu Lys Glu Lys Gln Gln Ala Ala Asn
```

```
                    20                  25                  30

Asn Arg Leu Leu Leu Asp Thr Ile
        35                  40

<210> SEQ ID NO 201
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 201

Glx Gly Pro Pro Ile Ser Ile Asp Leu Pro Tyr Val Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 202
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 202

Glx Gly Pro Pro Ile Ser Ile Asp Leu Pro Tyr Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 203
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 203

Glx Gly Pro Pro Ile Ser Ile Asp Leu Pro Tyr Leu Leu Leu Arg Lys
1               5                   10                  15
```

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 204
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 204

Glx Gly Pro Pro Ile Ser Ile Asp Leu Pro Tyr Ile Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 205
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 205

Glx Gly Pro Pro Ile Ser Ile Asp Leu Pro His His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 206
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 206

Glx Gly Pro Pro Ile Ser Ile Asp Leu Pro Ala His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 207
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 207

Glx Gly Pro Pro Ile Ser Ile Asp Leu Pro Gln His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 208
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 208

Glx Gly Pro Pro Ile Ser Ile Asp Leu Pro Tyr His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 209
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION -continued

```
<400> SEQUENCE: 209

Glx Gly Pro Pro Ile Ser Ile Asp Leu Pro Trp His Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 210
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 210

Glx Gly Pro Pro Ile Ser Ile Asp Leu Pro Trp Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 211
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 211

Glx Gly Pro Pro Ile Ser Ile Asp Leu Pro Ala Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 212
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
```

<223> OTHER INFORMATION: AMIDATION

<400> SEQUENCE: 212

Glx Gly Pro Pro Ile Ser Ile Asp Leu Pro His Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 213
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 213

Glx Gly Pro Pro Ile Ser Ile Asp Leu Pro Gln Trp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 214
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 214

Ile Val Leu Ser Leu Asp Val Val Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 215
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION -continued

```
<400> SEQUENCE: 215

Glx Gly Pro Pro Ile Ser Ile Asp Leu Pro Tyr Trp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 216
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 216

Glx Gly Pro Pro Ile Ser Ile Asp Leu Pro Trp Trp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 217
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 217

Glx Gly Pro Pro Ile Ser Ile Asp Leu Pro Phe Trp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 218
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
```

<223> OTHER INFORMATION: AMIDATION

<400> SEQUENCE: 218

Glx Gly Pro Pro Ile Ser Ile Asp Leu Pro Leu Trp Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 219
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 219

Glx Gly Pro Pro Ile Ser Ile Asp Leu Pro His Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 220
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 220

Glx Gly Pro Pro Ile Ser Ile Asp Leu Pro Tyr Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 221
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:

<221> NAME/KEY: MOD_RES
<222> LOCATION: (40)..(40)
<223> OTHER INFORMATION: AMIDATION

<400> SEQUENCE: 221

Glx Gly Pro Pro Ile Ser Ile Asp Leu Pro Gln Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 222
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 222

Glx Gly Pro Pro Ile Ser Ile Asp Leu Pro Ala Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 223
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 223

Glx Gly Pro Pro Ile Ser Ile Asp Leu Pro Phe Phe Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 224
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)

<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 224

Glx Gly Pro Pro Ile Ser Ile Asp Leu Pro Gln Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 225
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 225

Glx Gly Pro Pro Ile Ser Ile Asp Leu Pro Tyr Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 226
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 226

Glx Gly Pro Pro Ile Ser Ile Asp Leu Pro Tyr Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 227
<211> LENGTH: 40
<212> TYPE: PRT
<213> ORGANISM: Artificial
<220> FEATURE:
<223> OTHER INFORMATION: Chemically synthesized artificial peptide
<220> FEATURE:

<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 227

Glx Gly Pro Pro Ile Ser Ile Asp Leu Pro Gln Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 228
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 228

Glx Gly Pro Pro Ile Ser Ile Asp Leu Pro Phe His Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 229
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 229

Glx Gly Pro Pro Ile Ser Ile Asp Leu Pro Phe His Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 230
<211> LENGTH: 40
<212> TYPE: PRT
<213> ORGANISM: Artificial
<220> FEATURE:

```
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 230

Glx Gly Pro Pro Ile Ser Ile Asp Leu Pro Phe Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 231
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 231

Glx Gly Pro Pro Ile Ser Ile Asp Leu Pro Phe Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 232
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 232

Glx Gly Pro Pro Ile Ser Ile Asp Leu Pro Thr Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 233
<211> LENGTH: 40
<212> TYPE: PRT
```

-continued

```
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (1)..(40)
<223> OTHER INFORMATION: AMIDATION

<400> SEQUENCE: 233

Glx Gly Pro Pro Ile Ser Ile Asp Leu Pro Thr Tyr Leu Leu Arg Lys
 1               5                  10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 234
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 234

Glx Gly Pro Pro Ile Ser Ile Asp Leu Pro Leu Glu Leu Leu Arg Lys
 1               5                  10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 235
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 235

Glx Gly Pro Pro Ile Ser Ile Asp Leu Pro Leu Glu Leu Leu Arg Lys
 1               5                  10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 236
```

```
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 236

Glx Gly Pro Pro Ile Ser Ile Asp Leu Pro Ile Tyr Leu Leu Arg Lys
 1               5                  10                  15

Met Ile Glu Ile Glu Lys Gln Glu Lys Glu Lys Gln Gln Ala Ala Asn
             20                  25                  30

Asn Ala Leu Leu Leu Asp Thr Ile
         35                  40

<210> SEQ ID NO 237
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 237

Glx Gly Pro Pro Ile Ser Ile Asp Leu Pro Ile Tyr Leu Leu Arg Lys
 1               5                  10                  15

Met Ile Glu Ile Glu Lys Gln Glu Lys Glu Lys Gln Gln Ala Ala Asn
             20                  25                  30

Asn Ala Leu Leu Leu Ala Thr Ile
         35                  40

<210> SEQ ID NO 238
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 238

Glx Gly Pro Pro Ile Ser Ile Asp Leu Pro Leu His Leu Leu Arg Lys
 1               5                  10                  15

Met Ile Glu Ile Glu Lys Gln Glu Lys Glu Lys Gln Gln Ala Thr Thr
             20                  25                  30

Asn Ala Arg Leu Leu Asp Thr Val
         35                  40
```

<210> SEQ ID NO 239
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 239

Glx Gly Pro Pro Ile Ser Ile Asp Leu Pro Leu His Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Leu Leu Asp Arg Val
        35                  40

<210> SEQ ID NO 240
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 240

Glx Gly Pro Pro Ile Ser Ile Asp Leu Pro Leu His Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 241
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 241

Glx Gly Pro Pro Ile Ser Ile Asp Leu Pro Leu His Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile 35          40

<210> SEQ ID NO 242
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 242

Glx Gly Pro Pro Ile Ser Ile Asp Leu Pro Leu Tyr Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Leu Leu Asp Thr Val
        35                  40

<210> SEQ ID NO 243
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 243

Glx Gly Pro Pro Ile Ser Ile Asp Leu Pro Leu Tyr Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Leu Leu Asp Arg Val
        35                  40

<210> SEQ ID NO 244
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 244

Glx Gly Pro Pro Ile Ser Ile Asp Leu Pro Leu Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
            35                  40

<210> SEQ ID NO 245
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 245

Glx Gly Pro Pro Ile Ser Ile Asp Leu Pro Leu Tyr Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile
            35                  40

<210> SEQ ID NO 246
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 246

Glx Gly Pro Pro Ile Ser Ile Asp Leu Pro Leu Gln Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Leu Leu Asp Thr Val
            35                  40

<210> SEQ ID NO 247
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 247

Glx Gly Pro Pro Ile Ser Ile Asp Leu Pro Leu Gln Leu Leu Glu Lys
1               5                   10                  15

```
Met Ile Glu Ile Glu Lys Gln Glu Lys Glu Lys Gln Gln Ala Thr Thr
            20                  25                  30

Asn Ala Arg Leu Leu Asp Arg Val
        35                  40
```

<210> SEQ ID NO 248
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 248

```
Glx Gly Pro Pro Ile Ser Ile Asp Leu Pro Leu Gln Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40
```

<210> SEQ ID NO 249
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 249

```
Glx Gly Pro Pro Ile Ser Ile Asp Leu Pro Leu Gln Leu Leu Glu Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40
```

<210> SEQ ID NO 250
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 250

Glx Gly Pro Pro Ile Ser Ile Asp Leu Pro Phe Gln Leu Leu Arg Lys

```
                 1               5                  10                 15
Met Ile Glu Ile Glu Lys Gln Glu Lys Glu Lys Gln Gln Ala Ala Asn
                 20                 25                 30

Asn Arg Leu Leu Leu Ala Thr Ile
        35                  40

<210> SEQ ID NO 251
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 251

Glx Gly Pro Pro Ile Ser Ile Asp Leu Pro Phe Gln Leu Leu Arg Lys
1               5                  10                 15

Met Ile Glu Ile Glu Lys Gln Glu Lys Glu Lys Gln Gln Ala Ala Asn
                 20                 25                 30

Asn Ala Leu Leu Leu Asp Thr Ile
        35                  40

<210> SEQ ID NO 252
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 252

Glx Gly Pro Pro Ile Ser Ile Asp Leu Pro Thr Tyr Leu Leu Arg Ile
1               5                  10                 15

Leu Ile Glu Ile Glu Lys Gln Glu Lys Glu Lys Gln Gln Ala Ala Asn
                 20                 25                 30

Asn Arg Leu Leu Leu Asp Thr Ile
        35                  40

<210> SEQ ID NO 253
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 253
```

-continued

Glx Gly Pro Pro Ile Ser Ile Asp Val Pro Thr Tyr Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 254
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 254

Glx Gly Pro Pro Ile Ser Ile Asp Val Pro Ile Gly Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 255
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 255

Glx Gly Pro Pro Ile Ser Ile Asp Leu Pro Phe Gln Leu Leu Arg Ile
1               5                   10                  15

Leu Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 256
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 256

Glx Gly Pro Pro Ile Ser Ile Asp Val Pro Phe Gln Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 257
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 257

Asn Asp Asp Pro Pro Ile Ser Ile Asp Leu Pro Leu Phe Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
        35                  40

<210> SEQ ID NO 258
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 258

Asn Asp Asp Pro Pro Ile Ser Ile Asp Leu Pro Phe Gln Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
        35                  40

<210> SEQ ID NO 259
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 259

Asn Asp Asp Pro Pro Ile Ser Ile Asp Leu Pro Leu His Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val 35                  40

<210> SEQ ID NO 260
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 260

Asn Asp Asp Pro Pro Ile Ser Ile Asp Leu Pro Phe Leu Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
            35                  40

<210> SEQ ID NO 261
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 261

Asn Asp Asp Pro Pro Ile Ser Ile Asp Leu Pro Phe Tyr Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
            35                  40

<210> SEQ ID NO 262
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 262

Asn Asp Asp Pro Pro Ile Ser Ile Asp Leu Pro Phe His Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
            35                  40

<210> SEQ ID NO 263
<211> LENGTH: 40
<212> TYPE: PRT
<213> ORGANISM: Artificial
<220> FEATURE:
<223> OTHER INFORMATION: Chemically synthesized artificial peptide
<220> FEATURE:

```
<221> NAME/KEY: MOD_RES
<222> LOCATION: (40)..(40)
<223> OTHER INFORMATION: AMIDATION

<400> SEQUENCE: 263

Asp Asn Pro Ser Leu Ser Ile Asp Leu Pro Tyr Tyr Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
        35                  40

<210> SEQ ID NO 264
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 264

Asn Asp Asp Pro Pro Ile Ser Ile Asp Leu Pro Phe Phe Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
        35                  40

<210> SEQ ID NO 265
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 265

Asn Asp Asp Pro Pro Ile Ser Ile Asp Leu Pro Gln Tyr Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
        35                  40

<210> SEQ ID NO 266
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 266

Asn Asp Asp Pro Pro Ile Ser Ile Asp Leu Pro Thr Tyr Leu Leu Arg
1               5                   10                  15

Asn Met Ile Glu Met Ala Arg Ile Glu Asn Glu Arg Glu Gln Ala Gly
```

```
                20                  25                  30

Leu Asn Ala Lys Tyr Leu Ala Glu Val
        35                  40

<210> SEQ ID NO 267
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 267

Asn Asp Asp Pro Pro Ile Ser Ile Asp Leu Pro Tyr Tyr Leu Leu Arg
1               5                   10                  15

Asn Met Ile Glu Met Ala Arg Ile Glu Asn Glu Arg Glu Gln Ala Gly
                20                  25                  30

Leu Asn Ala Lys Tyr Leu Ala Glu Val
        35                  40

<210> SEQ ID NO 268
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 268

Asn Asp Asp Pro Pro Ile Ser Ile Asp Leu Pro Leu Leu Leu Leu Arg
1               5                   10                  15

Asn Met Ile Glu Met Ala Arg Ile Glu Asn Glu Arg Glu Gln Ala Gly
                20                  25                  30

Leu Asn Ala Lys Tyr Leu Ala Glu Val
        35                  40

<210> SEQ ID NO 269
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 269

Asn Asp Asp Pro Pro Ile Ser Ile Asp Leu Pro Leu Ile Leu Leu Arg
1               5                   10                  15

Asn Met Ile Glu Met Ala Arg Ile Glu Asn Glu Arg Glu Gln Ala Gly
                20                  25                  30

Leu Asn Ala Lys Tyr Leu Ala Glu Val
        35                  40

<210> SEQ ID NO 270
<211> LENGTH: 41
<212> TYPE: PRT
<213> ORGANISM: Artificial
```

```
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 270
```

Asn Asp Asp Pro Pro Ile Ser Ile Asp Leu Pro Leu Gln Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
            35                  40

```
<210> SEQ ID NO 271
<211> LENGTH: 41
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (41)..(41)
<223> OTHER INFORMATION: AMIDATION

<400> SEQUENCE: 271
```

Asn Asp Asp Pro Pro Ile Ser Ile Asp Leu Pro Leu Tyr Leu Leu Arg
1               5                   10                  15

Asn Met Ile Glu Met Ala Arg Ile Glu Asn Glu Arg Glu Gln Ala Gly
            20                  25                  30

Leu Asn Ala Lys Tyr Leu Ala Glu Val
            35                  40

```
<210> SEQ ID NO 272
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 272
```

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Glu Leu Leu Ala Glu Ile
            35                  40

```
<210> SEQ ID NO 273
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
```

<220> FEATURE:
<221> NAME/KEY: MOD_RES
<222> LOCATION: (40)..(40)
<223> OTHER INFORMATION: AMIDATION

<400> SEQUENCE: 273

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Gln Leu Leu Ala His Ile
        35                  40

<210> SEQ ID NO 274
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 274

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Lys Leu Leu Ala Lys Ile
        35                  40

<210> SEQ ID NO 275
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 275

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Asn Leu Leu Ala Asn Ile
        35                  40

<210> SEQ ID NO 276
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 276

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Gln Leu Leu Ala Gln Ile
        35                  40

<210> SEQ ID NO 277
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 277

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala His Leu Leu Ala His Ile
        35                  40

<210> SEQ ID NO 278
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 278

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Asp Thr Ile
        35                  40

<210> SEQ ID NO 279
<211> LENGTH: 40
<212> TYPE: PRT
<213> ORGANISM: Artificial
<220> FEATURE:
<223> OTHER INFORMATION: Chemically synthesized artificial peptide

```
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 279

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 280
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 280

Glx Gly Pro Pro Ile Ser Ile Asp Leu Pro Ile Phe Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 281
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 281

Glx Gly Pro Pro Ile Ser Ile Asp Leu Pro Ile Phe Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 282
<211> LENGTH: 40
<212> TYPE: PRT
<213> ORGANISM: Artificial
```

-continued

```
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 282

Glx Gly Pro Pro Ile Ser Ile Asp Leu Pro Ile Phe Leu Leu Arg Lys
1               5                   10                  15

Met Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 283
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 283

Glx Gly Pro Pro Ile Ser Ile Asp Leu Pro Tyr Gln Leu Leu Arg Lys
1               5                   10                  15

Val Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 284
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 284

Glx Gly Pro Pro Ile Ser Ile Asp Leu Pro Thr Trp Leu Leu Arg Lys
1               5                   10                  15

Val Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 285
<211> LENGTH: 40
```

```
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 285

Glx Gly Pro Pro Ile Ser Ile Asp Leu Pro Gln Ile Leu Leu Arg Lys
1               5                  10                  15

Met Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 286
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 286

Glx Gly Pro Pro Ile Ser Ile Asp Leu Pro Tyr Gln Leu Leu Arg Lys
1               5                  10                  15

Val Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 287
<211> LENGTH: 39
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (39)..(39)
<223> OTHER INFORMATION: AMIDATION

<400> SEQUENCE: 287

Glx Gly Pro Pro Ile Ser Ile Asp Leu Pro Tyr Gln Leu Leu Arg Lys
1               5                  10                  15

Met Ile Glu Ile Glu Lys Gln Glu Lys Glu Lys Gln Gln Ala Ala Asn
            20                  25                  30

Asn Ala Arg Leu Leu Ala Arg
        35
```

<210> SEQ ID NO 288
<211> LENGTH: 39
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (39)..(39)
<223> OTHER INFORMATION: AMIDATION

<400> SEQUENCE: 288

Glx Gly Pro Pro Ile Ser Ile Asp Leu Pro Tyr Gln Leu Leu Arg Lys
1               5                   10                  15

Met Ile Glu Ile Glu Lys Gln Glu Lys Glu Lys Gln Gln Ala Ala Asn
            20                  25                  30

Asn Ala Arg Leu Leu Ala Arg
        35

<210> SEQ ID NO 289
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 289

Glx Gly Pro Pro Ile Ser Ile Asp Leu Pro Tyr Trp Leu Leu Arg Lys
1               5                   10                  15

Met Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 290
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 290

Glx Gly Pro Pro Ile Ser Ile Asp Leu Pro Ile Ile Leu Leu Arg Lys
1               5                   10                  15

Met Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 291
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 291

Glx Gly Pro Pro Ile Ser Ile Asp Leu Pro Thr Trp Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 292
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 292

Glx Gly Pro Pro Ile Ser Ile Asp Leu Pro Thr Trp Leu Leu Arg Lys
1               5                   10                  15

Met Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 293
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 293

Glx Gly Pro Pro Ile Ser Ile Asp Leu Pro Gln Ile Leu Leu Arg Lys
1               5                   10                  15

Val Ile Glu Ile Glu Lys Gln Glu Lys Glu Lys Gln Gln Ala Ala Asn
            20                  25                  30

```
Asn Arg Leu Leu Leu Asp Thr Ile
        35                  40
```

<210> SEQ ID NO 294
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 294

```
Glx Gly Pro Pro Ile Ser Ile Asp Leu Pro Gln Ile Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
        35                  40
```

<210> SEQ ID NO 295
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 295

```
Glx Gly Pro Pro Ile Ser Ile Asp Leu Pro Ile Ile Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
        35                  40
```

<210> SEQ ID NO 296
<211> LENGTH: 44
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (44)..(44)
<223> OTHER INFORMATION: AMIDATION

<400> SEQUENCE: 296

```
His His His His His His Ile Val Leu Ser Leu Asp Val Pro Ile Gly
1               5                   10                  15

Leu Leu Gln Ile Leu Leu Glu Gln Ala Arg Ala Arg Ala Ala Arg Glu
            20                  25                  30

Gln Ala Thr Thr Asn Ala Arg Ile Leu Ala Arg Asn
        35                  40
```

<210> SEQ ID NO 297
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 297

Glx Gly Pro Pro Ile Ser Ile Asp Leu Pro Ile Ile Leu Leu Arg Lys
1               5                   10                  15

Val Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 298
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 298

Glx Gly Pro Pro Ile Ser Ile Asp Leu Pro Ile Phe Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 299
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 299

Glx Gly Pro Pro Ile Ser Ile Asp Leu Pro Gln Ile Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 300
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 300

Ile Val Leu Ser Leu Asp Val Pro Ile Gly Leu Leu Gln Lys Val Ile
1               5                   10                  15

Glu Ile Glu Lys Gln Glu Lys Glu Lys Gln Gln Ala Thr Thr Asn Ala
            20                  25                  30

Arg Ile Leu Ala Arg Val
        35

<210> SEQ ID NO 301
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 301

Glx Gly Pro Pro Ile Ser Ile Asp Leu Pro Thr Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 302
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 302

-continued

```
Glx Gly Pro Pro Ile Ser Ile Asp Leu Pro Gln Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 303
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 303

Glx Gly Pro Pro Ile Ser Ile Asp Leu Pro Ala Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 304
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 304

Glx Gly Pro Pro Ile Ser Ile Asp Leu Pro His Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 305
<211> LENGTH: 40
<212> TYPE: PRT
<213> ORGANISM: Artificial
<220> FEATURE:
<223> OTHER INFORMATION: Chemically synthesized artificial peptide
<220> FEATURE:
```

```
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 305

Glx Gly Pro Pro Ile Ser Ile Asp Leu Pro Val Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 306
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 306

Glx Gly Pro Pro Ile Ser Ile Asp Leu Pro Ile Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 307
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 307

Glx Gly Pro Pro Ile Ser Ile Asp Leu Pro Phe Ala Leu Leu Arg Lys
1               5                   10                  15
```

Met Ile Glu Ile Glu Lys Gln Glu Lys Gln Gln Ala Ala Asn
            20                  25                  30

Asn Arg Leu Leu Leu Asp Thr Ile
            35                  40

<210> SEQ ID NO 308
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 308

Glx Gly Pro Pro Ile Ser Ile Asp Leu Pro Leu Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 309
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (12)..(12)
<223> OTHER INFORMATION: Ala=naphthylalanine
<220> FEATURE:
<221> NAME/KEY: MOD_RES
<222> LOCATION: (40)..(40)
<223> OTHER INFORMATION: AMIDATION

<400> SEQUENCE: 309

Glx Gly Pro Pro Ile Ser Ile Asp Leu Pro Tyr Ala Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

<210> SEQ ID NO 310
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID

```
<220> FEATURE:
<221> NAME/KEY: MOD_RES
<222> LOCATION: (40)..(40)
<223> OTHER INFORMATION: AMIDATION

<400> SEQUENCE: 310

Glx Gly Pro Pro Ile Ser Ile Asp Leu Pro Tyr Trp Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 311
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 311

Glx Gly Pro Pro Ile Ser Ile Asp Leu Pro Tyr Trp Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 312
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 312

Glx Gly Pro Pro Ile Ser Ile Asp Leu Pro Tyr His Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 313
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
```

```
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 313

Glx Gly Pro Pro Ile Ser Ile Asp Leu Pro Tyr His Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 314
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 314

Glx Gly Pro Pro Ile Ser Ile Asp Leu Pro Tyr His Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 315
<211> LENGTH: 39
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (39)..(39)
<223> OTHER INFORMATION: AMIDATION

<400> SEQUENCE: 315

Glx Gly Pro Pro Ile Ser Ile Asp Leu Pro Tyr His Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Ala Thr
        35

<210> SEQ ID NO 316
<211> LENGTH: 40
<212> TYPE: PRT
<213> ORGANISM: Artificial
<220> FEATURE:
<223> OTHER INFORMATION: Chemically synthesized artificial peptide
```

```
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 316

Glx Gly Pro Pro Ile Ser Ile Asp Leu Pro Phe Phe Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Asp Thr Ile
            35                  40

<210> SEQ ID NO 317
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 317

Glx Gly Pro Pro Ile Ser Ile Asp Leu Pro Phe Phe Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Ala Thr Ile
            35                  40

<210> SEQ ID NO 318
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 318

Glx Gly Pro Pro Ile Ser Ile Asp Leu Pro Phe Phe Leu Leu Arg Lys
1               5                   10                  15

Met Ile Glu Ile Glu Lys Gln Glu Lys Glu Lys Gln Gln Ala Ala Asn
            20                  25                  30

Asn Ala Leu Leu Leu Asp Thr Ile
            35                  40

<210> SEQ ID NO 319
<211> LENGTH: 40
<212> TYPE: PRT
<213> ORGANISM: Artificial
```

```
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 319

Glx Gly Pro Pro Ile Ser Ile Asp Leu Pro Phe Phe Leu Leu Arg Lys
 1               5                  10                  15

Met Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 320
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 320

Glx Gly Pro Pro Ile Ser Ile Asp Leu Pro Leu Gln Leu Leu Arg Lys
 1               5                  10                  15

Val Ile Glu Ile Glu Lys Gln Glu Lys Glu Lys Gln Gln Ala Thr Thr
            20                  25                  30

Asn Ala Arg Ile Leu Ala Arg Val
        35                  40

<210> SEQ ID NO 321
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 321

Glx Gly Pro Pro Ile Ser Ile Asp Leu Pro Phe Gln Leu Leu Arg Lys
 1               5                  10                  15

Thr Ile Glu Ile Glu Lys Gln Glu Lys Glu Lys Gln Gln Ala Thr Thr
            20                  25                  30

Asn Ala Arg Leu Leu Asp Arg Val
        35                  40

<210> SEQ ID NO 322
<211> LENGTH: 38
```

<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 322

Ile Val Leu Ser Leu Asp Val Pro Ile Gly Leu Leu Gln Lys Met Ile
1               5                   10                  15

Glu Ile Glu Lys Gln Glu Lys Glu Lys Gln Gln Ala Thr Thr Asn Ala
            20                  25                  30

Arg Ile Leu Ala Arg Val
        35

<210> SEQ ID NO 323
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 323

Asp Asn Pro Ser Leu Ser Ile Asp Leu Pro Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Glu Ile Phe Ala Glu Val
        35                  40

<210> SEQ ID NO 324
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 324

Asp Asn Pro Ser Leu Ser Ile Asp Leu Pro Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Gln Ile Phe Ala His Val
        35                  40

<210> SEQ ID NO 325
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 325

```
Ile Val Leu Ser Leu Asp Val Pro Ile Gly Leu Leu Gln Ile Leu Leu
1               5                   10                  15

Glu Gln Glu Lys Ala Arg Ala Ala Arg Glu Gln Ala Thr Thr Asn Ala
            20                  25                  30

Arg Ile Leu Ala Arg Val
            35
```

<210> SEQ ID NO 326
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 326

```
Asp Asn Pro Ser Leu Ser Ile Asp Leu Pro Leu Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Asn Ile Phe Ala Asn Val
            35                  40
```

<210> SEQ ID NO 327
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 327

```
Asp Asn Pro Ser Leu Ser Ile Asp Leu Pro Leu Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Gln Ile Phe Ala Gln Val
            35                  40
```

<210> SEQ ID NO 328
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 328

```
Asp Asn Pro Ser Leu Ser Ile Asp Leu Pro Leu Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala His Ile Phe Ala His Val
            35                  40
```

<210> SEQ ID NO 329
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 329

Asp Asn Pro Ser Leu Ser Ile Asp Leu Pro Leu Phe Leu Leu Arg Thr
1               5                   10                  15

Leu Leu Glu Leu Ala Arg Thr Gln Ser Gln Arg Glu Arg Ala Glu Gln
            20                  25                  30

Asn Ala Arg Ile Phe Ala Arg Val
        35                  40

<210> SEQ ID NO 330
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 330

Asp Asn Pro Ser Leu Ser Ile Asp Leu Pro Leu Ile Leu Leu Arg Thr
1               5                   10                  15

Leu Leu Glu Leu Ala Arg Thr Gln Ser Gln Arg Glu Arg Ala Glu Gln
            20                  25                  30

Asn Ala Arg Ile Phe Ala Arg Val
        35                  40

<210> SEQ ID NO 331
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 331

Pro Ser Leu Ser Ile Asp Leu Pro Leu Phe Leu Leu Arg Thr Leu Leu
1               5                   10                  15

Glu Leu Glu Lys Thr Gln Ser Gln Arg Glu Arg Ala Glu Gln Asn Ala
            20                  25                  30

Arg Ile Phe Ala Arg Val
        35

<210> SEQ ID NO 332
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)

<223> OTHER INFORMATION: AMIDATION

<400> SEQUENCE: 332

Pro Ser Leu Ser Ile Asp Leu Pro Leu Ile Leu Leu Arg Thr Leu Leu
1               5                   10                  15

Glu Leu Glu Lys Thr Gln Ser Gln Arg Glu Arg Ala Glu Gln Asn Ala
            20                  25                  30

Arg Ile Phe Ala Arg Val
        35

<210> SEQ ID NO 333
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 333

Pro Ser Leu Ser Ile Asp Leu Pro Leu Leu Leu Leu Arg Thr Leu Leu
1               5                   10                  15

Glu Leu Glu Lys Thr Gln Ser Gln Arg Glu Arg Ala Glu Gln Asn Ala
            20                  25                  30

Arg Ile Phe Ala Arg Val
        35

<210> SEQ ID NO 334
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 334

Asp Asn Pro Ser Leu Ser Ile Asp Leu Pro Leu Phe Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Ala Arg Val
        35                  40

<210> SEQ ID NO 335
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 335

Asp Asn Pro Ser Leu Ser Ile Asp Leu Pro Leu Ile Leu Leu Arg Thr
1               5                   10                  15

Leu Leu Glu Leu Glu Lys Thr Gln Ser Gln Arg Glu Arg Ala Glu Gln
            20                  25                  30

-continued

Asn Ala Arg Ile Phe Ala Arg Val
        35              40

<210> SEQ ID NO 336
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 336

Asp Asn Pro Ser Leu Ser Ile Asp Leu Pro Leu Phe Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Asp Arg Val
        35              40

<210> SEQ ID NO 337
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 337

Asp Asn Pro Ser Leu Ser Ile Asp Leu Pro Leu Ile Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Asp Arg Val
        35              40

<210> SEQ ID NO 338
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 338

Asp Asn Pro Ser Leu Ser Ile Asp Leu Pro Leu Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Asp Arg Val
        35              40

<210> SEQ ID NO 339
<211> LENGTH: 40
<212> TYPE: PRT
<213> ORGANISM: Artificial
<220> FEATURE:
<223> OTHER INFORMATION: Chemically synthesized artificial peptide

```
<220> FEATURE:
<221> NAME/KEY: MOD_RES
<222> LOCATION: (40)..(40)
<223> OTHER INFORMATION: AMIDATION

<400> SEQUENCE: 339

Asp Asn Pro Ser Leu Ser Ile Asp Leu Pro Gln Tyr Leu Leu Arg Thr
1               5                   10                  15

Leu Leu Glu Leu Ala Arg Thr Gln Ser Gln Arg Glu Arg Ala Glu Gln
            20                  25                  30

Asn Ala Ile Ile Phe Ala Ser Val
        35                  40

<210> SEQ ID NO 340
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 340

Asp Asn Pro Ser Leu Ser Ile Asp Leu Pro Leu Leu Leu Leu Arg Thr
1               5                   10                  15

Leu Leu Glu Leu Ala Arg Thr Gln Ser Gln Arg Glu Arg Ala Glu Gln
            20                  25                  30

Asn Ala Arg Ile Phe Ala Arg Val
        35                  40

<210> SEQ ID NO 341
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 341

Asp Asn Pro Ser Leu Ser Ile Asp Leu Pro Leu Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Ala Arg Val
        35                  40

<210> SEQ ID NO 342
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 342

Asp Asn Pro Ser Leu Ser Ile Asp Leu Pro Leu Gln Leu Leu Arg Thr
1               5                   10                  15
```

Leu Leu Glu Leu Glu Lys Thr Gln Ser Gln Arg Glu Arg Ala Glu Gln
            20                  25                  30

Asn Ala Ile Ile Phe Ala Ser Val
            35                  40

<210> SEQ ID NO 343
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 343

Asp Asn Pro Ser Leu Ser Ile Asp Leu Pro Leu Phe Leu Leu Arg Thr
1               5                   10                  15

Leu Leu Glu Leu Glu Lys Thr Gln Ser Gln Arg Glu Arg Ala Glu Gln
            20                  25                  30

Asn Ala Ile Ile Phe Ala Ser Val
            35                  40

<210> SEQ ID NO 344
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 344

Pro Ser Leu Ser Ile Asp Leu Pro Leu Leu Leu Arg Thr Leu Leu
1               5                   10                  15

Glu Leu Glu Lys Thr Gln Ser Gln Arg Glu Arg Ala Glu Gln Asn Ala
            20                  25                  30

Ile Ile Phe Ala Ser Val
            35

<210> SEQ ID NO 345
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 345

Asp Asn Pro Ser Leu Ser Ile Asp Leu Pro Leu Ile Leu Leu Arg Thr
1               5                   10                  15

Leu Leu Glu Leu Glu Lys Thr Gln Ser Gln Arg Glu Arg Ala Glu Gln
            20                  25                  30

Asn Ala Ile Ile Phe Ala Ser Val
            35                  40

<210> SEQ ID NO 346
<211> LENGTH: 40
<212> TYPE: PRT

<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 346

Asp Asn Pro Ser Leu Ser Ile Asp Leu Pro Leu Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Ile Ile Phe Ala Ser Val
            35                  40

<210> SEQ ID NO 347
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (40)..(40)
<223> OTHER INFORMATION: AMIDATION

<400> SEQUENCE: 347

Asp Asn Pro Ser Leu Ser Ile Asp Leu Pro Leu Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Ile Ile Phe Ala Ser Val
            35                  40

<210> SEQ ID NO 348
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (38)..(38)
<223> OTHER INFORMATION: AMIDATION

<400> SEQUENCE: 348

Pro Ser Leu Ser Ile Asp Leu Pro Leu Leu Leu Leu Arg Thr Leu Leu
1               5                   10                  15

Glu Leu Glu Lys Thr Gln Ser Gln Arg Glu Arg Ala Glu Gln Asn Ala
            20                  25                  30

Ile Ile Phe Ala Ser Val
            35

<210> SEQ ID NO 349
<211> LENGTH: 40
<212> TYPE: PRT
<213> ORGANISM: Artificial
<220> FEATURE:

```
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 349

Glx Gly Pro Pro Ile Ser Ile Asp Leu Pro Leu Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 350
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 350

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 351
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 351

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Thr Thr
            20                  25                  30

Asn Ala Arg Leu Leu Asp Arg Val
        35                  40

<210> SEQ ID NO 352
<211> LENGTH: 40
<212> TYPE: PRT
```

```
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 352

Glx Gly Pro Pro Ile Ser Ile Asp Leu Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Leu Leu Leu Ala Thr Ile
            35                  40

<210> SEQ ID NO 353
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 353

Glx Gly Pro Pro Ile Ser Ile Asp Leu Pro Leu Tyr Leu Leu Arg Lys
1               5                   10                  15

Met Ile Glu Ile Glu Lys Gln Glu Lys Glu Lys Gln Gln Ala Thr Thr
            20                  25                  30

Asn Ala Arg Ile Leu Ala Arg Val
            35                  40

<210> SEQ ID NO 354
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (38)..(38)
<223> OTHER INFORMATION: AMIDATION

<400> SEQUENCE: 354

Ile Val Leu Ser Leu Asp Val Pro Ile Gly Leu Leu Gln Ile Leu Leu
1               5                   10                  15

Glu Gln Ala Arg Ala Arg Ala Arg Glu Gln Ala Thr Thr Asn Ala
            20                  25                  30

Arg Ile Leu Ala Arg Val
            35

<210> SEQ ID NO 355
```

```
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 355

Glx Gly Pro Pro Ile Ser Ile Asp Leu Ser Leu Glu Leu Leu Arg Lys
 1               5                  10                  15

Met Ile Glu Ile Glu Lys Gln Glu Lys Glu Lys Gln Gln Ala Ala Asn
             20                  25                  30

Asn Arg Leu Leu Leu Asp Thr Ile
         35                  40

<210> SEQ ID NO 356
<211> LENGTH: 39
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (39)..(39)
<223> OTHER INFORMATION: AMIDATION

<400> SEQUENCE: 356

Ile Val Leu Ser Leu Asp Val Pro Ile Gly Leu Leu Gln Ile Leu Leu
 1               5                  10                  15

Glu Gln Ala Arg Ala Arg Ala Ala Arg Glu Gln Ala Thr Thr Asn Ala
             20                  25                  30

Arg Ile Leu Ala Arg Val Met
         35

<210> SEQ ID NO 357
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 357

Glx Gly Pro Pro Ile Ser Ile Asp Leu Pro Phe Gln Leu Leu Arg Lys
 1               5                  10                  15

Leu Ile Glu Ile Glu Lys Gln Glu Lys Glu Lys Gln Gln Ala Ala Asn
             20                  25                  30

Asn Ala Leu Leu Leu Ala Thr Ile
         35                  40

<210> SEQ ID NO 358
<211> LENGTH: 39
<212> TYPE: PRT
```

```
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (39)..(39)
<223> OTHER INFORMATION: AMIDATION

<400> SEQUENCE: 358

Glx Gly Pro Pro Ile Ser Ile Asp Leu Pro Phe Gln Leu Leu Arg Ile
 1               5                  10                  15

Leu Ile Glu Ile Glu Lys Gln Glu Lys Glu Lys Gln Gln Ala Ala Asn
                20                  25                  30

Asn Ala Leu Leu Leu Ala Thr
            35

<210> SEQ ID NO 359
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 359

Glx Gly Pro Pro Ile Ser Ile Asp Leu Pro Phe Gln Leu Leu Arg Glu
 1               5                  10                  15

Val Ile Glu Ile Glu Lys Gln Glu Lys Glu Lys Gln Gln Ala Ala Asn
                20                  25                  30

Asn Ala Leu Leu Leu Ala Thr Ile
            35                  40

<210> SEQ ID NO 360
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 360

Glx Gly Pro Pro Ile Ser Ile Asp Leu Pro Phe Gln Leu Leu Arg Leu
 1               5                  10                  15

Leu Ile Glu Ile Glu Lys Gln Glu Lys Glu Lys Gln Gln Ala Ala Asn
                20                  25                  30

Asn Ala Leu Leu Leu Ala Thr Ile
            35                  40

<210> SEQ ID NO 361
```

<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 361

Glx Gly Pro Pro Ile Ser Ile Asp Leu Pro Phe Gln Leu Leu Arg Val
1               5                   10                  15

Leu Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 362
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 362

Glx Gly Pro Pro Ile Ser Ile Asp Leu Pro Phe Gln Leu Leu Arg Lys
1               5                   10                  15

Ile Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 363
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 363

Glx Gly Pro Pro Ile Ser Ile Asp Leu Pro Phe Gln Leu Leu Arg Lys
1               5                   10                  15

Ala Ile Glu Ile Glu Lys Gln Glu Lys Glu Lys Gln Gln Ala Thr Thr
            20                  25                  30

Asn Ala Arg Leu Leu Asp Arg Val
        35                  40

```
<210> SEQ ID NO 364
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 364

Glx Gly Pro Pro Ile Ser Ile Asp Leu Pro Phe Gln Leu Leu Arg Lys
1               5                   10                  15

Ala Ile Glu Ile Glu Lys Gln Glu Lys Glu Lys Gln Gln Ala Ala Asn
            20                  25                  30

Asn Ala Leu Leu Leu Ala Thr Ile
        35                  40

<210> SEQ ID NO 365
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 365

Glx Gly Pro Pro Ile Ser Ile Asp Leu Pro Phe Gln Leu Leu Arg Lys
1               5                   10                  15

Ala Ile Glu Ile Glu Lys Gln Glu Lys Glu Lys Gln Gln Ala Ala Asn
            20                  25                  30

Asn Ala Leu Leu Leu Asp Thr Ile
        35                  40

<210> SEQ ID NO 366
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 366

Ile Val Leu Ser Leu Asp Val Pro Ile Gly Leu Leu Gln Ile Leu Leu
1               5                   10                  15

Glu Lys Ala Ala Ala Glu Ala Glu Ala Ala Lys Ala Ala Gln Glu
            20                  25                  30

Gln Ile Leu Ala His Val
        35

<210> SEQ ID NO 367
```

```
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 367

Ile Val Leu Ser Leu Asp Val Pro Ile Gly Leu Leu Gln Ile Leu Leu
1               5                   10                  15

Glu Gln Ala Arg His Ala Ala Ala His Ala Ala Ala His Ala Gln Ala
            20                  25                  30

His Ile Leu Ala His Val
            35

<210> SEQ ID NO 368
<211> LENGTH: 39
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (39)..(39)
<223> OTHER INFORMATION: AMIDATION

<400> SEQUENCE: 368

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val Met
            35

<210> SEQ ID NO 369
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 369

Ile Val Leu Ser Leu Asp Val Pro Ile Gly Leu Leu Gln Ile Leu Leu
1               5                   10                  15

Glu Gln Ala Arg His Ala His Ala His Ala His Ala His Ala Gln Ala
            20                  25                  30

His Ile Leu Ala His Val
            35

<210> SEQ ID NO 370
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION
```

-continued

```
<400> SEQUENCE: 370

Ile Val Leu Ser Leu Asp Val Ser Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 371
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 371

Ile Val Leu Ser Leu Asp Val Pro Ile His Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 372
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 372

Glx Gly Pro Pro Ile Ser Ile Asp Val Pro Tyr Trp Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Asp Thr Ile
        35                  40

<210> SEQ ID NO 373
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 373
```

```
Glx Gly Pro Pro Ile Ser Ile Asp Val Pro Tyr Trp Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
            35                  40

<210> SEQ ID NO 374
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 374

Glx Gly Pro Pro Ile Ser Ile Asp Val Pro Tyr Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Asp Thr Ile
            35                  40

<210> SEQ ID NO 375
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 375

Glx Gly Pro Pro Ile Ser Ile Asp Val Pro Tyr Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
            35                  40

<210> SEQ ID NO 376
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION
```

```
<400> SEQUENCE: 376

Glx Gly Pro Pro Ile Ser Ile Asp Val Pro Tyr His Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Asp Thr Ile
            35                  40

<210> SEQ ID NO 377
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 377

Glx Gly Pro Pro Ile Ser Ile Asp Val Pro Tyr His Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
            35                  40

<210> SEQ ID NO 378
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 378

Glx Gly Pro Pro Ile Ser Ile Asp Val Pro Tyr Tyr Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
            35                  40

<210> SEQ ID NO 379
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
```

<223> OTHER INFORMATION: AMIDATION

<400> SEQUENCE: 379

Glx Gly Pro Pro Ile Ser Ile Asp Val Pro Ile Tyr Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 380
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 380

Glx Gly Pro Pro Ile Ser Ile Asp Val Pro Leu Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Asp Thr Ile
        35                  40

<210> SEQ ID NO 381
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 381

Glx Gly Pro Pro Ile Ser Ile Asp Val Pro Leu Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
        35                  40

<210> SEQ ID NO 382
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:

```
<221> NAME/KEY: MOD_RES
<222> LOCATION: (40)..(40)
<223> OTHER INFORMATION: AMIDATION

<400> SEQUENCE: 382

Glx Gly Pro Pro Ile Ser Ile Asp Val Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Asp Thr Ile
            35                  40

<210> SEQ ID NO 383
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 383

Glx Gly Pro Pro Ile Ser Ile Asp Val Pro Phe Gln Leu Leu Arg Lys
1               5                   10                  15

Val Ile Glu Ile Glu Lys Gln Glu Lys Glu Lys Gln Gln Ala Ala Asn
            20                  25                  30

Asn Ala Arg Leu Leu Ala Arg Ile
            35                  40

<210> SEQ ID NO 384
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 384

Asp Asn Pro Ser Leu Ser Ile Asp Val Pro Leu Leu Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Ala Arg Val
            35                  40

<210> SEQ ID NO 385
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 385
```

Asp Asn Pro Ser Leu Ser Ile Asp Val Pro Leu Phe Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Ala Arg Val
            35                  40

<210> SEQ ID NO 386
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 386

Asp Asn Pro Ser Leu Ser Ile Asp Val Pro Phe Phe Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Ala Arg Val
            35                  40

<210> SEQ ID NO 387
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 387

Asp Asn Pro Ser Leu Ser Ile Asp Val Pro Leu Tyr Leu Leu Arg Thr
1               5                   10                  15

Leu Leu Glu Leu Glu Lys Thr Gln Ser Gln Arg Glu Arg Ala Glu Gln
            20                  25                  30

Asn Ala Arg Ile Phe Ala Arg Val
            35                  40

<210> SEQ ID NO 388
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 388

Glu Asp Leu Pro Leu
1               5

<210> SEQ ID NO 389
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 389

Asp Asn Pro Ser Leu

<210> SEQ ID NO 390
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 390

Asp Asp Pro Pro Leu
1               5

<210> SEQ ID NO 391
<211> LENGTH: 5
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 391

Glx Gly Pro Pro Ile
1               5

<210> SEQ ID NO 392
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 392

Ser Gln Glu Pro Pro Ile
1               5

<210> SEQ ID NO 393
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 393

Ser Glu Glu Pro Pro Ile
1               5

<210> SEQ ID NO 394
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 394

Thr Lys Phe Thr Leu
1               5

<210> SEQ ID NO 395
<211> LENGTH: 6
<212> TYPE: PRT
<213> ORGANISM: artificial
<220> FEATURE:
<223> OTHER INFORMATION: Chemically synthesized artificial peptide

```
<400> SEQUENCE: 395

Ser Gln Glu Ile Val Leu
1               5

<210> SEQ ID NO 396
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 396

Ser Glu Glu Ile Val Leu
1               5

<210> SEQ ID NO 397
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 397

Asp Asn Pro Ile Val Leu
1               5

<210> SEQ ID NO 398
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 398

Thr Lys Ile Val Leu
1               5

<210> SEQ ID NO 399
<211> LENGTH: 5
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 399

Glx Gly Ile Val Leu
1               5

<210> SEQ ID NO 400
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 400

His His His His His His
1               5

<210> SEQ ID NO 401
<211> LENGTH: 6
<212> TYPE: PRT
<213> ORGANISM: artificial
```

```
<220> FEATURE:
<223> OTHER INFORMATION: Chemically synthesized artificial peptide

<400> SEQUENCE: 401

Ser Asp Asn Pro Ser Leu
1               5

<210> SEQ ID NO 402
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 402

Ser Thr Lys Phe Thr Leu
1               5

<210> SEQ ID NO 403
<211> LENGTH: 6
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (2)..(2)
<223> OTHER INFORMATION: PYRROLIDONE CARBOXYLIC ACID

<400> SEQUENCE: 403

Ser Glx Gly Pro Pro Ile
1               5

<210> SEQ ID NO 404
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 404

Asn Asp Asp Pro Pro Ile
1               5

<210> SEQ ID NO 405
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 405

Ser Ile Asp Leu
1

<210> SEQ ID NO 406
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 406

Ser Leu Asp Val
1

<210> SEQ ID NO 407
```

```
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 407

Ser Leu Asp Leu
1

<210> SEQ ID NO 408
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 408

Ser Ile Asp Ile
1

<210> SEQ ID NO 409
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 409

Ser Ile Asp Val
1

<210> SEQ ID NO 410
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 410

Val Leu Ile Asp Leu
1               5

<210> SEQ ID NO 411
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 411

Val Leu Phe Asp Val
1               5

<210> SEQ ID NO 412
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 412

Val Leu Ile Glu Ile
1               5

<210> SEQ ID NO 413
<211> LENGTH: 5
```

```
<212> TYPE: PRT
<213> ORGANISM: artificial
<220> FEATURE:
<223> OTHER INFORMATION: Chemically synthesized artificial peptide

<400> SEQUENCE: 413

Ile Leu Phe Asn Ile
1               5

<210> SEQ ID NO 414
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 414

Leu Leu Ile Glu Ile
1               5

<210> SEQ ID NO 415
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 415

Leu Leu Phe Asn Ile
1               5

<210> SEQ ID NO 416
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 416

Ile Leu Leu Glu Gln
1               5

<210> SEQ ID NO 417
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 417

Ile Leu Ile Glu Ile
1               5

<210> SEQ ID NO 418
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 418

Ile Leu Leu Glu Ile
1               5

<210> SEQ ID NO 419
<211> LENGTH: 5
<212> TYPE: PRT
```

```
<213> ORGANISM: artificial
<220> FEATURE:
<223> OTHER INFORMATION: Chemically synthesized artificial peptide

<400> SEQUENCE: 419

Thr Leu Leu Glu Leu
1               5

<210> SEQ ID NO 420
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 420

Lys Met Ile Glu Ile
1               5

<210> SEQ ID NO 421
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 421

Lys Val Ile Glu Ile
1               5

<210> SEQ ID NO 422
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 422

Glu Val Leu Glu Met
1               5

<210> SEQ ID NO 423
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 423

Glu Met Ile Glu Ile
1               5

<210> SEQ ID NO 424
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 424

Glu Val Ile Glu Ile
1               5

<210> SEQ ID NO 425
<211> LENGTH: 5
<212> TYPE: PRT
<213> ORGANISM: artificial
```

```
<220> FEATURE:
<223> OTHER INFORMATION: Chemically synthesized artificial peptide

<400> SEQUENCE: 425

Glu Ala Ile Glu Ile
1               5

<210> SEQ ID NO 426
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 426

Glu Thr Ile Glu Ile
1               5

<210> SEQ ID NO 427
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 427

Glu Ile Ile Glu Ile
1               5

<210> SEQ ID NO 428
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 428

Glu Leu Ile Glu Ile
1               5

<210> SEQ ID NO 429
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 429

Asn Met Ile Glu Met
1               5

<210> SEQ ID NO 430
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 430

Asn Met Ile His Arg
1               5

<210> SEQ ID NO 431
<211> LENGTH: 5
<212> TYPE: PRT
<213> ORGANISM: artificial
<220> FEATURE:
```

```
-continued

<223> OTHER INFORMATION: Chemically synthesized artificial peptide

<400> SEQUENCE: 431

Asn Met Ile His Met
1               5

<210> SEQ ID NO 432
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 432

Gln Met Met Glu Met
1               5

<210> SEQ ID NO 433
<211> LENGTH: 5
<212> TYPE: PRT
<213> ORGANISM: artificial
<220> FEATURE:
<223> OTHER INFORMATION: Chemically synthesized artificial peptide

<400> SEQUENCE: 433

Leu Leu Phe Asn Ile
1               5

<210> SEQ ID NO 434
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 434

Ser Arg Ala Glu
1

<210> SEQ ID NO 435
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 435

Glu Lys Ala Arg
1

<210> SEQ ID NO 436
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 436

Glu Arg Ala Arg
1

<210> SEQ ID NO 437
<211> LENGTH: 4
<212> TYPE: PRT
<213> ORGANISM: artificial
<220> FEATURE:
<223> OTHER INFORMATION: Chemically synthesized artificial peptide
```

<400> SEQUENCE: 437

Glu Lys Gln Glu
1

<210> SEQ ID NO 438
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 438

Thr Lys Asp Arg
1

<210> SEQ ID NO 439
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 439

Thr Lys Ala Asp
1

<210> SEQ ID NO 440
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 440

Ala Lys Ala Arg
1

<210> SEQ ID NO 441
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 441

Ala Lys Gln Arg
1

<210> SEQ ID NO 442
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 442

Glu Arg Gln Arg
1

<210> SEQ ID NO 443
<211> LENGTH: 4
<212> TYPE: PRT
<213> ORGANISM: artificial
<220> FEATURE:
<223> OTHER INFORMATION: Chemically synthesized artificial peptide

```
<400> SEQUENCE: 443

Ala Lys Ala Glu
1

<210> SEQ ID NO 444
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 444

Glu Arg Ala Glu
1

<210> SEQ ID NO 445
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 445

Ala Arg Gln Arg
1

<210> SEQ ID NO 446
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 446

Glu Lys Gln Arg
1

<210> SEQ ID NO 447
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 447

Thr Lys Ala Asn
1

<210> SEQ ID NO 448
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 448

Thr Lys Ala Arg
1

<210> SEQ ID NO 449
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 449
```

```
Glu Ala Ala Arg
1

<210> SEQ ID NO 450
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 450

Glu Arg Gln Glu
1

<210> SEQ ID NO 451
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 451

Ala Arg Ala Asp
1

<210> SEQ ID NO 452
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 452

Glu Lys Thr Gln
1

<210> SEQ ID NO 453
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 453

Ala Arg Ala Arg
1

<210> SEQ ID NO 454
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 454

Ala Arg Ala Glu
1

<210> SEQ ID NO 455
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 455
```

Ala Arg Gln Glu
1

<210> SEQ ID NO 456
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 456

Ala Lys Gln Glu
1

<210> SEQ ID NO 457
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 457

Thr Arg Ala Asp
1

<210> SEQ ID NO 458
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 458

Ala Lys Ala Asp
1

<210> SEQ ID NO 459
<211> LENGTH: 4
<212> TYPE: PRT
<213> ORGANISM: artificial
<220> FEATURE:
<223> OTHER INFORMATION: Chemically synthesized artificial peptide

<400> SEQUENCE: 459

Thr Arg Ala Arg
1

<210> SEQ ID NO 460
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 460

Ala Ala Arg Glu Gln Ala
1               5

<210> SEQ ID NO 461
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 461

Lys Glu Lys Lys Arg Lys

<210> SEQ ID NO 462
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 462

Ser Gln Arg Glu Arg Ala
1               5

<210> SEQ ID NO 463
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 463

Lys Glu Lys Gln Gln Ala
1               5

<210> SEQ ID NO 464
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 464

Gln Leu Ala Gln Gln Ala
1               5

<210> SEQ ID NO 465
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 465

Ala Ala Asn Arg Leu Leu Leu Asp Thr Val
1               5                   10

<210> SEQ ID NO 466
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 466

Ala Ala Gln Glu Gln Ile Leu Ala His Val
1               5                   10

<210> SEQ ID NO 467
<211> LENGTH: 10
<212> TYPE: PRT

```
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 467

Ala Asn Asn Ala Glu Leu Leu Ala Glu Ile
1               5                   10

<210> SEQ ID NO 468
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 468

Ala Asn Asn Ala His Leu Leu Ala His Ile
1               5                   10

<210> SEQ ID NO 469
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 469

Ala Asn Asn Ala Lys Leu Leu Ala Lys Ile
1               5                   10

<210> SEQ ID NO 470
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 470

Ala Asn Asn Ala Leu Leu Leu Ala Thr Ile
1               5                   10

<210> SEQ ID NO 471
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 471

Ala Asn Asn Ala Leu Leu Leu Asp Thr Ile
```

<210> SEQ ID NO 472
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 472

Ala Asn Asn Ala Asn Leu Leu Ala Asn Ile
1               5                   10

<210> SEQ ID NO 473
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 473

Ala Asn Asn Ala Gln Leu Leu Ala His Ile
1               5                   10

<210> SEQ ID NO 474
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 474

Ala Asn Asn Ala Gln Leu Leu Ala Gln Ile
1               5                   10

<210> SEQ ID NO 475
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 475

Ala Asn Asn Ala Arg Ile Leu Ala Arg Val
1               5                   10

<210> SEQ ID NO 476
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES

```
<222> LOCATION: (10)..(10)
<223> OTHER INFORMATION: AMIDATION

<400> SEQUENCE: 476

Ala Asn Asn Ala Arg Leu Leu Ala Arg Ile
1               5                   10

<210> SEQ ID NO 477
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 477

Ala Asn Asn Ala Arg Leu Leu Asp Thr Ile
1               5                   10

<210> SEQ ID NO 478
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 478

Ala Asn Asn Arg Leu Leu Leu Ala Thr Ile
1               5                   10

<210> SEQ ID NO 479
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 479

Ala Asn Asn Arg Leu Leu Leu Asp Thr Ile
1               5                   10

<210> SEQ ID NO 480
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 480

Glu Gln Asn Ala His Ile Phe Ala His Val
1               5                   10

<210> SEQ ID NO 481
<211> LENGTH: 10
```

```
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 481

Glu Gln Asn Ala Gln Ile Phe Ala His Val
1               5                   10

<210> SEQ ID NO 482
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 482

Glu Gln Asn Ala Arg Ile Phe Ala Arg Val
1               5                   10

<210> SEQ ID NO 483
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 483

Glu Gln Asn Arg Ile Ile Phe Asp Ser Val
1               5                   10

<210> SEQ ID NO 484
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 484

Glu Thr Asn Ala Arg Ile Leu Ala Arg Val
1               5                   10

<210> SEQ ID NO 485
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 485
```

-continued

```
His Ala Gln Ala His Ile Leu Ala His Val
1               5                   10

<210> SEQ ID NO 486
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 486

His Ser Asn Arg Lys Ile Ile Asp Ile Ala
1               5                   10

<210> SEQ ID NO 487
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 487

His Ser Asn Arg Lys Leu Leu Asp Ile Ala
1               5                   10

<210> SEQ ID NO 488
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 488

His Ser Asn Arg Lys Leu Met Glu Ile Ile
1               5                   10

<210> SEQ ID NO 489
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 489

His Thr Asn Ala Arg Ile Leu Ala Arg Val
1               5                   10

<210> SEQ ID NO 490
<211> LENGTH: 10
<212> TYPE: PRT
<213> ORGANISM: artificial
<220> FEATURE:
<223> OTHER INFORMATION: Chemically synthesized artificial peptide
<220> FEATURE:
```

```
<221> NAME/KEY: MOD_RES
<222> LOCATION: (10)..(10)
<223> OTHER INFORMATION: AMIDATION

<400> SEQUENCE: 490

Thr Asn Asn Arg Leu Leu Leu Ala Thr Val
1               5                   10

<210> SEQ ID NO 491
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 491

Thr Asn Asn Arg Leu Leu Leu Asp Thr Ile
1               5                   10

<210> SEQ ID NO 492
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 492

Thr Ser Asn Arg Lys Leu Met Glu Ile Ile
1               5                   10

<210> SEQ ID NO 493
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 493

Thr Thr Asn Ala Arg Ile Leu Ala Arg Asn
1               5                   10

<210> SEQ ID NO 494
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 494

Thr Thr Asn Ala Arg Ile Leu Ala Arg Val
1               5                   10

<210> SEQ ID NO 495
```

```
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 495

Thr Thr Asn Ala Arg Leu Leu Ala Thr Val
1               5                   10

<210> SEQ ID NO 496
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 496

Thr Thr Asn Ala Arg Leu Leu Asp Arg Val
1               5                   10

<210> SEQ ID NO 497
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 497

Thr Thr Asn Ala Arg Leu Leu Asp Thr Val
1               5                   10

<210> SEQ ID NO 498
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 498

Thr Thr Asn Arg Leu Leu Leu Ala Arg Val
1               5                   10

<210> SEQ ID NO 499
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 499
```

Thr Thr Asn Arg Leu Leu Leu Ala Thr Val
1               5                   10

<210> SEQ ID NO 500
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 500

Thr Thr Asn Arg Leu Leu Leu Asp Thr Val
1               5                   10

<210> SEQ ID NO 501
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 501

Thr Thr Gln Ala Arg Ile Leu Ala Arg Val
1               5                   10

<210> SEQ ID NO 502
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (10)..(10)
<223> OTHER INFORMATION: AMIDATION

<400> SEQUENCE: 502

Thr Thr Val Ala Arg Ile Leu Ala Arg Val
1               5                   10

<210> SEQ ID NO 503
<211> LENGTH: 10
<212> TYPE: PRT
<213> ORGANISM: artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 503

Glx Gly Pro Pro Ile Ser Ile Asp Leu Pro
1               5                   10

<210> SEQ ID NO 504
<211> LENGTH: 4
<212> TYPE: PRT
<213> ORGANISM: artificial
<220> FEATURE:
<223> OTHER INFORMATION: Chemically synthesized artificial peptide

```
<400> SEQUENCE: 504

Leu Leu Arg Lys
1

<210> SEQ ID NO 505
<211> LENGTH: 13
<212> TYPE: PRT
<213> ORGANISM: artificial
<220> FEATURE:
<223> OTHER INFORMATION: Chemically synthesized artificial peptide

<400> SEQUENCE: 505

Ile Glu Ile Glu Lys Gln Glu Lys Glu Lys Gln Gln Ala
1               5                   10

<210> SEQ ID NO 506
<211> LENGTH: 6
<212> TYPE: PRT
<213> ORGANISM: artificial
<220> FEATURE:
<223> OTHER INFORMATION: Chemically synthesized artificial peptide

<400> SEQUENCE: 506

Pro Ser Leu Ser Ile Asp
1               5

<210> SEQ ID NO 507
<211> LENGTH: 22
<212> TYPE: PRT
<213> ORGANISM: artificial
<220> FEATURE:
<223> OTHER INFORMATION: Chemically synthesized artificial peptide

<400> SEQUENCE: 507

Leu Leu Arg Thr Leu Leu Glu Leu Glu Lys Thr Gln Ser Gln Arg Glu
1               5                   10                  15

Arg Ala Glu Gln Asn Ala
            20

<210> SEQ ID NO 508
<211> LENGTH: 37
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (37)..(37)
<223> OTHER INFORMATION: AMIDATION

<400> SEQUENCE: 508

Val Leu Ser Leu Asp Val Pro Ile Gly Leu Leu Gln Ile Leu Leu Glu
1               5                   10                  15

Ile Glu Lys Gln Glu Ala Ala Arg Asn Gln Ala Thr Thr Asn Ala Arg
            20                  25                  30

Ile Leu Ala Arg Val
            35

<210> SEQ ID NO 509
<211> LENGTH: 38
<212> TYPE: PRT
<213> ORGANISM: Artificial
<220> FEATURE:
<223> OTHER INFORMATION: Chemically synthesized artificial peptide
<220> FEATURE:
```

<221> NAME/KEY: MOD_RES
<222> LOCATION: (38)..(38)
<223> OTHER INFORMATION: AMIDATION

<400> SEQUENCE: 509

Ile Val Leu Ser Leu Asp Val Pro Ile Gly Leu Leu Gln Ile Leu Leu
1               5                   10                  15

Glu Ile Glu Lys Gln Glu Lys Ala Arg Asn Gln Ala Thr Thr Asn Ala
            20                  25                  30

Arg Ile Leu Ala Arg Val
        35

<210> SEQ ID NO 510
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 510

Ile Val Leu Ser Leu Asp Val Pro Ile Gly Leu Leu Gln Ile Leu Leu
1               5                   10                  15

Glu Ile Glu Lys Gln Glu Lys Glu Arg Asn Gln Ala Thr Thr Asn Ala
            20                  25                  30

Arg Ile Leu Ala Arg Val
        35

<210> SEQ ID NO 511
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 511

Ile Val Leu Ser Leu Asp Val Pro Ile Gly Leu Leu Gln Ile Leu Leu
1               5                   10                  15

Glu Ile Glu Lys Gln Glu Lys Glu Lys Asn Gln Ala Thr Thr Asn Ala
            20                  25                  30

Arg Ile Leu Ala Arg Val
        35

<210> SEQ ID NO 512
<211> LENGTH: 38
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (38)..(38)
<223> OTHER INFORMATION: AMIDATION

<400> SEQUENCE: 512

Ile Val Leu Ser Leu Asp Val Pro Ile Gly Leu Leu Gln Ile Leu Leu
1               5                   10                  15

Glu Ile Glu Lys Gln Glu Lys Glu Lys Gln Gln Ala Thr Thr Asn Ala

```
                      20                  25                  30

Arg Ile Leu Ala Arg Val
            35

<210> SEQ ID NO 513
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (40)..(40)
<223> OTHER INFORMATION: AMIDATION

<400> SEQUENCE: 513

Glx Gly Pro Pro Ile Ser Ile Asp Leu Ser Leu Glu Leu Leu Arg Ile
1               5                  10                  15

Leu Leu Glu Gln Ala Arg Ala Arg Ala Ala Arg Asn Gln Ala Ala Asn
            20                  25                  30

Asn Arg Leu Leu Leu Asp Thr Ile
            35                  40

<210> SEQ ID NO 514
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 514

Asp Asn Pro Ser Leu Ser Ile Asp Val Pro Leu Leu Leu Leu Arg Thr
1               5                  10                  15

Leu Leu Glu Leu Glu Lys Gln Gln Ser Gln Arg Glu Arg Ala Glu Gln
            20                  25                  30

Asn Ala Arg Ile Phe Ala Arg Val
            35                  40

<210> SEQ ID NO 515
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 515

Asp Asn Pro Ser Leu Ser Ile Asp Val Pro Leu Leu Leu Leu Arg Thr
1               5                  10                  15

Leu Leu Glu Leu Glu Lys Gln Glu Ser Gln Arg Glu Arg Ala Glu Gln
            20                  25                  30

Asn Ala Arg Ile Phe Ala Arg Val
            35                  40
```

<210> SEQ ID NO 516
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 516

Asp Asn Pro Ser Leu Ser Ile Asp Val Pro Leu Leu Leu Leu Arg Thr
1               5                   10                  15

Leu Leu Glu Leu Glu Lys Gln Glu Lys Gln Arg Glu Arg Ala Glu Gln
            20                  25                  30

Asn Ala Arg Ile Phe Ala Arg Val
        35                  40

<210> SEQ ID NO 517
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 517

Asp Asn Pro Ser Leu Ser Ile Asp Val Pro Leu Leu Leu Leu Arg Thr
1               5                   10                  15

Leu Leu Glu Leu Glu Lys Gln Glu Lys Glu Arg Glu Arg Ala Glu Gln
            20                  25                  30

Asn Ala Arg Ile Phe Ala Arg Val
        35                  40

<210> SEQ ID NO 518
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 518

Asp Asn Pro Ser Leu Ser Ile Asp Val Pro Leu Leu Leu Leu Arg Thr
1               5                   10                  15

Leu Leu Glu Leu Glu Lys Gln Glu Lys Glu Lys Glu Arg Ala Glu Gln
            20                  25                  30

Asn Ala Arg Ile Phe Ala Arg Val
        35                  40

<210> SEQ ID NO 519
<211> LENGTH: 40
<212> TYPE: PRT
<213> ORGANISM: Artificial
<220> FEATURE:
<223> OTHER INFORMATION: Chemically synthesized artificial peptide
<220> FEATURE:
<221> NAME/KEY: MOD_RES
<222> LOCATION: (40)..(40)
<223> OTHER INFORMATION: AMIDATION

<400> SEQUENCE: 519

Asp Asn Pro Ser Leu Ser Ile Asp Val Pro Leu Leu Leu Arg Thr
1               5                   10                  15
Leu Leu Glu Leu Glu Lys Gln Glu Lys Glu Lys Gln Arg Ala Glu Gln
            20                  25                  30
Asn Ala Arg Ile Phe Ala Arg Val
        35                  40

<210> SEQ ID NO 520
<211> LENGTH: 4
<212> TYPE: PRT
<213> ORGANISM: Artificial
<220> FEATURE:
<223> OTHER INFORMATION: Chemically synthesized artificial peptide

<400> SEQUENCE: 520

Glu Lys Gln Gln
1

<210> SEQ ID NO 521
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 521

Ala Ala Arg Asn Gln Ala
1               5

<210> SEQ ID NO 522
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 522

Lys Glu Arg Asn Gln Ala
1               5

<210> SEQ ID NO 523
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 523

Lys Glu Lys Asn Gln Ala
1               5

<210> SEQ ID NO 524
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 524

Lys Gln Arg Glu Arg Ala
1               5

<210> SEQ ID NO 525

```
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 525

Lys Glu Arg Glu Arg Ala
1               5

<210> SEQ ID NO 526
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 526

Lys Glu Lys Glu Arg Ala
1               5

<210> SEQ ID NO 527
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 527

Lys Glu Lys Gln Arg Ala
1               5

<210> SEQ ID NO 528
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 528

Ala Glu Ala Ala Ala Lys
1               5

<210> SEQ ID NO 529
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 529

Ala Ala His Ala Ala Ala
1               5

<210> SEQ ID NO 530
<211> LENGTH: 6
<212> TYPE: PRT
<213> ORGANISM: Artificial
<220> FEATURE:
<223> OTHER INFORMATION: Chemically synthesized artificial peptide

<400> SEQUENCE: 530

His Ala His Ala His Ala
1               5
```

We claim:

1. A non-native peptide comprising the sequence ZGPPISIDLPX$_{11}$X$_{12}$LLRKX$_{17}$IEIEKQEKEKQQAX$_{31}$X$_{32}$NAX$_{35}$X$_{36}$X$_{38}$X$_{39}$X$_{40}$ (SEQ ID NO: 531) wherein:
X$_{11}$ is selected from F, Y, L, I, and T;
X$_{12}$ is selected from Q, W, and Y;
X$_{17}$ is selected from V and M;
X$_{31}$ is selected from T and A;
X$_{32}$ is selected from N and T;
X$_{35}$ is selected from R and L;
X$_{36}$ is selected from L and I;
X$_{38}$ is selected from D and A;
X$_{39}$ is selected from T and R;
X$_{40}$ is selected from I and V;
and variants thereof having at least about 95% sequence identity to said peptide.

2. The peptide according to claim 1, wherein X$_{11}$ is selected from F, L, T, and Y.

3. The peptide according to claim 1, wherein X$_{11}$X$_{12}$ are selected from the group consisting of FQ, YQ, YW, LQ, LY, IY, and TY.

4. The peptide according to claim 1, wherein X$_{31}$X$_{32}$ are selected from the group consisting of AN, and TT.

5. The peptide according to claim 1, wherein X$_{35}$X$_{36}$ are selected from the group consisting of RL, LL, and RI.

6. The peptide according to claim 1, wherein X$_{38}$X$_{39}$X$_{40}$ are selected from the group consisting of DTI, ARI, ATI, DRV, and ARV.

7. The peptide according to claim 3, wherein X$_{31}$X$_{32}$ are selected from the group consisting of AN, and TT.

8. The peptide according to claim 3, wherein X$_{35}$X$_{36}$ are selected from the group consisting of RL, LL, and RI.

9. The peptide according to claim 3, wherein X$_{38}$X$_{39}$X$_{40}$ are selected from the group consisting of DTI, ARI, ATI, DRV, and ARV.

10. The peptide according to claim 4, wherein X$_{35}$X$_{36}$ are selected from the group consisting of RL, LL, and RI.

11. The peptide according to claim 4, wherein X$_{38}$X$_{39}$X$_{40}$ are selected from the group consisting of DTI, ARI, ATI, DRV, and ARV.

12. The peptide according to claim 5, wherein X$_{38}$X$_{39}$X$_{40}$ are selected from the group consisting of DTI, ARI, ATI, DRV, and ARV.

13. The peptide according to claim 7, wherein X$_{35}$X$_{36}$ are selected from the group consisting of RL, LL, and RI.

14. The peptide according to claim 7, wherein X$_{38}$X$_{39}$X$_{40}$ are selected from the group consisting of DTI, ARI, ATI, DRV, and ARV.

15. The peptide according to claim 10, wherein X$_{38}$X$_{39}$X$_{40}$ are selected from the group consisting of DTI, ARI, ATI, DRV, and ARV.

16. The peptide according to claim 1, wherein the peptide comprises a sequence selected from the group consisting of SEQ ID NO: 22, 144, 148, 149, 151, 278, 279, 286, 288, 311, 349, 350, 351, 352, and 353.

17. A method of preventing or treating a CRF$_2$R modulated disorder comprising administering to a host in need of such treatment a safe and effective amount of a peptide of claim 1.

18. The method according to claim 17, wherein the CRF$_2$R modulated disorder is skeletal muscle atrophy or muscular dystrophy.

19. A pharmaceutical composition comprising:
a. a safe and effective amount of a peptide of claim 1; and
b. a pharmaceutically acceptable carrier.

20. A kit for preventing or treating a CRF$_2$R modulated disorder comprising:
a. a peptide of claim 1 in a unit dose form; and
b. usage instruction.

21. A method of preventing or treating a CRF$_2$R modulated disorder comprising administering to a host in need of such treatment a safe and effective amount of a peptide of claim 16.

22. The method according to claim 21, wherein the CRF$_2$R modulated disorder is skeletal muscle atrophy or muscular dystrophy.

23. A pharmaceutical composition comprising:
a. a safe and effective amount of a peptide of claim 16; and
b. a pharmaceutically acceptable carrier.

24. A variant according to claim 1, having at least about 97% sequence identity to said peptide.

25. A non-native peptide comprising the sequence of SEQ ID NO: 278, and variants thereof having at least about 95% sequence identity to said peptide.

26. A variant according to claim 25, having at least about 97% sequence identity to said peptide.

27. A method of preventing or treating a CRF$_2$R modulated disorder comprising administering to a host in need of such treatment a safe and effective amount of a peptide of claim 25.

28. The method according to claim 27, wherein the CRF$_2$R modulated disorder is skeletal muscle atrophy or muscular dystrophy.

29. A pharmaceutical composition comprising:
a. a safe and effective amount of a peptide of claim 25; and
b. a pharmaceutically acceptable carrier.

30. A non-native peptide comprising the sequence of SEQ ID NO: 278.

31. A method of preventing or treating a CRF$_2$R modulated disorder comprising administering to a host in need of such treatment a safe and effective amount of a peptide of claim 30.

32. The method according to claim 31, wherein the CRF$_2$R modulated disorder is skeletal muscle atrophy or muscular dystrophy.

33. A pharmaceutical composition comprising:
a. a safe and effective amount of a peptide of claim 30; and
b. a pharmaceutically acceptable carrier.

34. A non-native peptide comprising the sequence ZGPPISIDLPX$_{11}$X$_{12}$LLRKX$_{17}$IEIEKQEKEKQQAX$_{31}$X$_{32}$NAX$_{35}$X$_{36}$LX$_{38}$X$_{39}$X$_{40}$ (SEQ ID NO: 531) wherein:
X$_{11}$ is selected from F, Y, L, I, and T;
X$_{12}$ is selected from Q, W, and Y;
X$_{17}$ is selected from V and M;
X$_{31}$ is selected from T and A;
X$_{32}$ is selected from N and T;
X$_{35}$ is selected from R and L;
X$_{36}$ is selected from L and I;
X$_{38}$ is selected from D and A;
X$_{39}$ is selected from T and R;
X$_{40}$ is selected from I and V.

35. A method of preventing or treating a CRF$_2$R modulated disorder comprising administering to a host in need of such treatment a safe and effective amount of a peptide of claim 34.

36. The method according to claim 35, wherein the CRF$_2$R modulated disorder is skeletal muscle atrophy or muscular dystrophy.

37. A pharmaceutical composition comprising:
a. a safe and effective amount of a peptide of claim 34; and
b. a pharmaceutically acceptable carrier.

* * * * *

UNITED STATES PATENT AND TRADEMARK OFFICE
CERTIFICATE OF CORRECTION

PATENT NO. : 7,192,924 B2
APPLICATION NO. : 10/317251
DATED : March 20, 2007
INVENTOR(S) : Robert Joseph Isfort et al.

It is certified that error appears in the above-identified patent and that said Letters Patent is hereby corrected as shown below:

<u>Column 1</u>
Line 9, please delete "June 14," and insert -- June 16 --.

<u>Column 9</u>
Line 37, please delete "Gin" and insert -- Gln --.

<u>Column 11</u>
Line 21, please delete "PI" and insert -- PIL --.

<u>Column 28</u>
Line 46, please delete "HIPMCP 55" and insert -- HPMCP 55 --.

<u>Column 341</u>
Please insert Sequence ID No. 531 after Seq. ID No. 530:
<210> 531
<211> 40
<212> PRT
<213> Artificial Sequence <220>
<223> Artificially derived peptide from various analogs

<220>
<221> MOD_RES
<222> (1)..(1)
<223> PYRROLIDONE CARBOXYLIC ACID

<220>
<221> MISC_FEATURE
<222> (11)..(11)
<223> Xaa = Phe, Tyr, Leu, Ile, or Thr

<220>
<221> MISC_FEATURE
<222> (12)..(12)
<223> Xaa = Gln, Trp, or Tyr

UNITED STATES PATENT AND TRADEMARK OFFICE
CERTIFICATE OF CORRECTION

PATENT NO. : 7,192,924 B2
APPLICATION NO. : 10/317251
DATED : March 20, 2007
INVENTOR(S) : Robert Joseph Isfort et al.

It is certified that error appears in the above-identified patent and that said Letters Patent is hereby corrected as shown below:

<220>
<221> MISC_FEATURE
<222> (17)..(17)
<223> Xaa = Val, or Met

<220>
<221> MISC_FEATURE
<222> (31)..(31)
<223> Xaa = Thr, or Ala

<220>
<221> MISC_FEATURE
<222> (32)..(32)

<220>
<221> MISC_FEATURE
<222> (35)..(35)
<223> Xaa = Arg, or Leu

<220>
<221> MISC_FEATURE
<222> (36)..(36)
<223> Xaa = Leu, or Ile

<220>
<221> MISC_FEATURE
<222> (38)..(38)
<223> Xaa = Asp, or Ala

<220>
<221> MISC_FEATURE
<222> (39)..(39)
<223> Xaa = Thr, or Arg

<220>
<221> MISC_FEATURE
<222> (40)..(40)
<223> Xaa = Ile, or Val

<400> 531

UNITED STATES PATENT AND TRADEMARK OFFICE
CERTIFICATE OF CORRECTION

PATENT NO. : 7,192,924 B2  Page 3 of 3
APPLICATION NO. : 10/317251
DATED : March 20, 2007
INVENTOR(S) : Robert Joseph Isfort et al.

It is certified that error appears in the above-identified patent and that said Letters Patent is hereby corrected as shown below:

Glx Gly Pro Pro Ile Ser Ile Asp Leu Pro Xaa Xaa Leu Leu Arg Lys
1               5                   10                  15

Xaa Ile Glu Ile Glu Lys Gln Glu Lys Glu Lys Gln Gln Ala Xaa Xaa
        20                  25                  30

Asn Ala Xaa Xaa Leu Xaa Xaa Xaa
        35              40

Column 343
    Claim 1, please delete "$X_{38}$" and insert -- $LX_{38}$ --.

Column 343
    Claim 15, please delete "ART" and insert -- ARI --.

Signed and Sealed this

Tenth Day of June, 2008

JON W. DUDAS
*Director of the United States Patent and Trademark Office*